United States Patent
Ostovic et al.

(10) Patent No.: US 10,765,649 B2
(45) Date of Patent: *Sep. 8, 2020

(54) STABLE AQUEOUS CAPSAICIN INJECTABLE FORMULATIONS AND MEDICAL USES THEREOF

(71) Applicant: Centrexion Therapeutics Corporation, Boston, MA (US)

(72) Inventors: Drazen Ostovic, Redwood City, CA (US); Gary Fred Musso, Hopkinton, MA (US)

(73) Assignee: Centrexion Therapeutics Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/695,831

(22) Filed: Nov. 26, 2019

(65) Prior Publication Data

US 2020/0093766 A1 Mar. 26, 2020

Related U.S. Application Data

(63) Continuation of application No. 16/400,278, filed on May 1, 2019, now Pat. No. 10,493,047, which is a continuation of application No. PCT/US2017/059628, filed on Nov. 2, 2017.

(60) Provisional application No. 62/416,345, filed on Nov. 2, 2016.

(51) Int. Cl.
| | |
|---|---|
| A61K 31/165 | (2006.01) |
| A61K 31/167 | (2006.01) |
| A61K 47/34 | (2017.01) |
| A61K 45/06 | (2006.01) |
| A61K 47/14 | (2017.01) |
| A61K 9/00 | (2006.01) |
| A61P 25/00 | (2006.01) |
| A61P 29/02 | (2006.01) |
| A61K 47/55 | (2017.01) |
| A61K 47/54 | (2017.01) |
| A61K 31/05 | (2006.01) |

(52) U.S. Cl.
CPC .......... *A61K 31/165* (2013.01); *A61K 9/0019* (2013.01); *A61K 31/05* (2013.01); *A61K 31/167* (2013.01); *A61K 45/06* (2013.01); *A61K 47/14* (2013.01); *A61K 47/34* (2013.01); *A61K 47/547* (2017.08); *A61K 47/55* (2017.08); *A61P 25/00* (2018.01); *A61P 29/02* (2018.01)

(58) Field of Classification Search
CPC ........ A61K 31/165; A61K 47/14; A61K 9/00; A61P 29/02

See application file for complete search history.

(56) References Cited

U.S. PATENT DOCUMENTS

| | | |
|---|---|---|
| 4,599,342 A | 7/1986 | LaHann |
| 5,021,450 A | 6/1991 | Blumberg |
| 5,099,030 A | 3/1992 | Gardner et al. |
| 5,318,960 A | 6/1994 | Toppo |
| 5,431,914 A | 7/1995 | Adekunle et al. |
| 5,962,532 A | 10/1999 | Campbell et al. |
| 5,985,860 A | 11/1999 | Toppo |
| 6,060,060 A | 5/2000 | Belgorod |
| 6,248,788 B1 | 6/2001 | Robbins et al. |
| 6,277,398 B1 | 8/2001 | Caruso |
| 7,943,166 B2 | 5/2011 | Muhammad et al. |
| 7,964,644 B2 | 6/2011 | Meyer |
| 8,158,682 B2 | 4/2012 | Sangameswaran et al. |
| 8,263,093 B2 | 9/2012 | Muhammad et al. |
| 8,273,390 B2 | 9/2012 | Muhammad et al. |
| 8,338,457 B2 | 12/2012 | Iadarola et al. |
| 8,367,733 B2 | 2/2013 | Burch et al. |
| 8,420,600 B2 | 4/2013 | Burch et al. |
| 8,637,569 B2 | 1/2014 | Birbara |
| 8,703,741 B2 | 4/2014 | Meyer |
| 8,734,770 B2 | 5/2014 | Muhammad et al. |
| 9,044,452 B2 | 6/2015 | Meyer |
| 9,359,316 B1 | 6/2016 | Husfeld et al. |
| 9,956,166 B2 | 5/2018 | Zucker et al. |
| 9,956,190 B2 | 5/2018 | Birbara et al. |
| 10,493,047 B2 | 12/2019 | Ostovic |
| 2003/0104085 A1 | 6/2003 | Yeomans |
| 2005/0020690 A1 | 1/2005 | Burch et al. |
| 2006/0148903 A1 | 7/2006 | Burch et al. |

(Continued)

FOREIGN PATENT DOCUMENTS

| | | |
|---|---|---|
| CN | 101507818 A | 8/2009 |
| EP | 0646372 A1 | 4/1995 |

(Continued)

OTHER PUBLICATIONS

U.S. Appl. No. 16/342,652, Stable Aqueous Capsaicin Injectable Formulations and Medical Uses Thereof, filed Apr. 17, 2019.
U.S. Appl. No. 16/695,824, Stable Aqueous Capsaicin Injectable Formulations and Medical Uses Thereof, filed Nov. 26, 2019.
Akesson in "A comparison of two formulations of intradermal capsaicin as models of neuropathic pain in healthy volunteers" (2007) Master Thesis in Pharmacy; The University of Adelaide Australia.
Botz in "The role of sensory neuropeptides in mouse models of neuropathy and immune arthritis" (year 2015) University PECS, Medical School.

(Continued)

*Primary Examiner* — Dennis Heyer
(74) *Attorney, Agent, or Firm* — Dechert LLP

(57) ABSTRACT

The invention provides stable, aqueous capsaicin injectable formulations, a unit dose containing such injectable formulations, medical kits, and methods for using such injectable formulations and unit doses to treat patients suffering from pain, such as osteoarthritic knee pain. The stable, aqueous capsaicin injectable formulations may contain, for example, capsaicin, a solubilizing agent (e.g., a polyethylene glycol ester of a ($C_{15}$-$C_{25}$) hydroxyalkanoic acid), an antioxidant, and water.

30 Claims, No Drawings

(56) References Cited

U.S. PATENT DOCUMENTS

| | | |
|---|---|---|
| 2007/0021338 A1 | 1/2007 | Hansen |
| 2010/0047181 A1 | 2/2010 | Meyer |
| 2010/0196281 A1 | 8/2010 | Meyer |
| 2010/0234470 A1 | 9/2010 | Sangameswaran et al. |
| 2011/0311952 A1 | 12/2011 | Fairfield et al. |
| 2013/0252925 A1 | 9/2013 | Bucks et al. |
| 2013/0280176 A1 | 10/2013 | Diezi et al. |
| 2013/0280177 A1 | 10/2013 | Raman et al. |
| 2013/0303495 A1 | 11/2013 | Dhingra et al. |
| 2014/0017313 A1 | 1/2014 | Coulter et al. |
| 2014/0142073 A1 | 5/2014 | Birbara et al. |
| 2014/0161889 A1 | 6/2014 | Mikulasik et al. |
| 2015/0132374 A1 | 5/2015 | Coulter et al. |
| 2015/0132396 A1 | 5/2015 | Coulter et al. |
| 2015/0133561 A1* | 5/2015 | Birbara .......... A61P 25/04 514/627 |
| 2015/0306233 A1 | 10/2015 | Chiou et al. |
| 2016/0339105 A1 | 11/2016 | Shah et al. |
| 2016/0346241 A1 | 12/2016 | Amrutkar et al. |
| 2016/0354315 A1 | 12/2016 | Li |
| 2017/0239198 A1 | 8/2017 | Muzari |
| 2017/0266139 A1 | 9/2017 | Burch et al. |
| 2018/0169039 A1 | 6/2018 | Muhammad et al. |
| 2018/0311189 A1 | 11/2018 | Campbell et al. |
| 2019/0022036 A1 | 1/2019 | Campbell et al. |
| 2019/0038573 A1 | 2/2019 | Westphal et al. |

FOREIGN PATENT DOCUMENTS

| | | |
|---|---|---|
| EP | 3119794 B1 | 10/2017 |
| WO | 98/020867 A1 | 5/1998 |
| WO | 98/040070 A1 | 9/1998 |
| WO | 02/076444 A1 | 10/2002 |
| WO | 04/056305 A2 | 7/2004 |
| WO | 04/058286 A1 | 7/2004 |
| WO | 08/005802 A2 | 1/2008 |
| WO | 14/019095 A1 | 2/2014 |
| WO | 14/075084 A2 | 5/2014 |
| WO | 14/128233 A1 | 8/2014 |
| WO | 15/052510 A1 | 4/2015 |
| WO | 15/198059 A1 | 12/2015 |
| WO | 15/198350 A1 | 12/2015 |
| WO | 16/077749 A1 | 5/2016 |
| WO | 16/086063 A1 | 6/2016 |
| WO | 16/126540 A1 | 8/2016 |
| WO | 17/087803 A1 | 5/2017 |
| WO | 17/127628 A1 | 7/2017 |
| WO | 17/147146 A1 | 8/2017 |
| WO | 17/205534 A1 | 11/2017 |
| WO | 18/217937 A1 | 11/2018 |

OTHER PUBLICATIONS

Chen et al. in Arzneimittelforschung (2010) vol. 60(9), pp. 571-574 (Abstract only).
Costanzo et al. in Cough (2014) 10:6; doi: 10.1186/1745-9974-10-6 (published Sep. 25, 2014).
Ezawa et al. in International Journal of Medicinal Chemistry (2016) Article ID 8723139, 9 pages.
Galano et al. in J. Phys. Chem. B (2012) vol. 116, pp. 1200-1208.
Gustafsson et al. in Br. J. Clin. Pharmacol. (2009) vol. 68(4), pp. 511-517
Ha et al. in J. Pharm. Sci. (2002) vol. 91(10), pp. 2252-2264 (Abstract only).
Kadekawa et al. in Am. J. Physiol. Renal Physiol. (2017) vol. 313, F796-F804.
Kistner et al. in Sci. Rep. (2016) vol. 6, p. 28621.
Kopec et al. in Cough (2008) 4:3 doi 10.1186/1745-9974-4-3 (published May 27, 2008).
Pharma Ingredients & Services Technical Information by BASF (Mar. 2012).
Shen et al. in Journal of Inclusion Phenomena and Macrocyclic Chemistry (2012) vol. 72, pp. 263-274.
Tateba et al. in Agric. Biol. Chem. (1991) vol. 55(3), pp. 873-874.
Turgut et al. in Environ. Sci. Pollut. Res. Int. (2004) vol. 11(1), pp. 7-10 (Abstract only).
Zhang et al. in Journal of Pain Research (2014) vol. 7, pp. 547-554.
Zhao et al. in Pharm Biol. (2016) vol. 54(1), pp. 130-138 (Abstract only).
International Search Report and Written Opinion for PCT/US2017/059628 dated Feb. 13, 2018 (8 pages).
BASF Pharma Ingredients & Services: Technical Information Soluplus (Jul. 2010).

* cited by examiner

STABLE AQUEOUS CAPSAICIN INJECTABLE FORMULATIONS AND MEDICAL USES THEREOF

CROSS-REFERENCE TO RELATED APPLICATIONS

This application is a continuation of U.S. patent application Ser. No. 16/400,278, filed May 1, 2019, which is a continuation of International (PCT) Patent Application Serial No. PCT/US2017/059628, filed Nov. 2, 2017, which claims the benefit of and priority to U.S. Provisional Patent Application Ser. No. 62/416,345, filed Nov. 2, 2016; the entire contents of these applications are incorporated herein by reference in their entirety.

FIELD OF THE INVENTION

The invention provides stable, aqueous capsaicin injectable formulations, a unit dose containing such injectable formulations, medical kits, and methods for using such injectable formulations and unit doses to treat patients suffering from pain, such as osteoarthritic knee pain.

BACKGROUND

Pain can function as a protective mechanism that allows healthy human beings and animals to avoid tissue damage and/or prevent further damage to injured tissue. However, there are many instances in which pain persists beyond its usefulness. Such unnecessary suffering from pain can impair a subject's physical mobility, mental performance, and even contribute to depression.

Substantial resources have been devoted over the years to researching the causes of various types of pain and to the development of medicine to attenuate pain experienced by a patient. Exemplary classes of common pain-relief medications include opioids, non-steroidal anti-inflammatory agents, corticosteroids, and centrally acting agents such as anti-depressants, anti-epileptics, pregabalin, and gabapentin. Capsaicin has been described for use in treating pain. See, for example, U.S. Pat. Nos. 5,962,532; 8,420,600; 8,367,733; and 8,158,682. Certain commercial products containing capsaicin for pain relief formulate the capsaicin as a cream (e.g., Capzasin) or in a patch (e.g., a capsaicin-containing transdermal patch marketed under the trade name QUTENZA) for topical application to the skin of a patient.

Because capsaicin is soluble in organic solvents, but poorly soluble in water, new formulations are needed for achieving a desirable amount of capsaicin dissolved in an aqueous formulation that is suitable for injection into a patient, and which has suitable stability for use in typical distribution routes for delivering pharmaceutical agents to medical facilities which typically involve storage of the formulation for certain lengths of time. The present invention addresses the foregoing need and provides other related advantages.

SUMMARY

The invention provides stable, aqueous capsaicin injectable formulations, a unit dose containing such injectable formulations, medical kits, and methods for using such injectable formulations and unit doses to treat patients suffering from pain, such as osteoarthritic knee pain. The invention is based in part on the discovery that a solubilizing agent containing a polyethylene glycol ester of a long-chain hydroxyalkanoic acid or a polyethylene glycol ester of a long-chain hydroxyalkenoic acid (such as a mixture containing a polyethylene glycol ester of 12-hydroxystearic acid, a polyethylene glycol ester of 12-((12-hydroxyoctadecanoyl)oxy)octadecanoic acid, and polyethylene glycol sold by BASF under the trade name KOLLIPHOR® HS 15) was able to solubilize greater amounts of capsaicin than other tested solubilizing agents in the aqueous medium at the desired pH range, and yet produced a formulation suitable for injection to a patient and that is sufficiently stable to storage that it may be used in the typical distribution routes for pharmaceutical agents. Further illustrative benefits of the injectable formulations of the invention are the multiple benefits provided by the above-cited solubilizing agent relative to use of a polysorbate to create a stable, aqueous capsaicin injectable formulation suitable for administration to a patient. The solubilizing agent used in the invention formulations is superiorly compatible with capsaicin, which improves the stability of the formulation to storage. By contrast, polysorbates, such as Polysorbate 80, can have a greater propensity to form peroxides. Such peroxides can cause undesired oxidation of capsaicin, resulting in loss of capsaicin during storage of the formulation and increase in the amount and identity of impurities. The solubilizing agent specified above in the formulations of the invention overcomes this deficiency of polysorbate. Accordingly, the formulations provide the benefit that they achieve elevated levels of dissolved capsaicin in an aqueous medium suitable for injection directly into a patient, and the formulations are stable to storage.

The stable, aqueous capsaicin injectable formulations described above for capsaicin may be used more generally to solubilize a vanilloid receptor agonist for administration by to a patient by injection or other route. Accordingly, another aspect of the invention provides a stable, aqueous injectable formulation containing a vanilloid receptor agonist, such as resiniferatoxin. Such formulations may be used in a unit dose form, in medical kits, and in methods for treating patients suffering from pain, such as osteoarthritic knee pain.

Various aspects and embodiments of the invention are described in further detail below. For example, one aspect of the invention provides an aqueous, capsaicin injectable formulation, comprising:

a. about 0.03% (w/w) to about 0.3% (w/w) of capsaicin;
b. about 0.1% (w/w) to about 3% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group;
c. about 0.001% (w/w) to about 2% (w/w) of an antioxidant; and
d. at least 92% (w/w) water.

More specific embodiments include, for example, formulations where the solubilizing agent comprises a ($C_{17}$) hydroxyalkyl-$CO_2$-(polyethylene glycolyl)-H, ($C_{17}$)hydroxyalkyl-$CO_2$—($C_{17}$)alkylene-$CO_2$-(polyethylene glycolyl)-H, and polyethylene glycol. In certain embodiments, the formulation may be further characterized according to, for example, its stability to storage, such as where less than 1% of the capsaicin degrades upon storage of the formulation at 40° C. for 24 weeks. Additional description of injectable formulations is provided in the detailed description, along with specific illustrative injectable formulations.

Another aspect of the invention provides a unit dosage form comprising a formulation described herein, such as a formulation in any one of Tables 1-5. The unit dosage form may be further characterized according to, for example, the volume of the unit dosage form, such as where the unit dosage form has a volume in the range of about 0.5 mL to about 3 mL, or more preferably about 2 mL.

Another aspect of the invention provides a method of treating pain in a patient, where the method comprises administering to a patient in need thereof a therapeutically effective amount of a formulation described herein, such as a formulation in any one of Tables 1-5, to a site at or near the location of pain, in order to treat the pain. The pain may be joint pain, such as where the joint is a knee joint, hip joint, shoulder joint, elbow joint, carpal joint, tarsal joint, or metatarsal joint. In certain embodiments, the joint is affected by osteoarthritis. In a preferred embodiment, the pain is pain in a knee joint affected by osteoarthritis. In other embodiments, the pain is pain in or around soft tissue.

DETAILED DESCRIPTION OF THE INVENTION

The invention provides stable, aqueous capsaicin injectable formulations, a unit dose containing such injectable formulations, medical kits, and methods for using such injectable formulations and unit doses to treat patients suffering from pain, such as osteoarthritic knee-joint pain. The invention is based in part on the discovery that a solubilizing agent containing a polyethylene glycol ester of a long-chain hydroxyalkanoic acid or a polyethylene glycol ester of a long-chain hydroxyalkenoic acid (such as a mixture containing a polyethylene glycol ester of 12-hydroxystearic acid, a polyethylene glycol ester of 12-((12-hydroxyoctadecanoyl)oxy)octadecanoic acid, and polyethylene glycol sold by BASF under the tradename KOLLIPHOR® HS 15) was able to solubilize greater amounts of capsaicin than other tested solubilizing agents in the aqueous medium at the desired pH range, and yet produced a formulation suitable for injection to a patient and that is sufficiently stable to storage that it may be used in the typical distribution routes for pharmaceutical agents. Further illustrative benefits of the injectable formulations of the invention are the multiple benefits provided by the above-cited solubilizing agent relative to use of a polysorbate to create a stable, aqueous capsaicin injectable formulation suitable for administration to a patient. The solubilizing agent used in the invention formulations is superiorly compatible with capsaicin, which improves the stability of the formulation to storage. By contrast, polysorbates, such as Polysorbate 80, can have a greater propensity to form peroxides. Such peroxides can cause undesired oxidation of capsaicin, resulting in loss of capsaicin during storage of the formulation and increase in the amount and identity of impurities. The solubilizing agent specified above in the formulations of the invention overcomes this deficiency of polysorbate. Accordingly, the formulations provide the benefit that they achieve elevated levels of dissolved capsaicin in an aqueous medium suitable for injection directly into a patient, and the formulations are stable to storage.

The stable, aqueous capsaicin injectable formulations described above for capsaicin may be used more generally to solubilize a vanilloid receptor agonist for administration by injection or other route. Accordingly, another aspect of the invention provides a stable, aqueous injectable formulation containing a vanilloid receptor agonist, such as resiniferatoxin. Such formulations may be used in a unit dose form, in medical kits, and in methods for treating patients suffering from pain, such as osteoarthritic knee pain.

Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "about" means within 10% of the stated value. In certain embodiments, the value may be within 8%, 6%, 4%, 2%, or 1% of the stated value.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "hydroxyalkyl" refers to an alkyl group substituted by 1 or 2 hydroxyl groups. In certain embodiments, the hydroxyalkyl is an alkyl group substituted by only 1 hydroxyl group.

The term "hydroxyalkanoic acid" refers to saturated straight or branched hydrocarbon that is substituted by (i) one —$CO_2H$ group, and (ii) one or two hydroxyl groups.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

The term "hydroxyalkenyl" refers to an alkenyl group substituted by 1 or 2 hydroxyl groups. In certain embodiments, the hydroxyalkenyl is an alkenyl group substituted by only 1 hydroxyl group.

The term "hydroxyalkenoic acid" refers to an unsaturated straight or branched hydrocarbon having one carbon-carbon double bond, wherein the hydrocarbon is substituted by (i) one —$CO_2H$ group, and (ii) one or two hydroxyl groups.

The term "polyethylene glycolyl" refers to a radical of polyethylene glycol. The polyethylene glycolyl is a chemical fragment that is part of a larger molecule. When the polyethylene glycolyl is bonded at one location to the remainder of the molecule, then the polyethylene glycolyl is a mono-radical, such as "—$(CH_2CH_2O)x$-H" where x is an integer greater than 1. When the polyethylene glycolyl is used as a component within a molecule connecting two fragments of the molecule, the polyethylene glycolyl is a diradical, having a point of attachment at each terminus of the polyethylene glycolyl, which may be illustrated as "—$(CH_2CH_2O)x$-" where x is an integer greater than 1. In certain embodiments, x is an integer in the range of about 5 to about 100, about 5 to about 50, about 5 to about 25, about 5 to about 15, about 10 to about 50, about 10 to about 30, or about 10 to about 20. In certain embodiments, x is about 10, 11, 12, 13, 14, 15, 16, 17, 18, or 19. In certain preferred embodiments, x is about 15.

Macrogol 15 hydroxystearate has CAS Registry No 70142-34-6, and is a mixture containing (a) about 70% (w/w) of a mixture of stereomerically pure intermediates, reagents, and catalysts by well-known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or

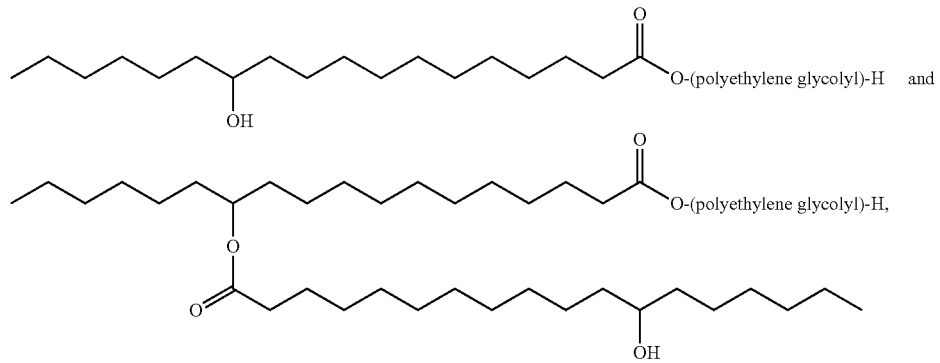

and (b) about 30% (w/w) polyethylene glycol; where the polyethylene glycolyl has a weight-average molecular weight of about 660 g/mol; which is sold and marketed by BASF as KOLLIPHOR® HS 15.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Specific stereoisomers can also be obtained selectively using arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_3$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Aqueous Injectable Formulations

One aspect of the invention provides aqueous, injectable formulations. The formulations provide the benefits that they are stable to storage and can be administered directly to a patient via injection. The formulations contain a solubilizing agent to achieve the desired higher concentration of vanilloid receptor agonist in the aqueous medium. The formulations are particularly useful for administering capsaicin by injection to a patient.

As indicated above, the invention is based in part on the discovery that a solubilizing agent containing a polyethylene glycol ester of a long-chain hydroxyalkanoic acid or a polyethylene glycol ester of a long-chain hydroxyalkenoic acid (such as a mixture containing a polyethylene glycol ester of 12-hydroxystearic acid, a polyethylene glycol ester of 12-((12-hydroxyoctadecanoyl)oxy)octadecanoic acid, and polyethylene glycol sold by BASF under the trade name KOLLIPHOR® HS 15) was able to solubilize greater amounts of capsaicin than other tested solubilizing agents in the aqueous medium at the desired pH range, and yet produced a formulation suitable for injection to a patient and that is sufficiently stable to storage that it may be used in the typical distribution routes for pharmaceutical agents. Further illustrative benefits of the injectable formulations of the invention are the multiple benefits provided by the above-cited solubilizing agent relative to use of a polysorbate to create a stable, aqueous capsaicin injectable formulation suitable for administration to a patient. The solubilizing agent used in the invention formulations is superiorly compatible with capsaicin, which improves the stability of the formulation to storage. By contrast, polysorbates, such as Polysorbate 80, can have a greater propensity to form peroxides. Such peroxides can cause undesired oxidation of capsaicin, resulting in loss of capsaicin during storage of the formulation and increase in the amount and identity of impurities. The solubilizing agent specified above in the formulations of the invention overcomes this deficiency of polysorbate. Additionally, the solubilizing agent used in the invention formulations overcomes the adverse side effect of polysorbates, such as Polysorbate 80, of triggering release of histamine when administered to a patient. Accordingly, the specific solubilizing agent described herein for use in the invention formulations imparts multiple benefits.

Additional features of the aqueous injectable formulations are described below.

One aspect of the invention provides an aqueous, capsaicin injectable formulation, wherein the formulation comprises
 a. about 0.03% (w/w) to about 0.3% (w/w) of capsaicin;
 b. about 0.1% (w/w) to about 3% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group;
 c. about 0.001% (w/w) to about 2% (w/w) of an antioxidant; and
 d. at least 92% (w/w) water.

Another aspect of the invention provides an aqueous, capsaicin injectable formulation, wherein the formulation comprises
 a. about 0.01% (w/w) to about 0.5% (w/w) of capsaicin;
 b. about 0.01% (w/w) to about 5% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group; and
 c. water.

Another aspect of the invention provides an aqueous, vanilloid receptor agonist injectable formulation, wherein the formulation comprises
 a. a vanilloid receptor agonist (e.g., about 0.001% (w/w) to about 5% (w/w) of the vanilloid receptor agonist);
 b. about 0.01% (w/w) to about 5% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group; and
 c. water.

Another aspect of the invention provides an aqueous, capsaicin injectable formulation, wherein the formulation comprises
  a. about 0.03% (w/w) to about 0.3% (w/w) of capsaicin;
  b. about 0.1% (w/w) to about 3% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group; and
  c. at least 92% (w/w) water.

Another aspect of the invention provides an aqueous, capsaicin injectable formulation, wherein the formulation comprises
  a. about 0.03% (w/w) to about 0.1% (w/w) of capsaicin;
  b. about 0.5% (w/w) to about 1.5% (w/w) of a solubilizing agent, wherein the solubilizing agent comprises (i) a polyethylene glycol ester of a ($C_{15}$-$C_{25}$) hydroxyalkanoic acid, or (ii) a polyethylene glycol ester of a ($C_{15}$-$C_{25}$) alkanoic acid substituted by a —OC(O)($C_{14}$-$C_{24}$) hydroxyalkyl group; and
  c. at least 92% (w/w) water.

Exemplary components and features of the aqueous injectable formulations are described in more detail below.

Amount of Solubilizing Agent

The formulation can be further characterized according to the amount of solubilizing agent in the formulation. For example, in certain embodiments, the formulation comprises about 0.5% (w/w) to about 1.5% (w/w) of the solubilizing agent. In certain other embodiments, the formulation comprises about 0.8% (w/w) to about 1.2% (w/w) of the solubilizing agent. In certain other embodiments, the formulation comprises about 1% (w/w) of the solubilizing agent. In certain other embodiments, the formulation comprises about 1.5% (w/w) to about 2.5% (w/w) of the solubilizing agent. In certain other embodiments, the formulation comprises about 2% (w/w) of the solubilizing agent.

Identity of Solubilizing Agent

The formulation can be further characterized according to the identity of the solubilizing agent in the formulation. For example, in certain embodiments, the solubilizing agent comprises (i) a polyethylene glycol ester of a ($C_{15}$-$C_{25}$) hydroxyalkanoic acid, or (ii) a polyethylene glycol ester of a ($C_{15}$-$C_{25}$) hydroxyalkenoic acid. In certain embodiments, the solubilizing agent comprises a ($C_{14}$-$C_{24}$)hydroxyalkyl-$CO_2$-(polyethylene glycolyl)-H and ($C_{14}$-$C_{24}$)hydroxyalkyl-$CO_2$—($C_{14}$-$C_{24}$)alkylene-$CO_2$-(polyethylene glycolyl)-H. In certain embodiments, the solubilizing agent comprises a ($C_{14}$-$C_{24}$)hydroxyalkyl-$CO_2$-(polyethylene glycolyl)-H, ($C_{14}$-$C_{24}$)hydroxyalkyl-$CO_2$—($C_{14}$-$C_{24}$)alkylene-$CO_2$-(polyethylene glycolyl)-H, and polyethylene glycol. In certain embodiments, the solubilizing agent comprises (a) from about 60% (w/w) to about 80% (w/w) of a mixture of ($C_{14}$-$C_{24}$)hydroxyalkyl-$CO_2$-(polyethylene glycolyl)-H and ($C_{14}$-$C_{24}$)hydroxyalkyl-$CO_2$—($C_{14}$-$C_{24}$)alkylene-$CO_2$-(polyethylene glycolyl)-H, and (b) from about 20% (w/w) to about 40% (w/w) polyethylene glycol. In certain embodiments, the solubilizing agent comprises (a) about 70% (w/w) of a mixture of ($C_{14}$-$C_{24}$)hydroxyalkyl-$CO_2$-(polyethylene glycolyl)-H and ($C_{14}$-$C_{24}$)hydroxyalkyl-$CO_2$—($C_{14}$-$C_{24}$)alkylene-$CO_2$-(polyethylene glycolyl)-H, and (b) about 30% (w/w) polyethylene glycol. In certain embodiments, the solubilizing agent is a mixture of ($C_{14}$-$C_{24}$)hydroxyalkyl-$CO_2$-(polyethylene glycolyl)-H, ($C_{14}$-$C_{24}$)hydroxyalkyl-$CO_2$—($C_{14}$-$C_{24}$)alkylene-$CO_2$-(polyethylene glycolyl)-H, and polyethylene glycol. In certain embodiments, the solubilizing agent is a mixture of (a) from about 60% (w/w) to about 80% (w/w) of a mixture of ($C_{14}$-$C_{24}$)hydroxyalkyl-$CO_2$-(polyethylene glycolyl)-H and ($C_{14}$-$C_{24}$)hydroxyalkyl-$CO_2$—($C_{14}$-$C_{24}$)alkylene-$CO_2$-(polyethylene glycolyl)-H, and (b) from about 20% (w/w) to about 40% (w/w) polyethylene glycol. In certain embodiments, the solubilizing agent is a mixture of (a) about 70% (w/w) of a mixture of ($C_{14}$-$C_{24}$)hydroxyalkyl-$CO_2$-(polyethylene glycolyl)-H and ($C_{14}$-$C_{24}$)hydroxyalkyl-$CO_2$—($C_{14}$-$C_{24}$)alkylene-$CO_2$-(polyethylene glycolyl)-H, and (b) about 30% (w/w) polyethylene glycol.

In certain embodiments, the solubilizing agent comprises (a) a polyethylene glycol ester of a ($C_{15}$-$C_{25}$) hydroxyalkanoic acid and (b) a polyethylene glycol ester of a ($C_{15}$-$C_{25}$) alkanoic acid substituted by a —OC(O)($C_{14}$-$C_{24}$) hydroxyalkyl group, wherein the mole ratio of (a) to (b) is in the range of 10:1 to 1:10, 5:1 to 1:5, 2:1 to 1:2, 10:1 to 5:1, 5:1 to 2:1, 2:1 to 1:1, 1:1 to 1:2, 1:2 to 1:5, 1:5 to 1:10, or is greater than 10:1, or less than 1:1.

In a more specific embodiment, the solubilizing agent comprises a ($C_{17}$)hydroxyalkyl-$CO_2$-(polyethylene glycolyl)-H and ($C_{17}$)hydroxyalkyl-$CO_2$—($C_{17}$)alkylene-$CO_2$-(polyethylene glycolyl)-H. In certain embodiments, the solubilizing agent comprises a ($C_{17}$)hydroxyalkyl-$CO_2$-(polyethylene glycolyl)-H, ($C_{17}$)hydroxyalkyl-$CO_2$—($C_{17}$)alkylene-$CO_2$-(polyethylene glycolyl)-H, and polyethylene glycol. In certain embodiments, the solubilizing agent comprises (a) from about 60% (w/w) to about 80% (w/w) of a mixture of ($C_{17}$)hydroxyalkyl-$CO_2$-(polyethylene glycolyl)-H and ($C_{17}$)hydroxyalkyl-$CO_2$—($C_{17}$)alkylene-$CO_2$-(polyethylene glycolyl)-H, and (b) from about 20% (w/w) to about 40% (w/w) polyethylene glycol. In certain embodiments, the solubilizing agent comprises (a) about 70% (w/w) of a mixture of ($C_{17}$)hydroxyalkyl-$CO_2$-(polyethylene glycolyl)-H and ($C_{17}$)hydroxyalkyl-$CO_2$—($C_{17}$)alkylene-$CO_2$-(polyethylene glycolyl)-H, and (b) about 30% (w/w) polyethylene glycol. In certain embodiments, the solubilizing agent is a mixture of (a) from about 60% (w/w) to about 80% (w/w) of a mixture of ($C_{17}$)hydroxyalkyl-$CO_2$-(polyethylene glycolyl)-H and ($C_{17}$)hydroxyalkyl-$CO_2$—($C_{17}$)alkylene-$CO_2$-(polyethylene glycolyl)-H, and (b) from about 20% (w/w) to about 40% (w/w) polyethylene glycol. In certain embodiments, the solubilizing agent is a mixture of (a) about 70% (w/w) of a mixture of ($C_{17}$)hydroxyalkyl-$CO_2$-(polyethylene glycolyl)-H and ($C_{17}$)hydroxyalkyl-$CO_2$—($C_{17}$)alkylene-$CO_2$-(polyethylene glycolyl)-H, and (b) about 30% (w/w) polyethylene glycol.

In certain embodiments, the mole ratio of (a) ($C_{14}$-$C_{24}$)hydroxyalkyl-$CO_2$-(polyethylene glycolyl)-H to (b) ($C_{14}$-$C_{24}$)hydroxyalkyl-$CO_2$—($C_{14}$-$C_{24}$)alkylene-$CO_2$-(polyethylene glycolyl)-H in the formulation is in the range of 10:1 to 1:10, 5:1 to 1:5, 2:1 to 1:2, 10:1 to 5:1, 5:1 to 2:1, 2:1 to 1:1, 1:1 to 1:2, 1:2 to 1:5, 1:5 to 1:10, or is greater than 10:1, or less than 1:1. In certain embodiments, the mole ratio of (a) ($C_{17}$)hydroxyalkyl-$CO_2$-(polyethylene glycolyl)-H to (b) ($C_{17}$)hydroxyalkyl-$CO_2$—($C_{17}$)alkylene-$CO_2$-(polyethylene glycolyl)-H in the formulation is in the range of 10:1 to 1:10, 5:1 to 1:5, 2:1 to 1:2, 10:1 to 5:1, 5:1 to 2:1, 2:1 to 1:1, 1:1 to 1:2, 1:2 to 1:5, 1:5 to 1:10, or is greater than 10:1, or less than 1:1.

In a more specific embodiment, the solubilizing agent comprises
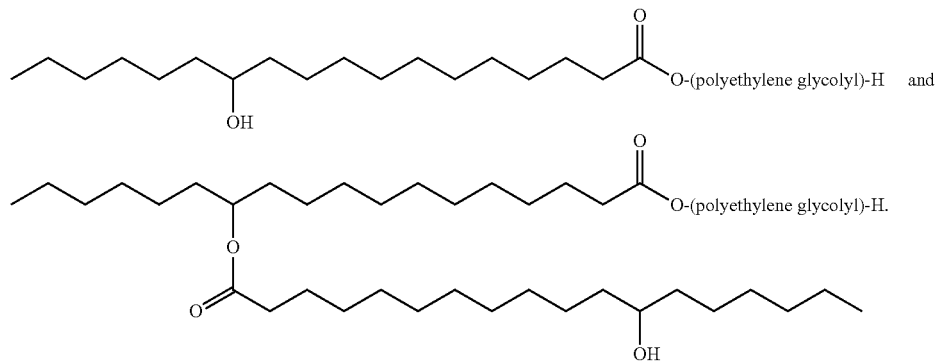
In another more specific embodiment, the solubilizing agent is a mixture of
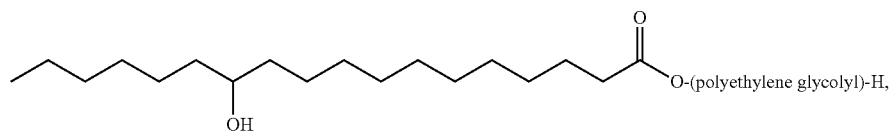
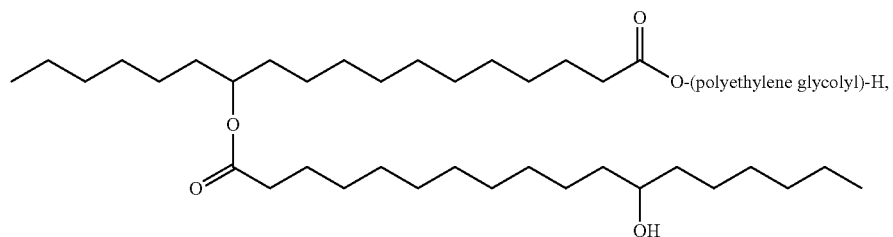
and polyethylene glycol. In certain other embodiments, the solubilizing agent comprises (a) about 70% (w/w) of a mixture of
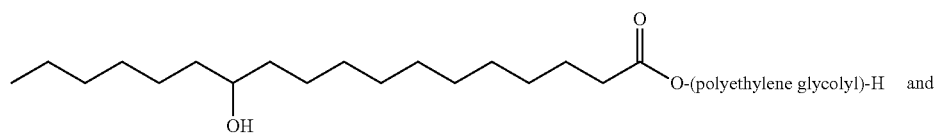
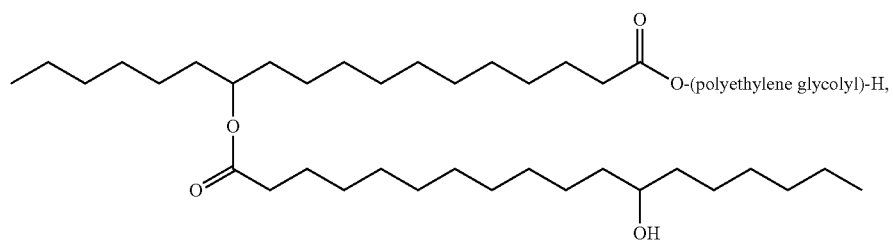

and (b) about 30% (w/w) polyethylene glycol. In certain other embodiments, the solubilizing agent is a mixture of (a) about 70% (w/w) of a mixture of

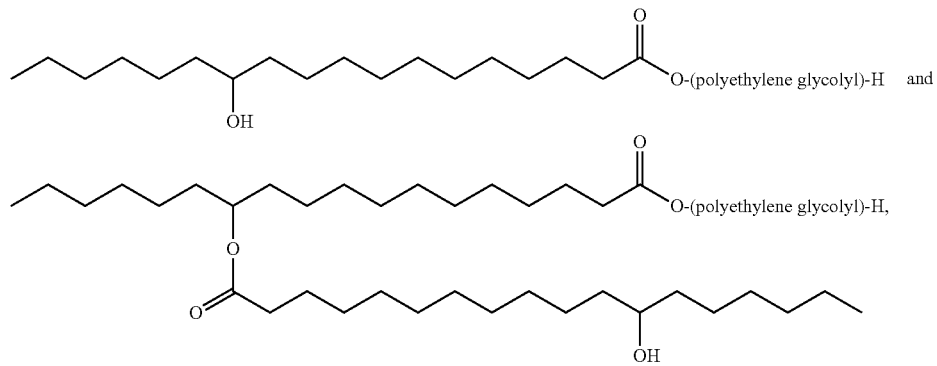

and (b) about 30% (w/w) polyethylene glycol. In certain other embodiments, the solubilizing agent comprises (a) from 68% (w/w) to 72% (w/w) of a mixture of

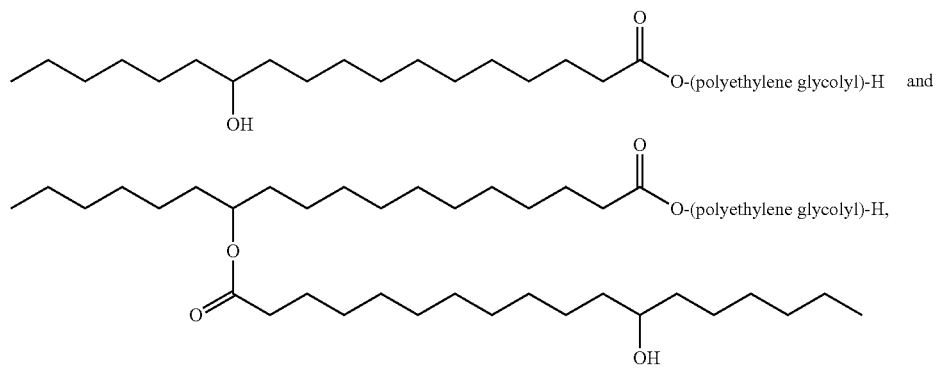

and (b) from 28% (w/w) to 32% (w/w) polyethylene glycol. In certain embodiments, the mole ratio of (a)

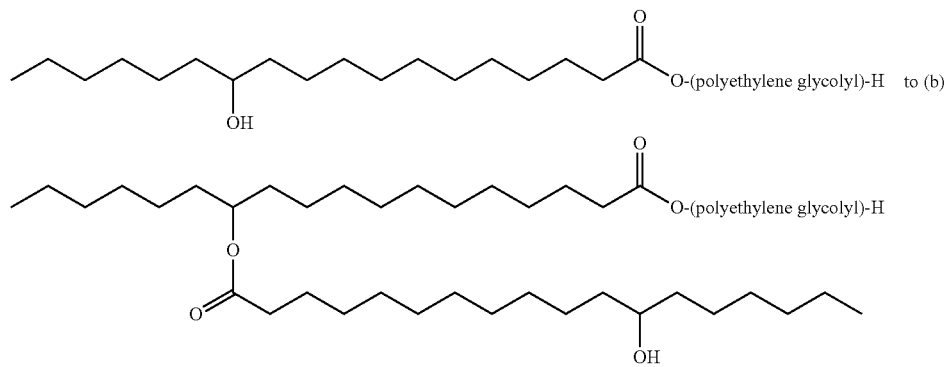

in the formulation is in the range of 10:1 to 1:10, 5:1 to 1:5, 2:1 to 1:2, 10:1 to 5:1, 5:1 to 2:1, 2:1 to 1:1, 1:1 to 1:2, 1:2 to 1:5, 1:5 to 1:10, or is greater than 10:1, or less than 1:1.

The above solubilizing agent can be further characterized according to the weight-average molecular weight of any polyethylene glycolyl component. For example, in certain embodiments, the polyethylene glycolyl has a weight-average molecular weight in the range of about 100 g/mol to about 3000 g/mol. In certain embodiments, the polyethylene glycolyl has a weight-average molecular weight in the range of about 200 g/mol to about 1500 g/mol. In certain embodiments, the polyethylene glycolyl has a weight-average molecular weight in the range of about 200 g/mol to about 1000 g/mol. In certain embodiments, the polyethylene glycolyl has a weight-average molecular weight in the range of about 300 g/mol to about 900 g/mol. In certain embodiments, the polyethylene glycolyl has a weight-average molecular weight in the range of about 500 g/mol to about 800 g/mol. In certain embodiments, the polyethylene glycolyl has a weight-average molecular weight in the range of about 600 g/mol to about 750 g/mol. In certain embodiments, the polyethylene glycolyl has a weight-average molecular weight in the range of about 600 g/mol to about 700 g/mol. In certain embodiments, the polyethylene glycolyl has a weight-average molecular weight of about 660 g/mol. In certain embodiments, the polyethylene glycolyl has a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

The above solubilizing agent can be further characterized according to the weight-average molecular weight of any polyethylene glycol component. For example, in certain embodiments, the polyethylene glycol has a weight-average molecular weight in the range of about 100 g/mol to about 3000 g/mol. In certain embodiments, the polyethylene glycol has a weight-average molecular weight in the range of about 200 g/mol to about 1500 g/mol. In certain embodiments, the polyethylene glycol has a weight-average molecular weight in the range of about 200 g/mol to about 1000 g/mol. In certain embodiments, the polyethylene glycol has a weight-average molecular weight in the range of about 300 g/mol to about 900 g/mol. In certain embodiments, the polyethylene glycol has a weight-average molecular weight in the range of about 500 g/mol to about 800 g/mol. In certain embodiments, the polyethylene glycol has a weight-average molecular weight in the range of about 600 g/mol to about 750 g/mol. In certain embodiments, the polyethylene glycol has a weight-average molecular weight in the range of about 600 g/mol to about 700 g/mol. In certain embodiments, the polyethylene glycol has a weight-average molecular weight of about 660 g/mol. In certain embodiments, the polyethylene glycol has a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

In yet other embodiments, any polyethylene glycol or polyethylene glycolyl each independently have a weight-average molecular weight in the range of about 100 g/mol to about 3000 g/mol. In certain embodiments, any polyethylene glycol or polyethylene glycolyl each independently have a weight-average molecular weight in the range of about 200 g/mol to about 1500 g/mol. In certain embodiments, any polyethylene glycol or polyethylene glycolyl each independently have a weight-average molecular weight in the range of about 200 g/mol to about 1000 g/mol. In certain embodiments, any polyethylene glycol or polyethylene glycolyl each independently have a weight-average molecular weight in the range of about 300 g/mol to about 900 g/mol. In certain embodiments, any polyethylene glycol or polyethylene glycolyl each independently have a weight-average molecular weight in the range of about 500 g/mol to about 800 g/mol. In certain embodiments, any polyethylene glycol or polyethylene glycolyl each independently have a weight-average molecular weight in the range of about 600 g/mol to about 750 g/mol. In certain embodiments, any polyethylene glycol or polyethylene glycolyl each independently have a weight-average molecular weight in the range of about 600 g/mol to about 700 g/mol. In certain embodiments, any polyethylene glycol or polyethylene glycolyl each independently have a weight-average molecular weight of about 660 g/mol. In certain embodiments, any polyethylene glycol or polyethylene glycolyl each independently have a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

Antioxidant

The formulation can be further characterized according to the antioxidant in the formulation. For example, in certain embodiments, the formulation comprises about 0.005% (w/w) to about 0.1% (w/w) of an antioxidant. In certain embodiments, the formulation comprises about 0.01% (w/w) of an antioxidant. In certain embodiments, the antioxidant is an organic compound. In certain embodiments, the antioxidant is a substituted phenol. In certain embodiments, the antioxidant is a phenolic antioxidant. In certain embodiments, the antioxidant is dibutylhydroxytoluene.

Chelating Agent

The formulation may optionally further comprise a chelating agent. Accordingly, in certain embodiments, the formulation further comprises a chelating agent. In certain embodiments, the formulation comprises about 0.001% (w/w) to about 0.5% (w/w) of a chelating agent. In certain embodiments, the formulation comprises about 0.01% (w/w) to about 0.05% (w/w) of a chelating agent. In certain embodiments, the formulation comprises about 0.025% (w/w) of a chelating agent.

Exemplary chelating agents include, but are not limited to, ethylenediaminetetraacetic acid (EDTA), citric acid, sorbitol, tartaric acid, phosphoric acid, salts of the foregoing, and the like. In certain embodiments, the chelating agent is an aliphatic amine compound containing at least two carboxylic acid groups. In certain embodiments, the chelating agent is ethylenediaminetetraacetic acid or a salt thereof.

In certain embodiments, the chelating agent is a metal ion chelating agent.

In certain embodiments, the combination of an antioxidant and a chelating agent (e.g., ethylenediaminetetraacetic acid or salt thereof) can increase the stability of an aqueous capsaicin formulation.

Buffer

The formulation may optionally further comprise a buffer. The buffer helps reduce changes in pH of the formulation over time and may provide improved drug stability. Exemplary buffers include, but are not limited to, sodium bicarbonate, sodium citrate, citric acid, sodium phosphate, pharmaceutically acceptable salts thereof, and combinations thereof. In certain embodiments, the buffer is an acetate salt, phosphate salt, citrate salt; corresponding acids of the foregoing; and combinations or mixtures thereof.

Accordingly, in certain embodiments, the formulation further comprises a buffer. In certain embodiments, the buffer comprises a carboxylic acid compound having a molecular weight less than 500 g/mol, a salt thereof, or a mixture thereof. In certain embodiments, the buffer comprises a $C_1$-$C_6$ alkanoic acid, a salt thereof, or a mixture thereof. In certain embodiments, the buffer comprises acetic acid, a salt of acetic acid, or a mixture thereof. In certain embodiments, the buffer is a mixture of alkali metal acetate and acetic acid. In certain embodiments, the buffer is a mixture of sodium acetate and acetic acid.

In certain embodiments, the formulation comprises about 0.1% (w/w) to about 1.0% (w/w) of a buffer. In certain embodiments, the formulation comprises about 0.5% (w/w) to about 0.8% (w/w) of a buffer. In certain embodiments, the formulation comprises about 0.7% (w/w) of a buffer. The amount of buffer may be alternatively characterized according to the molarity of the buffer in the formulation. Accordingly, in certain embodiments, the formulation comprises about 10 mM to about 100 mM of a buffer. In certain embodiments, the formulation comprises about 25 mM to about 75 mM of a buffer. In certain embodiments, the formulation comprises about 50 mM of a buffer (which preferably is a mixture of an alkali metal acetate and acetic acid, such as a mixture of sodium acetate and acetic acid).

Osmolality

The formulation may be further characterized according to the osmolality of the formulation. Formulations having an osmolality at or near the osmolality of a typical bodily fluid are referred to as isotonic. Formulations having an osmolality greater than the osmolality of a typical bodily fluid are referred to as hypertonic. Formulations having an osmolality less than the osmolality of a typical bodily fluid are referred to as hypotonic.

The osmolality of the formulation may be optionally adjusted by including a tonicity modifier. Accordingly, in certain embodiments, the formulation further comprises a tonicity modifier. In certain embodiments, the formulation comprises about 0.01% (w/w) to about 5% (w/w) of a tonicity modifier. In certain embodiments, the formulation comprises about 0.1% (w/w) to about 2% (w/w) of a tonicity modifier. In certain embodiments, the formulation comprises about 0.3% (w/w) to about 0.9% (w/w) of a tonicity modifier. In certain embodiments, the formulation comprises about 0.6% (w/w) of a tonicity modifier (which preferably is an alkali metal halide, such as sodium chloride).

In certain embodiments, the tonicity modifier is an alkali metal salt. In certain embodiments, the tonicity modifier is sodium chloride. In certain embodiments, the tonicity modifier is a monosaccharide. In certain embodiments, the tonicity modifier is dextrose.

Formulations may be characterized according to an osmolality threshold or range. For example, in certain embodiments, the formulation may have an osmolality of at least 200 mOsm/kg, 220 mOsm/kg, 240 mOsm/kg, 260 mOsm/kg, 280 mOsm/kg, 300 mOsm/kg, 325 mOsm/kg, 350 mOsm/kg, 375 mOsm/kg, 400 mOsm/kg, 425 mOsm/kg, 450 mOsm/kg, 500 mOsm/kg, 600 mOsm/kg, 700 mOsm/kg, 800 mOsm/kg, 900 mOsm/kg, or 1000 mOsm/kg. In certain embodiments, the formulation has an osmolality of at least 240 mOsm/kg. In certain embodiments, the formulation has an osmolality of at least 270 mOsm/kg.

In certain embodiments, the formulation has an osmolality in the range of from about 200 mOsm/kg to about 400 mOsm/kg, from about 240 mOsm/kg to about 350 mOsm/kg, from about 240 mOsm/kg to about 340 mOsm/kg, from about 270 mOsm/kg to about 340 mOsm/kg, from about 270 mOsm/kg to about 330 mOsm/kg, from about 270 mOsm/kg to about 310 mOsm/kg, from about 290 mOsm/kg to about 330 mOsm/kg, from about 280 mOsm/kg to about 300 mOsm/kg, or from about 300 mOsm/kg to about 320 mOsm/kg. In certain embodiments, the formulation has an osmolality in the range of from about 240 mOsm/kg to about 340 mOsm/kg. In certain other embodiments, the formulation has an osmolality in the range from about 270 mOsm/kg to about 330 mOsm/kg.

In certain embodiments, the formulation has osmolality of about 200 mOsm/kg, about 220 mOsm/kg, about 240 mOsm/kg, about 250 mOsm/kg, about 260 mOsm/kg, about 270 mOsm/kg, about 280 mOsm/kg, about 290 mOsm/kg, about 300 mOsm/kg, about 310 mOsm/kg, about 320 mOsm/kg, about 330 mOsm/kg, about 340 mOsm/kg, about 350 mOsm/kg, about 360 mOsm/kg, about 370 mOsm/kg, or about 380 mOsm/kg. In a preferred embodiment, the formulation has osmolality of about 290 mOsm/kg. In another preferred embodiment, the formulation has osmolality of about 310 mOsm/kg.

Amount of Water

The formulation may be further characterized according to the amount of water in the formulation. For example, in certain embodiments, the formulation comprises at least 95% (w/w) water. In certain embodiments, the formulation comprises at least 97% (w/w) water. In certain embodiments, the formulation comprises from about 95% (w/w) to about 99% (w/w) water. In certain embodiments, the formulation comprises from about 97% (w/w) to about 98% (w/w) water. In certain embodiments, the formulation comprises from about 93% (w/w) to about 96% (w/w) water.

pH of the Formulation

The formulation may be further characterized according to the pH of the formulation. For example, in certain embodiments, the formulation has a pH in the range of about 4 to about 7. In certain embodiments, the formulation has a pH in the range of about 5 to about 6. In certain embodiments, the formulation has a pH in the range of about 5.0 to about 5.2, about 5.2 to about 5.4, about 5.4 to about 5.6, or about 5.6 to about 5.8. In certain embodiments, the formulation has a pH of about 5.1, 5.2, 5.3, 5.4, 5.5, 5.6, 5.7, 5.8, or 5.9. In certain embodiments, the formulation has a pH of about 5.5.

Vanilloid Receptor Agonist

For a formulation containing a vanilloid receptor agonist, the formulation may be further characterized according to the amount and identity of the vanilloid receptor agonist. For example, in certain embodiments, the formulation comprises from about 0.001% (w/w) to about 5% (w/w), from about 0.001% (w/w) to about 1% (w/w), or from about 0.01% (w/w) to about 0.1% (w/w) of vanilloid receptor agonist. Exemplary vanilloid receptor agonists include, for example, capsaicin, resiniferatoxin, N-vanillylnonanamides, N-vanillylsulfonamides, N-vanillylureas, N-vanillylcarbamates, N-[(substituted phenyl)methyl]alkyamides, methylene substituted N-[(substituted phenyl)methyl]alkanamides, N-[(substituted phenyl)methyl]-cis-monosaturated alkenamides, N-[(substituted phenyl)methyl]diunsaturated amides, 3-hydroxyacetanilide, hydroxyphenylacetamides, pseudocapsaicin, dihydrocapsaicin, nordihydrocapsaicin anandamide, piperine, zingerone, warburganal, polygodial, aframodial, cinnamodial, cinnamosmolide, cinnamolide, isovelleral, scalaradial, ancistrodial, beta-acaridial, merulidial, and scutigeral.

Capsaicin

Capsaicin has the chemical name N-[(4-hydroxy-3-methoxyphenyl)methyl]-8-methylnon-6-enamide, and due to the presence of a carbon-carbon double bond can exist as a mixture of cis and trans isomers. The formulations may be characterized according to the isomeric purity of the capsaicin administered to the patient. For example, in certain embodiments, the capsaicin is a mixture of cis-capsaicin and trans-capsaicin that contains at least 95% by weight trans-capsaicin. In certain embodiments, the capsaicin is a mixture of cis-capsaicin and trans-capsaicin that contains at least 97% by weight trans-capsaicin. In certain embodiments, the capsaicin is a mixture of cis-capsaicin and trans-capsaicin that contains at least 98% by weight trans-capsaicin. In certain embodiments, the capsaicin is a mixture of cis-capsaicin and trans-capsaicin that contains at least 99% by weight trans-capsaicin. In certain other embodiments, the capsaicin is a mixture of cis-capsaicin and trans-capsaicin that contains at least 95% by weight cis-capsaicin. Accordingly, formulations described herein containing capsaicin can be characterized according to the isomeric purity of the capsaicin.

The isomeric purity of capsaicin may also be expressed according to the molar ratio of trans vs. cis isomer. Accordingly, in certain embodiments, the capsaicin is present as a mixture of trans and cis isomers, wherein the ratio of trans:cis isomers is at least 10:1. In certain embodiments, the ratio of trans:cis isomers is at least 15:1. In certain embodiments, the capsaicin consists essentially of the trans isomer.

The formulation may be further characterized according to the amount of capsaicin in the formulation. For example, in certain embodiments, the formulation comprises from about 0.03% (w/w) to about 0.15% (w/w) of capsaicin. In certain embodiments, the formulation comprises from about 0.03% (w/w) to about 0.07% (w/w) of capsaicin. In certain embodiments, the formulation comprises from about 0.01% (w/w) to about 0.03% (w/w) of capsaicin, 0.03% (w/w) to about 0.05% (w/w) of capsaicin, 0.05% (w/w) to about 0.07% (w/w) of capsaicin, 0.07% (w/w) to about 0.09% (w/w) of capsaicin, 0.09% (w/w) to about 0.11% (w/w) of capsaicin, or 0.11% (w/w) to about 0.13% (w/w) of capsaicin. In certain embodiments, the formulation comprises from about 0.04% (w/w) to about 0.06% (w/w) of capsaicin. In certain embodiments, the formulation comprises about 0.05% (w/w) of capsaicin. In certain embodiments, the formulation comprises from about 0.08% (w/w) to about 0.12% (w/w) of capsaicin. In certain embodiments, the formulation comprises from about 0.12% (w/w) to about 0.15% (w/w) of capsaicin, from about 0.15% (w/w) to about 0.18% (w/w) of capsaicin, from about 0.18% (w/w) to about 0.21% (w/w) of capsaicin, from about 0.21% (w/w) to about 0.25% (w/w) of capsaicin, or from about 0.25% (w/w) to about 0.3% (w/w) of capsaicin. In certain embodiments, the formulation comprises about 0.1% (w/w) of capsaicin.

Additional Pain-Relief Agent

The formulation may optionally contain a further pain-relief agent. For example, in certain embodiments, the formulation may further comprise a caine alkaloid. Exemplary caine alkaloids include lidocaine, dibucaine, bupivacaine, ropivacaine, etidocaine, tetracaine, procaine, chlorocaine, prilocaine, mepivacaine, xylocaine, 2-chloroprocaine, and pharmaceutically acceptable salts thereof. In certain embodiments, the formulation further comprises lidocaine, such as where the lidocaine is present in an amount of about 0.5% (w/w), 1.0% (w/w), 2.0% (w/w), 3.0% (w/w) or 4.0% (w/w) of the formulation, or in an amount ranging from about 0.5% (w/w) to about 2.0% (w/w), or about 2.0% (w/w) to about 4.0% (w/w) of the formulation.

Sterility of the Formulation

The formulation may be further characterized according to the sterility of the formulation and procedures used to sterilize the formulation. Accordingly, in certain embodiments, the formulation has a sterility assurance level of from about $10^{-1}$ to $10^{-3}$, about $10^{-3}$ to about $10^{-4}$, about $10^{-4}$ to about $10^{-5}$, about $10^{-5}$ to about $10^{-6}$, or about $10^{-6}$ to about $10^{-7}$, or a sterility assurance level that is more sterile than $10^{-7}$. In certain embodiments, the sterility assurance level that is more sterile than about $10^{-3}$, about $10^{-4}$, about $10^{-5}$, or about $10^{-6}$.

One method for improving the sterility of the formulation is to pass the formulation through a sterile filter. Such filter may be a 0.2 micron sterilizing filter.

Alternatively, the formulation may be subjected to sterilization by heating to above ambient temperature. Accordingly, in certain embodiments, the formulation may be characterized by the feature that the formulation has been subjected to sterilization by heating to above ambient temperature. In certain embodiments, the formulation may be characterized by the feature that the formulation has been subjected to sterilization by heating to a temperature in the range of from about 100° C. to about 135° C. In certain embodiments, the formulation has been subjected to sterilization by heating to a temperature in the range of from about 120° C. to about 125° C. In certain embodiments, the formulation has been subjected to sterilization conditions that achieve a $F_0$-value in the range of from about 6 to about 10. In certain embodiments, the formulation has been subjected to sterilization conditions that achieve a $F_0$-value of about 8. In certain embodiments, the formulation has been subjected to sterilization conditions that achieve a $F_0$-value in the range of from about 20 to about 30. In certain embodiments, the formulation has been subjected to sterilization conditions that achieve a $F_0$-value of about 25.

Exemplary Formulations

In certain embodiments, the formulation is one of the formulations in Table 1 below.

TABLE 1

| No. | Formulation |
|---|---|
| 1 | An aqueous, capsaicin injectable formulation, comprising:<br>a. about 0.03% (w/w) to about 0.3% (w/w) of capsaicin;<br>b. about 0.1% (w/w) to about 3% (w/w) of a solubilizing agent, wherein the solubilizing agent comprises (i) a polyethylene glycol ester of a ($C_{15}$-$C_{25}$) hydroxyalkanoic acid, (ii) a polyethylene glycol ester of a ($C_{15}$-$C_{25}$) hydroxyalkenoic acid, or (iii) a polyethylene glycol ester of a ($C_{15}$-$C_{25}$) alkanoic acid substituted by a —OC(O)($C_{14}$-$C_{24}$) hydroxyalkyl group;<br>c. about 0.001% (w/w) to about 2% (w/w) of an antioxidant; and<br>d. at least 92% (w/w) water; and<br>having a pH in the range of about 3 to about 8. |
| 2 | An aqueous, capsaicin injectable formulation, comprising:<br>a. about 0.04% (w/w) to about 0.06% (w/w) of capsaicin;<br>b. about 0.7% (w/w) to about 1.3% (w/w) of a solubilizing agent, wherein the solubilizing agent comprises (i) a polyethylene glycol ester of a ($C_{15}$-$C_{25}$) hydroxyalkanoic acid, or (ii) a polyethylene glycol ester of a ($C_{15}$-$C_{25}$) hydroxyalkenoic acid;<br>c. about 0.001% (w/w) to about 0.1% (w/w) of an antioxidant; and<br>d. at least 92% (w/w) water; and<br>having a pH in the range of about 4 to about 7. |
| 3 | An aqueous, capsaicin injectable formulation, comprising:<br>a. about 0.04% (w/w) to about 0.06% (w/w) of trans-capsaicin;<br>b. about 0.7% (w/w) to about 1.3% (w/w) of a solubilizing agent, wherein |

TABLE 1-continued

| No. | Formulation |
|---|---|
| | the solubilizing agent comprises (a) from about 60% (w/w) to about 80% (w/w) of a mixture of $(C_{17})$hydroxyalkyl-$CO_2$-(polyethylene glycolyl)-H and $(C_{17})$hydroxyalkyl-$CO_2$—$(C_{17})$alkylene-$CO_2$-(polyethylene glycolyl)-H, and (b) from about 20% (w/w) to about 40% (w/w) polyethylene glycol;<br>c. about 0.001% (w/w) to about 0.1% (w/w) of an antioxidant; and<br>d. at least 95% (w/w) water; and<br>having a pH in the range of about 4 to about 7. |
| 4 | An aqueous, capsaicin injectable formulation, comprising:<br>a. about 0.08% (w/w) to about 0.12% (w/w) of capsaicin;<br>b. about 1.8% (w/w) to about 2.2% (w/w) of a solubilizing agent, wherein the solubilizing agent comprises (i) a polyethylene glycol ester of a $(C_{15}$-$C_{25})$ hydroxyalkanoic acid, or (ii) a polyethylene glycol ester of a $(C_{15}$-$C_{25})$ hydroxyalkenoic acid;<br>c. about 0.001% (w/w) to about 0.1% (w/w) of an antioxidant; and<br>d. at least 93% (w/w) water; and<br>having a pH in the range of about 4 to about 7. |
| 5 | An aqueous, capsaicin injectable formulation, comprising:<br>a. about 0.08% (w/w) to about 0.12% (w/w) of capsaicin;<br>b. about 1.8% (w/w) to about 2.2% (w/w) of a solubilizing agent, wherein the solubilizing agent comprises (a) from about 60% (w/w) to about 80% (w/w) of a mixture of $(C_{17})$hydroxyalkyl-$CO_2$-(polyethylene glycolyl)-H and $(C_{17})$hydroxyalkyl-$CO_2$—$(C_{17})$alkylene-$CO_2$-(polyethylene glycolyl)-H, and (b) from about 20% (w/w) to about 40% (w/w) polyethylene glycol;<br>c. about 0.001% (w/w) to about 0.1% (w/w) of an antioxidant; and<br>d. at least 93% (w/w) water; and<br>having a pH in the range of about 4 to about 7. |

Exemplary more specific formulations are provided in Tables 2 and 3 below.

TABLE 2

| No. | Formulation |
|---|---|
| 1 | An aqueous, capsaicin injectable formulation, comprising:<br>a. about 0.04% (w/w) to about 0.06% (w/w) of capsaicin;<br>b. about 0.5% (w/w) to about 1.5% (w/w) of a solubilizing agent, wherein the solubilizing agent comprises 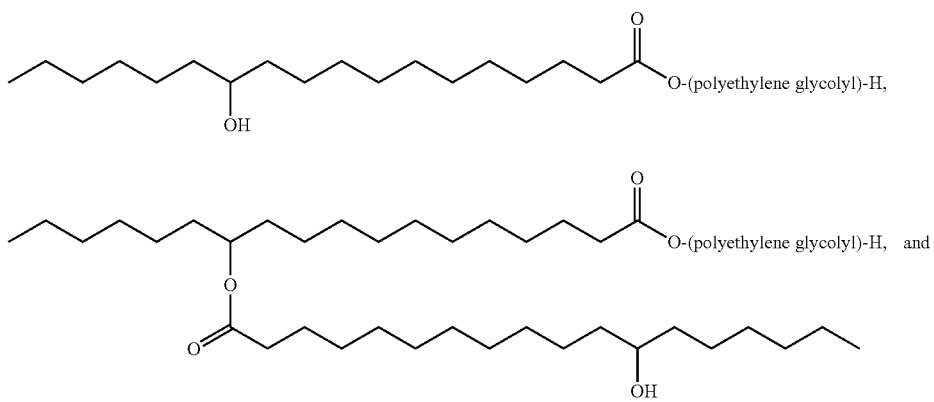 polyethylene glycol;<br>c. about 0.005% (w/w) to about 0.015% (w/w) of an antioxidant;<br>d. about 0.3% (w/w) to about 1% (w/w) of an alkali metal acetate;<br>e. about 0.01% (w/w) to about 0.05% (w/w) of a chelating agent;<br>f. about 0.3% (w/w) to about 0.9% (w/w) of a tonicity modifier;<br>g. at least 95% (w/w) water; and<br>having a pH in the range of about 5 to about 6. |
| 2 | An aqueous, capsaicin injectable formulation, comprising:<br>a. about 0.04% (w/w) to about 0.06% (w/w) of capsaicin;<br>b. about 0.8% (w/w) to about 1.2% (w/w) of a solubilizing agent, wherein the solubilizing agent comprises |

TABLE 2-continued

| No. | Formulation |
|---|---|

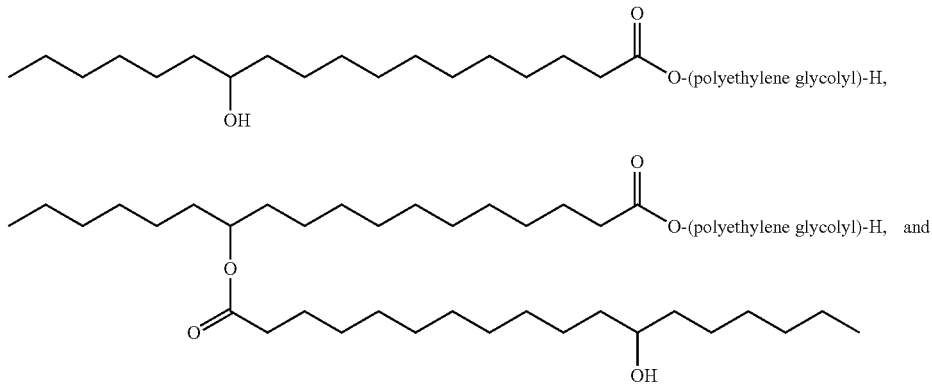

polyethylene glycol;
c. about 0.005% (w/w) to about 0.015% (w/w) of dibutylhydroxytoluene;
d. about 0.3% (w/w) to about 1% (w/w) of sodium acetate;
e. about 0.01% (w/w) to about 0.05% (w/w) of ethylenediaminetetraacetic acid or a salt thereof;
f. about 0.3% (w/w) to about 0.9% (w/w) of sodium chloride;
g. at least 95% (w/w) water; and
having a pH in the range of about 5 to about 6.

3  An aqueous, capsaicin injectable formulation, comprising:
   a. about 0.05% (w/w) of trans-capsaicin;
   b. about 1% (w/w) of a solubilizing agent, wherein the solubilizing agent comprises

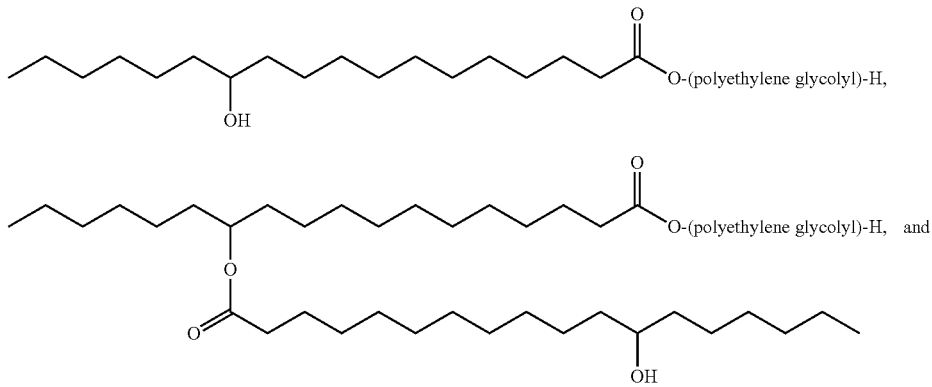

polyethylene glycol;
c. about 0.01% (w/w) dibutylhydroxytoluene;
d. about 0.5% (w/w) to about 0.8% (w/w) of sodium acetate;
e. about 0.01% (w/w) to about 0.05% (w/w) of ethylenediaminetetraacetic acid or a salt thereof;
f. about 0.3% (w/w) to about 0.9% (w/w) of sodium chloride;
g. at least 95% (w/w) water; and
having a pH in the range of about 5 to about 6.

4  An aqueous, capsaicin injectable formulation, comprising:
   a. about 0.08% (w/w) to about 0.12% (w/w) of capsaicin;
   b. about 1.5% (w/w) to about 2.5% (w/w) of a solubilizing agent, wherein the solubilizing agent comprises

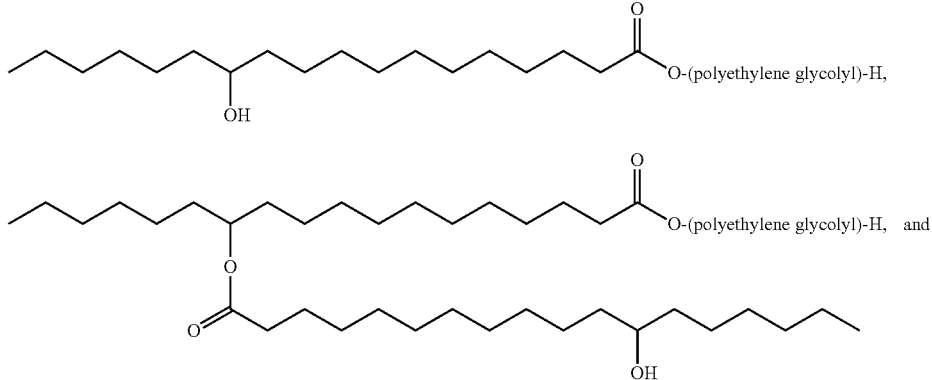

TABLE 2-continued

| No. | Formulation |
|---|---| polyethylene glycol;
   c. about 0.005% (w/w) to about 0.015% (w/w) of an antioxidant;
   d. about 0.1% (w/w) to about 1% (w/w) of an alkali metal carboxylate compound;
   e. about 0.01% (w/w) to about 0.5% (w/w) of a chelating agent;
   f. about 2% (w/w) to about 4% (w/w) of a tonicity modifier;
   g. at least 93% (w/w) water; and
      having a pH in the range of about 5 to about 6.

5   An aqueous, capsaicin injectable formulation, comprising:
   a. about 0.08% (w/w) to about 0.12% (w/w) of capsaicin;
   b. about 1.8% (w/w) to about 2.2% (w/w) of a solubilizing agent, wherein the solubilizing agent comprises

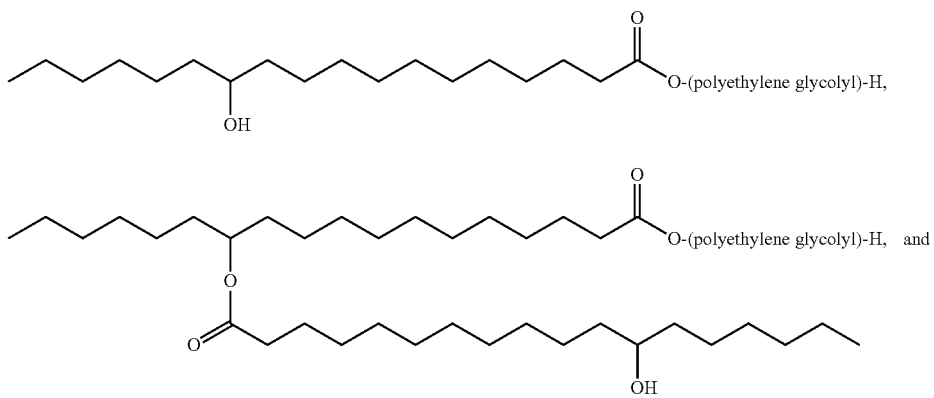

polyethylene glycol;
   c. about 0.005% (w/w) to about 0.015% (w/w) of an antioxidant;
   d. about 0.1% (w/w) to about 1% (w/w) of an alkali metal carboxylate compound;
   e. about 0.01% (w/w) to about 0.5% (w/w) of a chelating agent;
   f. about 2% (w/w) to about 4% (w/w) of a tonicity modifier;
   g. at least 93% (w/w) water; and
having a pH in the range of about 5 to about 6.

6   An aqueous, capsaicin injectable formulation, comprising:
   a. about 0.1% (w/w) of capsaicin;
   b. about 2% (w/w) of a solubilizing agent, wherein the solubilizing agent comprises

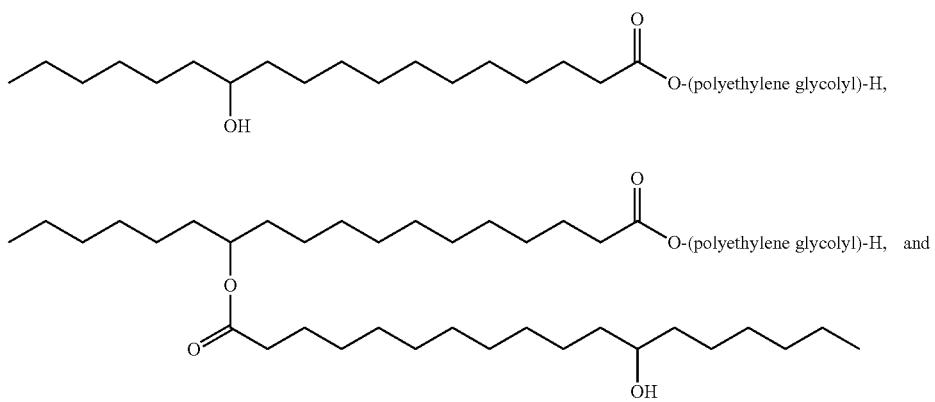

polyethylene glycol;
   c. about 0.005% (w/w) to about 0.015% (w/w) of an antioxidant;
   d. about 0.1% (w/w) to about 1% (w/w) of an alkali metal carboxylate compound;
   e. about 0.01% (w/w) to about 0.5% (w/w) of a chelating agent;
   f. about 2.5% (w/w) to about 3.5% (w/w) of a tonicity modifier;
   g. at least 93% (w/w) water; and
having a pH in the range of about 5 to about 6.

TABLE 3

| No. | Formulation |
|---|---|
| 1 | An aqueous, capsaicin injectable formulation, comprising:<br>a. about 0.1% (w/w) of capsaicin;<br>b. about 2% (w/w) of a solubilizing agent, wherein the solubilizing agent comprises<br>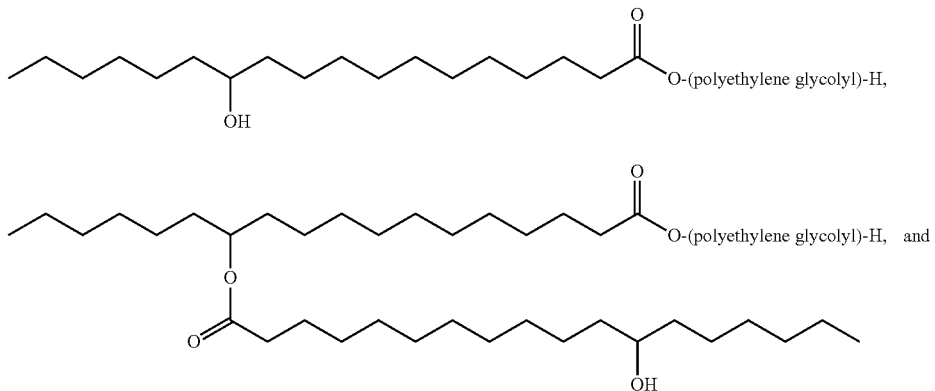<br>polyethylene glycol;<br>c. about 0.01% (w/w) of an antioxidant;<br>d. about 0.1% (w/w) to about 1% (w/w) of an alkali metal citrate salt;<br>e. about 0.1% (w/w) of a chelating agent;<br>f. about 3% (w/w) of a tonicity modifier; and<br>g. at least 93% (w/w) water. |
| 2 | An aqueous, capsaicin injectable formulation, comprising:<br>a. about 0.1% (w/w) of capsaicin;<br>b. about 2% (w/w) of a solubilizing agent, wherein the solubilizing agent comprises<br>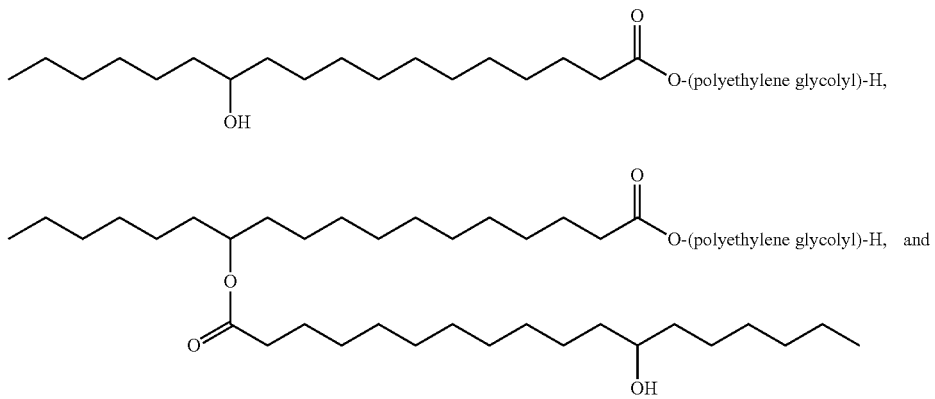<br>polyethylene glycol;<br>c. about 0.01% (w/w) of dibutylhydroxytoluene;<br>d. about 0.1% (w/w) to about 1% (w/w) of a disodium citrate salt;<br>e. about 0.1% (w/w) of ethylenediaminetetraacetic acid or a salt thereof;<br>f. about 3% (w/w) of dextrose;<br>g. at least 93% (w/w) water; and<br>   having a pH in the range of about 5 to about 6. |
| 3 | An aqueous, capsaicin injectable formulation, comprising:<br>a. about 0.1% (w/w) of trans-capsaicin;<br>b. about 2% (w/w) of a solubilizing agent, wherein the solubilizing agent that comprises<br>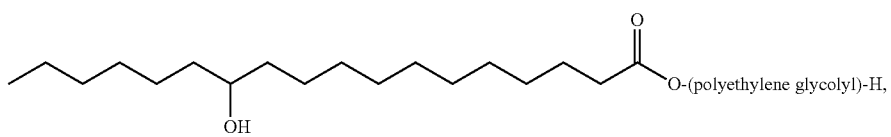 |

TABLE 3-continued

| No. | Formulation |
|---|---|

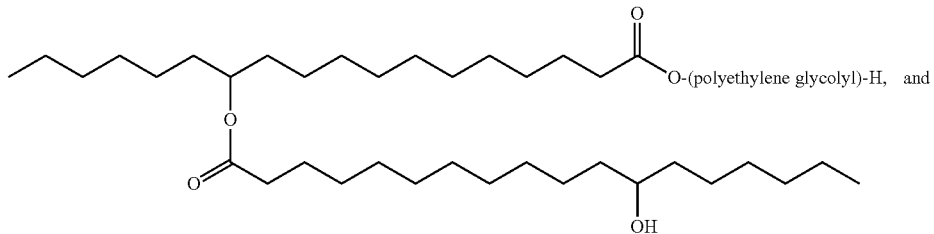

polyethylene glycol;
c. about 0.01% (w/w) of dibutylhydroxytoluene;
d. about 0.1% (w/w) to about 1% (w/w) of a disodium citrate salt;
e. about 0.1% (w/w) of ethylenediaminetetraacetic acid or a salt thereof;
f. about 3% (w/w) of dextrose;
g. at least 93% (w/w) water; and
    having a pH in the range of about 5 to about 6.

In yet other embodiments, the aqueous, capsaicin injectable formulation comprises (a) about 0.04% (w/w) to about 0.06% (w/w) of capsaicin; (b) about 0.5% (w/w) to about 1.5% (w/w) of a solubilizing agent, wherein the solubilizing agent comprises

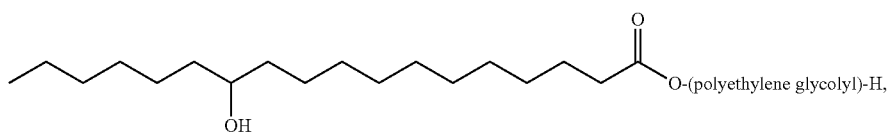

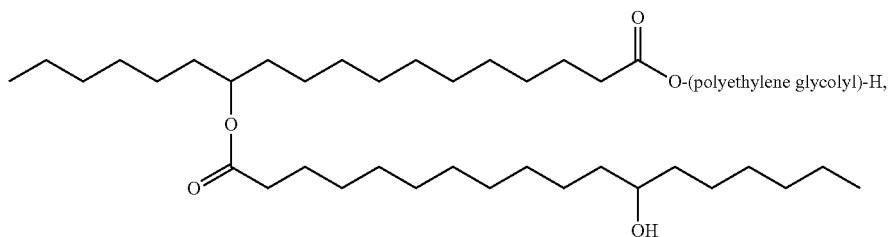

and polyethylene glycol; (c) about 0.005% (w/w) to about 0.015% (w/w) of an antioxidant; (d) about 0.2% (w/w) to about 1% (w/w) of an alkali metal acetate; (e) about 0.01% (w/w) to about 0.05% (w/w) of a chelating agent; (f) about 0.3% (w/w) to about 0.9% (w/w) of a tonicity modifier; and (g) at least 96% (w/w) water; and having a pH in the range of about 5 to about 6.

In other embodiments, the aqueous, capsaicin injectable formulation comprises (a) about 0.04% (w/w) to about 0.06% (w/w) of capsaicin; (b) about 0.8% (w/w) to about 1.2% (w/w) of a solubilizing agent, wherein the solubilizing agent comprises

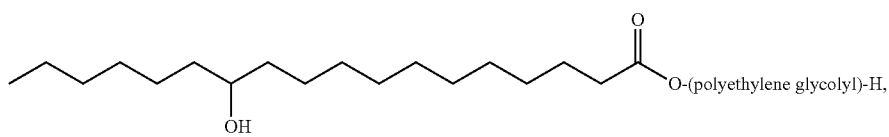

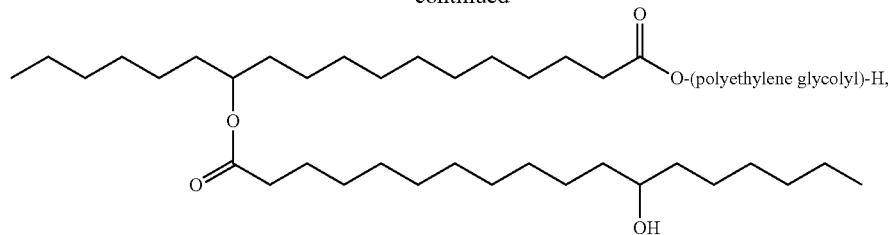

and polyethylene glycol; (c) about 0.005% (w/w) to about 0.015% (w/w) of dibutylhydroxytoluene; (d) about 0.2% (w/w) to about 1% (w/w) of sodium acetate; (e) about 0.01% (w/w) to about 0.05% (w/w) of ethylenediaminetetraacetic acid or a salt thereof; (f) about 0.3% (w/w) to about 0.9% (w/w) of sodium chloride; (g) at least 96% (w/w) water; and has a pH in the range of about 5 to about 6.

In other embodiments, the aqueous, capsaicin injectable formulation comprises
 a. about 0.04% (w/w) to about 0.06% (w/w) of capsaicin;
 b. about 0.8% (w/w) to about 1.2% (w/w) of a solubilizing agent, wherein the solubilizing agent comprises (a) about 70% (w/w) of a mixture of

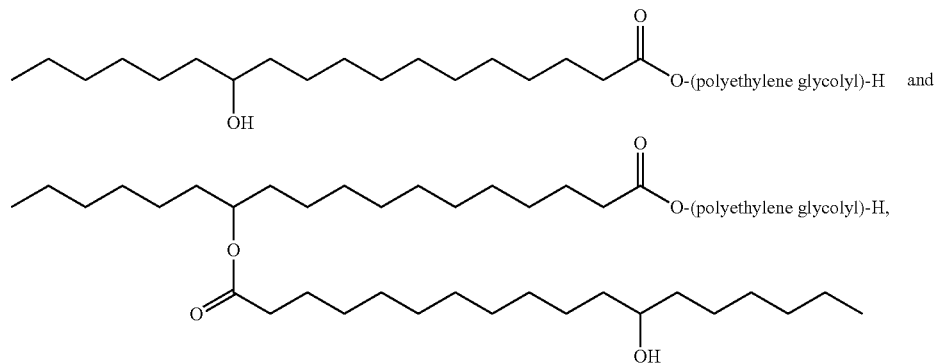

and (b) about 30% (w/w) polyethylene glycol;
 c. about 0.005% (w/w) to about 0.015% (w/w) of dibutylhydroxytoluene;
 d. about 0.2% (w/w) to about 1% (w/w) of sodium acetate;
 e. about 0.01% (w/w) to about 0.05% (w/w) of ethylenediaminetetraacetic acid or a salt thereof;
 f. about 0.3% (w/w) to about 0.9% (w/w) of sodium chloride;
 g. at least 96% (w/w) water; and
  having a pH in the range of about 5 to about 6.

In other embodiments, the aqueous, capsaicin injectable formulation comprises
 a. about 0.04% (w/w) to about 0.06% (w/w) of capsaicin;
 b. about 0.8% (w/w) to about 1.2% (w/w) of a solubilizing agent, wherein the solubilizing agent is a mixture of (a) about 70% (w/w) of a mixture of

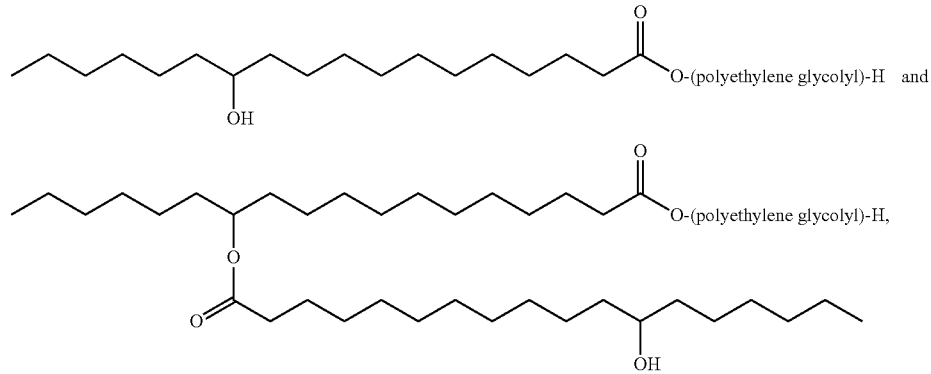

and (b) about 30% (w/w) polyethylene glycol;
  c. about 0.005% (w/w) to about 0.015% (w/w) of dibutylhydroxytoluene;
  d. about 0.2% (w/w) to about 1% (w/w) of sodium acetate;
  e. about 0.01% (w/w) to about 0.05% (w/w) of ethylenediaminetetraacetic acid or a salt thereof;
  f. about 0.3% (w/w) to about 0.9% (w/w) of sodium chloride;
  g. at least 96% (w/w) water; and
    having a pH in the range of about 5 to about 6.

In other embodiments, the aqueous, capsaicin injectable formulation comprises
  a. about 0.05% (w/w) of capsaicin;
  b. about 1% (w/w) of a solubilizing agent, wherein the solubilizing agent comprises and polyethylene glycol;
  c. about 0.005% (w/w) to about 0.015% (w/w) of dibutylhydroxytoluene;
  d. about 0.2% (w/w) to about 1% (w/w) of sodium acetate;
  e. about 0.01% (w/w) to about 0.05% (w/w) of ethylenediaminetetraacetic acid or a salt thereof;
  f. about 0.3% (w/w) to about 0.9% (w/w) of sodium chloride;
  g. at least 96% (w/w) water; and
    having a pH of about 5.5.

Each of the foregoing formulations may be further characterized according to the weight-average molecular weight of the polyethylene glycol component(s). Accordingly, in certain embodiments, the polyethylene glycol has a weight-average molecular weight in the range of about 200 g/mol to

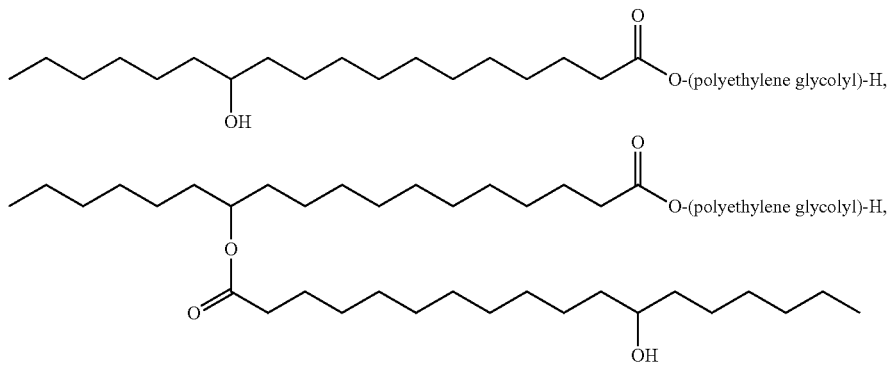

and polyethylene glycol;
  c. about 0.005% (w/w) to about 0.015% (w/w) of dibutylhydroxytoluene;
  d. about 0.2% (w/w) to about 1% (w/w) of sodium acetate;
  e. about 0.01% (w/w) to about 0.05% (w/w) of ethylenediaminetetraacetic acid or a salt thereof;
  f. about 0.3% (w/w) to about 0.9% (w/w) of sodium chloride;
  g. at least 96% (w/w) water; and
    having a pH of about 5.5.

In other embodiments, the aqueous, capsaicin injectable formulation comprises
  a. about 0.05% (w/w) of capsaicin;
  b. about 1% (w/w) of a solubilizing agent, wherein the solubilizing agent is a mixture of about 1500 g/mol. In certain embodiments, the polyethylene glycol has a weight-average molecular weight in the range of about 200 g/mol to about 1000 g/mol. In certain embodiments, the polyethylene glycol has a weight-average molecular weight in the range of about 300 g/mol to about 900 g/mol. In certain embodiments, the polyethylene glycol has a weight-average molecular weight in the range of about 500 g/mol to about 800 g/mol. In certain embodiments, the polyethylene glycol has a weight-average molecular weight in the range of about 600 g/mol to about 700 g/mol. In certain embodiments, the polyethylene glycol has a weight-average molecular weight in the range of about 100 g/mol to about 300 g/mol, about 300 g/mol to about 500 g/mol, about 500 g/mol to about 1000 g/mol, about 1000 g/mol to about

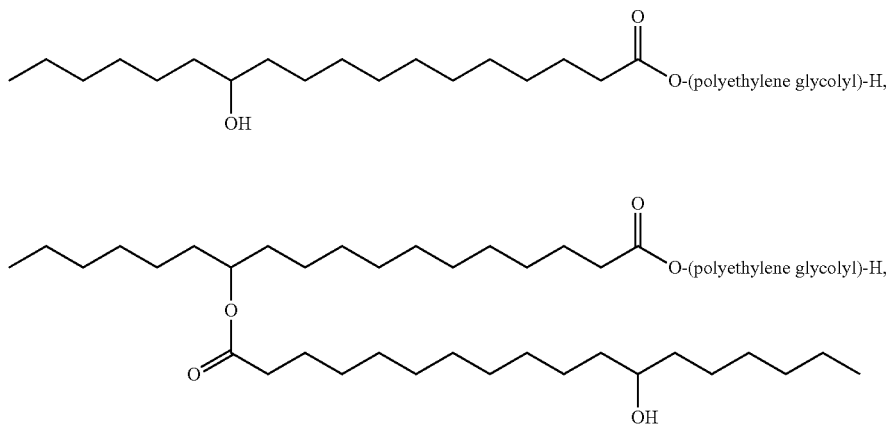

1500 g/mol, about 1500 g/mol to about 2000 g/mol, or about 2000 g/mol to about 2500 g/mol.

Additionally, each of the foregoing formulations may be further characterized according to the weight-average molecular weight of any polyethylene glycolyl component. For example, in certain embodiments, the polyethylene glycolyl has a weight-average molecular weight in the range of about 100 g/mol to about 3000 g/mol. In certain embodiments, the polyethylene glycolyl has a weight-average molecular weight in the range of about 200 g/mol to about 1500 g/mol. In certain embodiments, the polyethylene glycolyl has a weight-average molecular weight in the range of about 200 g/mol to about 1000 g/mol. In certain embodiments, the polyethylene glycolyl has a weight-average molecular weight in the range of about 300 g/mol to about 900 g/mol. In certain embodiments, the polyethylene glycolyl has a weight-average molecular weight in the range of about 500 g/mol to about 800 g/mol. In certain embodiments, the polyethylene glycolyl has a weight-average molecular weight in the range of about 600 g/mol to about 750 g/mol. In certain embodiments, the polyethylene glycolyl has a weight-average molecular weight in the range of about 600 g/mol to about 700 g/mol. In certain embodiments, the polyethylene glycolyl has a weight-average molecular weight of about 660 g/mol. In certain embodiments, the polyethylene glycolyl has a weight-average molecular weight in the range of about 100 g/mol to about 300 g/mol, about 300 g/mol to about 500 g/mol, about 500 g/mol to about 1000 g/mol, about 1000 g/mol to about 1500 g/mol, about 1500 g/mol to about 2000 g/mol, or about 2000 g/mol to about 2500 g/mol.

In yet other embodiments, the aqueous, capsaicin injectable formulation comprises (a) about 0.04% (w/w) to about 0.06% (w/w) of capsaicin; (b) about 0.5% (w/w) to about 1.5% (w/w) of a solubilizing agent, wherein the solubilizing agent comprises macrogol 15 hydroxystearate; (c) about 0.005% (w/w) to about 0.015% (w/w) of an antioxidant; (d) about 0.2% (w/w) to about 1% (w/w) of an alkali metal acetate; (e) about 0.01% (w/w) to about 0.05% (w/w) of a chelating agent; (f) about 0.3% (w/w) to about 0.9% (w/w) of a tonicity modifier; and (g) at least 96% (w/w) water; and having a pH in the range of about 5 to about 6. In other embodiments, the aqueous, capsaicin injectable formulation comprises (a) about 0.04% (w/w) to about 0.06% (w/w) of capsaicin; (b) about 0.8% (w/w) to about 1.2% (w/w) of a solubilizing agent, wherein the solubilizing agent comprises macrogol 15 hydroxystearate; (c) about 0.005% (w/w) to about 0.015% (w/w) of dibutylhydroxytoluene; (d) about 0.2% (w/w) to about 1% (w/w) of sodium acetate; (e) about 0.01% (w/w) to about 0.05% (w/w) of ethylenediaminetetraacetic acid or a salt thereof; (f) about 0.3% (w/w) to about 0.9% (w/w) of sodium chloride; (g) at least 96% (w/w) water; and has a pH in the range of about 5 to about 6; wherein the formulation has been subjected to sterilization procedures (e.g., sterilization by heating to above ambient temperature (e.g., autoclave sterilization)). In other embodiments, the aqueous, capsaicin injectable formulation comprises (a) about 0.05% (w/w) of capsaicin; (b) about 1% (w/w) of a solubilizing agent, wherein the solubilizing agent comprises macrogol 15 hydroxystearate; (c) about 0.005% (w/w) to about 0.015% (w/w) of dibutylhydroxytoluene; (d) about 0.2% (w/w) to about 1% (w/w) of sodium acetate; (e) about 0.01% (w/w) to about 0.05% (w/w) of ethylenediaminetetraacetic acid or a salt thereof; (f) about 0.3% (w/w) to about 0.9% (w/w) of sodium chloride; (g) at least 96% (w/w) water; and having a pH of about 5.5; wherein optionally the formulation has been subjected to sterilization procedures (e.g., sterilization by heating to above ambient temperature (e.g., autoclave sterilization)).

Exemplary more specific formulations are provided in Tables 4 and 5 below.

TABLE 4

| No. | Formulation |
|---|---|
| 1 | An aqueous, capsaicin injectable formulation, comprising:<br>a. about 0.05% (w/w) of trans-capsaicin;<br>b. about 1% (w/w) of a solubilizing agent, wherein the solubilizing agent is a mixture of<br><br>[chemical structures: a long-chain hydroxy fatty acid ester with O-(polyethylene glycolyl)-H, and a diester structure with O-(polyethylene glycolyl)-H]<br><br>polyethylene glycol; wherein the polyethylene glycolyl has a weight average molecular weight of about 660 g/mol;<br>c. about 0.01% (w/w) dibutylhydroxytoluene;<br>d. about 0.68% (w/w) of sodium acetate or a mixture of sodium acetate and acetic acid;<br>e. about 0.025% (w/w) of ethylenediaminetetraacetic acid or a salt thereof;<br>f. about 0.6% (w/w) of sodium chloride;<br>g. at least 97% (w/w) water; and<br>having a pH of about 5.5. |
| 2 | An aqueous, capsaicin injectable formulation, comprising:<br>a. 0.05% (w/w) of trans-capsaicin;<br>b. 1% (w/w) of a solubilizing agent, wherein the solubilizing agent is a mixture of |

TABLE 4-continued

| No. | Formulation |
|---|---|

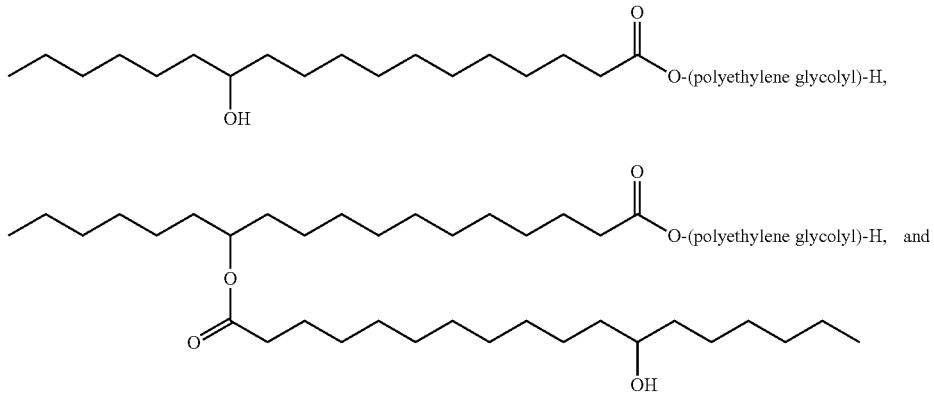

polyethylene glycol; wherein the polyethylene glycolyl has a weight average molecular weight of about 660 g/mol;
    c. 0.01% (w/w) dibutylhydroxytoluene;
    d. 0.68% (w/w) of sodium acetate or a mixture of sodium acetate and acetic acid;
    e. 0.025% (w/w) of ethylenediaminetetraacetic acid or a salt thereof;
    f. 0.6% (w/w) of sodium chloride;
    g. at least 97% (w/w) water; and
having a pH of 5.5.

3  An aqueous, capsaicin injectable formulation, comprising:
    a. about 0.05% (w/w) of trans-capsaicin;
    b. about 1% (w/w) of a solubilizing agent, wherein the solubilizing agent is a mixture of

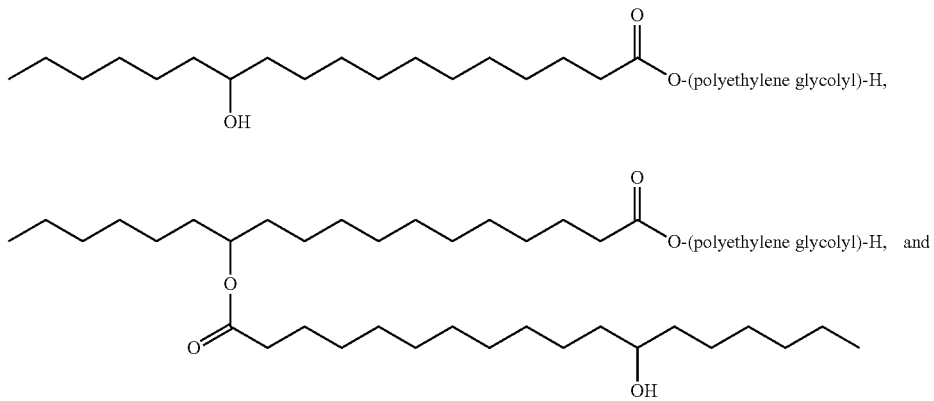

polyethylene glycol; wherein the polyethylene glycolyl has a weight average molecular weight of about 660 g/mol;
    c. about 0.01% (w/w) dibutylhydroxytoluene;
    d. about 0.34% (w/w) of sodium acetate or a mixture of sodium acetate and acetic acid;
    e. about 0.025% (w/w) of ethylenediaminetetraacetic acid or a salt thereof;
    f. about 0.75% (w/w) of sodium chloride;
    g. at least 97% (w/w) water; and
having a pH of about 5.5.

4  An aqueous, capsaicin injectable formulation, comprising:
    a. 0.05% (w/w) of trans-capsaicin;
    b. 1% (w/w) of a solubilizing agent, wherein the solubilizing agent is a mixture of

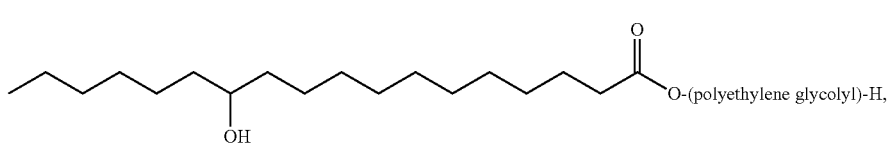

TABLE 4-continued

| No. | Formulation |
|---|---|

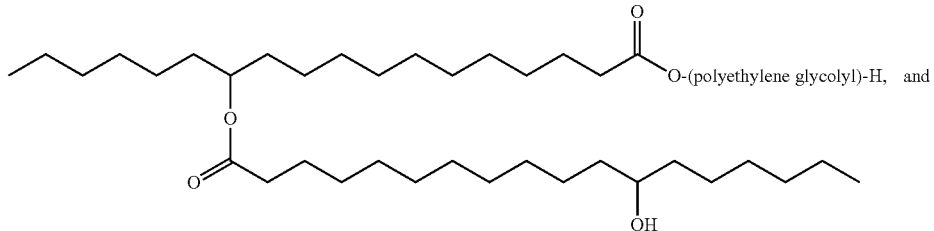

polyethylene glycol; wherein the polyethylene glycolyl has a weight average molecular weight of about 660 g/mol;

c. 0.01% (w/w) dibutylhydroxytoluene;

d. 0.34% (w/w) of sodium acetate or a mixture of sodium acetate and acetic acid;

e. 0.025% (w/w) of ethylenediaminetetraacetic acid or a salt thereof;

f. 0.75% (w/w) of sodium chloride;

g. at least 97% (w/w) water; and having a pH of 5.5.

TABLE 5

| No. | Formulation |
|---|---|
| 1 | An aqueous, capsaicin injectable formulation, comprising:<br>a. about 0.05% (w/w) of trans-capsaicin;<br>b. about 1% (w/w) of a solubilizing agent, wherein the solubilizing agent is a mixture of<br>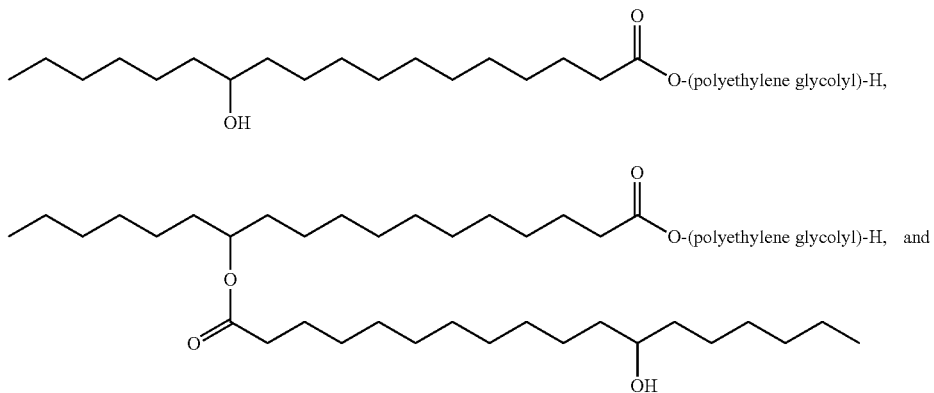<br>polyethylene glycol; wherein the polyethylene glycolyl has a weight average molecular weight of about 660 g/mol;<br>c. about 0.01% (w/w) dibutylhydroxytoluene;<br>d. about 0.22% (w/w) of sodium citrate or a mixture of sodium citrate and citric acid;<br>e. about 0.025% (w/w) of ethylenediaminetetraacetic acid or a salt thereof;<br>f. about 0.8% (w/w) of sodium chloride;<br>g. at least 97% (w/w) water; and<br>having a pH of about 5.5. |
| 2 | An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>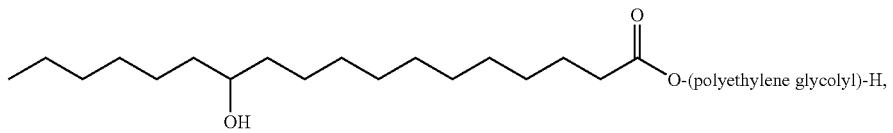 |

TABLE 5-continued

| No. | Formulation |
|---|---|

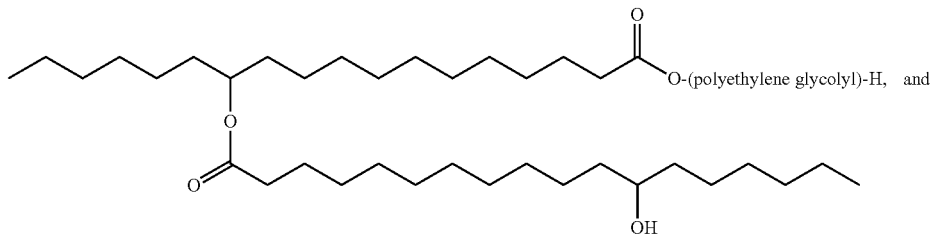

polyethylene glycol; wherein the polyethylene glycolyl has a weight average molecular weight of about 660 g/mol;
c. 0.01% (w/w) dibutylhydroxytoluene;
d. 0.22% (w/w) of sodium citrate or a mixture of sodium citrate and citric acid;
e. 0.025% (w/w) of ethylenediaminetetraacetic acid or a salt thereof;
f. 0.8% (w/w) of sodium chloride;
g. at least 97% (w/w) water; and
having a pH of 5.5.

3  An aqueous, capsaicin injectable formulation, comprising:
a. about 1% (w/w) of trans-capsaicin;
b. about 2% (w/w) of a solubilizing agent, wherein the solubilizing agent is a mixture of

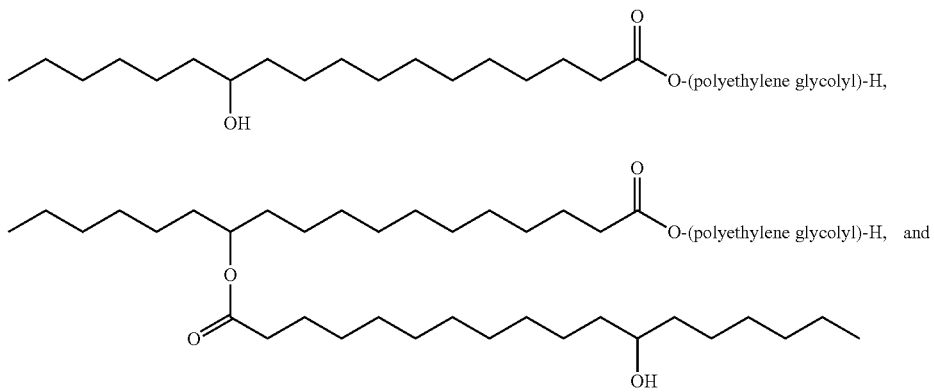

polyethylene glycol; wherein the polyethylene glycolyl has a weight average molecular weight of about 660 g/mol;
c. about 0.01% (w/w) dibutylhydroxytoluene;
d. about 20 mM of sodium citrate or a mixture of sodium citrate and citric acid;
e. about 0.1% (w/w) of ethylenediaminetetraacetic acid or a salt thereof;
f. about 3.15% (w/w) of dextrose;
g. at least 93% (w/w) water; and
having a pH of about 5 to about 6.

4  An aqueous, capsaicin injectable formulation, comprising:
a. 1% (w/w) of trans-capsaicin;
b. 2% (w/w) of a solubilizing agent, wherein the solubilizing agent is a mixture of

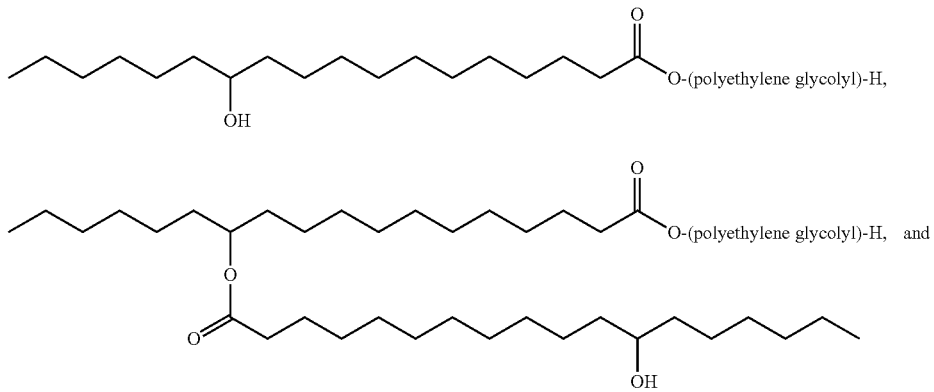

polyethylene glycol; wherein the polyethylene glycolyl has a weight average molecular weight of about 660 g/mol;
c. 0.01% (w/w) dibutylhydroxytoluene;
d. 20 mM of sodium citrate or a mixture of sodium citrate and citric acid;

TABLE 5-continued

| No. | Formulation |
|---|---|
| | e. 0.1% (w/w) of ethylenediaminetetraacetic acid or a salt thereof; |
| | f. 3.15% (w/w) of dextrose; |
| | g. at least 93% (w/w) water; and |
| | having a pH of about 5 to about 6. |

In certain embodiments, the formulation is one of the formulations described in Tables 1-5 above, wherein the formulation has an osmolality in the range of from about 240 mOsm/kg to about 340 mOsm/kg. In certain embodiments, the formulation is one of the formulations described in Tables 1-5 above, wherein the formulation has an osmolality in the range from about 270 mOsm/kg to about 330 mOsm/kg.

Stability of the Aqueous Capsaicin Injectable Formulations

A formulation containing capsaicin can be further characterized according to the stability of the formulation upon storage. For example, in certain embodiments, the formulation is characterized by the feature that less than 1% of the capsaicin degrades upon storage at 25° C. for 24 weeks. In certain other embodiments, less than 0.5% of the capsaicin degrades upon storage at 25° C. for 24 weeks. In certain other embodiments, less than 0.1% of the capsaicin degrades upon storage at 25° C. for 24 weeks. In certain other embodiments, less than 1% of the capsaicin degrades upon storage at 40° C. for 24 weeks. In certain other embodiments, less than 0.5% of the capsaicin degrades upon storage at 40° C. for 24 weeks.

Amount of Capsaicin-Dimer in an Aqueous Capsaicin Injectable Formulation

A formulation containing capsaicin can be further characterized according to the amount of any impurities in the formulation, such as the amount of capsaicin-dimer having the following formula:

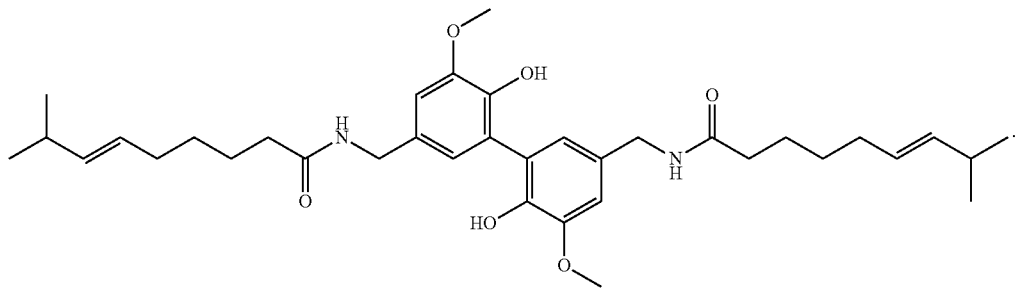 [SMILES: COc1cc(CNC(=O)CCCC/C=C/C(C)C)cc(-c2cc(CNC(=O)CCCC/C=C/C(C)C)cc(OC)c2O)c1O]

Accordingly, in certain embodiments, the formulation is characterized by the feature that it contains less than 3% (w/w) of capsaicin-dimer having the following structure:

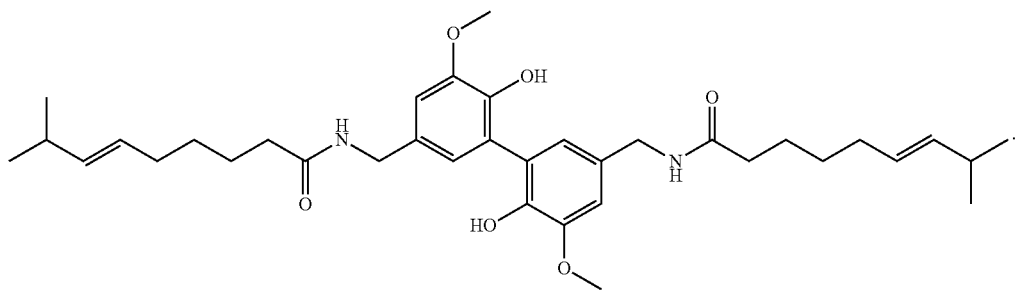 [SMILES: COc1cc(CNC(=O)CCCC/C=C/C(C)C)cc(-c2cc(CNC(=O)CCCC/C=C/C(C)C)cc(OC)c2O)c1O]

In certain other embodiments, the formulation contains less than 2% (w/w) of the capsaicin-dimer. In certain other embodiments, the formulation contains less than 1% (w/w) of the capsaicin-dimer. In certain other embodiments, the formulation contains less than 0.6% (w/w) of the capsaicin-dimer.

In certain other embodiments, upon storage at 25° C. for 12 weeks, the formulation contains less than 3% (w/w) of capsaicin-dimer having the following structure:

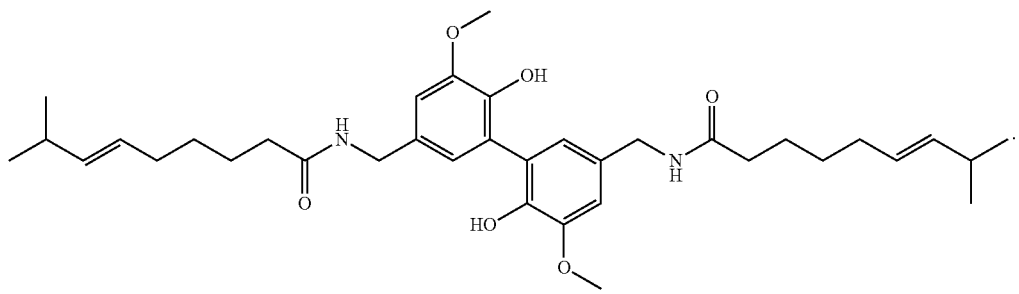 [SMILES: COc1cc(CNC(=O)CCCC/C=C/C(C)C)cc(-c2cc(CNC(=O)CCCC/C=C/C(C)C)cc(OC)c2O)c1O]

In certain other embodiments, upon storage at 25° C. for 12 weeks, the formulation contains less than 2% (w/w) of capsaicin-dimer. In certain other embodiments, upon storage at 25° C. for 24 weeks, the formulation contains less than 1% (w/w) of the capsaicin-dimer. In certain other embodiments, upon storage at 25° C. for 24 weeks, the formulation contains less than 0.6% (w/w) of the capsaicin-dimer.

Amount of Substituted 1,1'-Biphenyl Compound in an Aqueous Capsaicin Injectable Formulation A formulation containing capsaicin can be further characterized according to the amount of substituted 1,1'-biphenyl compound having the following structure:

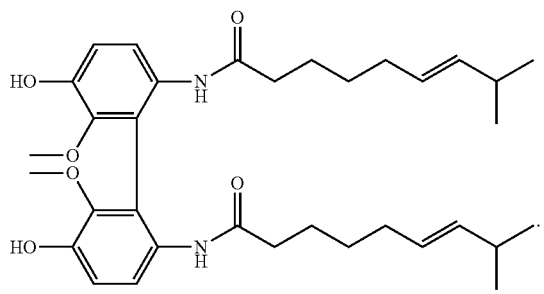 [SMILES: COc1c(O)ccc(NC(=O)CCCC/C=C/C(C)C)c1-c1c(NC(=O)CCCC/C=C/C(C)C)ccc(O)c1OC]

In certain embodiments, the formulation contains less than 2% (w/w) of the substituted 1,1'-biphenyl compound. In certain embodiments, the formulation contains less than 1% (w/w) of the substituted 1,1'-biphenyl compound.

In certain other embodiments, upon storage at 25° C. for 12 weeks, the formulation contains less than 3% (w/w) of the aforementioned substituted 1,1'-biphenyl compound. In certain other embodiments, upon storage at 25° C. for 12 weeks, the formulation contains less than 2% (w/w) of the substituted 1,1'-biphenyl compound. In certain other embodiments, upon storage at 25° C. for 24 weeks, the formulation contains less than 1% (w/w) of the substituted 1,1'-biphenyl compound. In certain other embodiments, upon storage at 25° C. for 24 weeks, the formulation contains less than 0.6% (w/w) of substituted 1,1'-biphenyl compound.

Amount of Substituted 1,1'-Bibenzyl Compound in an Aqueous Capsaicin Injectable Formulation A formulation containing capsaicin can be further characterized according to the amount of substituted 1,1'-bibenzyl compound having the following structure:

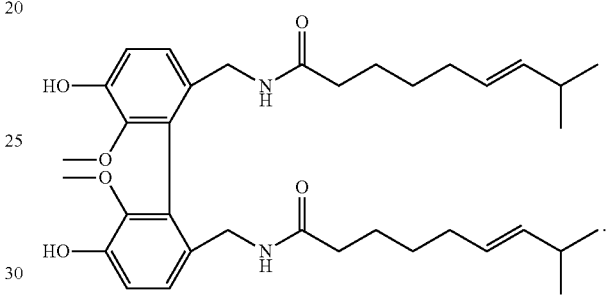

In certain embodiments, the formulation contains less than 2% (w/w) of the substituted 1,1'-bibenzyl compound. In certain embodiments, the formulation contains less than 1% (w/w) of the substituted 1,1'-bibenzyl compound. In certain embodiments, the formulation contains less than 0.5% (w/w) of the substituted 1,1'-bibenzyl compound. In certain embodiments, the formulation contains less than 0.1% (w/w) of the substituted 1,1'-bibenzyl compound. In certain embodiments, the formulation contains less than 0.05% (w/w) of the substituted 1,1'-bibenzyl compound.

In certain other embodiments, upon storage at 25° C. for 12 weeks, the formulation contains less than 2% (w/w) of the aforementioned substituted 1,1'-bibenzyl compound. In certain other embodiments, upon storage at 25° C. for 12 weeks, the formulation contains less than 1% (w/w) of the substituted 1,1'-bibenzyl compound. In certain other embodiments, upon storage at 25° C. for 24 weeks, the formulation contains less than 0.5% (w/w) of the substituted 1,1'-bibenzyl compound. In certain other embodiments, upon storage at 25° C. for 24 weeks, the formulation contains less than 0.1% (w/w) of substituted 1,1'-bibenzyl compound.

Amount of Substituted 1,2'-Bibenzyl Compound in an Aqueous Capsaicin Injectable Formulation A formulation containing capsaicin can be further characterized according to the amount of substituted 1,2'-bibenzyl compound having the following structure:

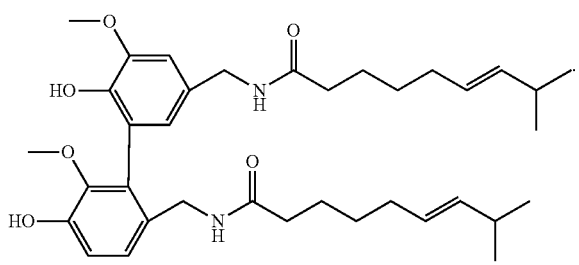 [SMILES: COc1cc(CNC(=O)CCCC/C=C/C(C)C)cc(-c2c(CNC(=O)CCCC/C=C/C(C)C)ccc(O)c2OC)c1O]

In certain embodiments, the formulation contains less than 2% (w/w) of the substituted 1,2'-bibenzyl compound. In certain embodiments, the formulation contains less than 1% (w/w) of the substituted 1,2'-bibenzyl compound. In certain embodiments, the formulation contains less than 0.5% (w/w) of the substituted 1,2'-bibenzyl compound. In certain embodiments, the formulation contains less than 0.1% (w/w) of the substituted 1,2'-bibenzyl compound. In certain embodiments, the formulation contains less than 0.05% (w/w) of the substituted 1,1'-bibenzyl compound.

In certain other embodiments, upon storage at 25° C. for 12 weeks, the formulation contains less than 2% (w/w) of the aforementioned substituted 1,2'-bibenzyl compound. In certain other embodiments, upon storage at 25° C. for 12 weeks, the formulation contains less than 1% (w/w) of the substituted 1,2'-bibenzyl compound. In certain other embodiments, upon storage at 25° C. for 24 weeks, the formulation contains less than 0.5% (w/w) of the substituted 1,2'-bibenzyl compound. In certain other embodiments, upon storage at 25° C. for 24 weeks, the formulation contains less than 0.1% (w/w) of substituted 1,2'-bibenzyl compound.

Amount of 5-Oxo-Capsaicin in an Aqueous Capsaicin Injectable Formulation

A formulation containing capsaicin can be further characterized according to the amount of 5-oxo-capsaicin having the following structure:

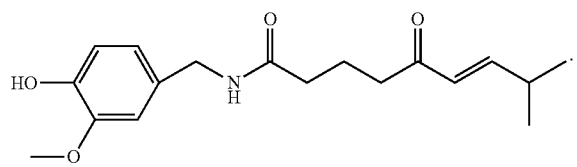 [SMILES: COc1cc(CNC(=O)CCCC(=O)/C=C/C(C)C)ccc1O]

In certain embodiments, the formulation contains less than 2% (w/w) of 5-oxo-capsaicin. In certain embodiments, the formulation contains less than 1% (w/w) of 5-oxo-capsaicin. In certain embodiments, the formulation contains less than 0.5% (w/w) of 5-oxo-capsaicin. In certain embodiments, the formulation contains less than 0.1% (w/w) of 5-oxo-capsaicin. In certain embodiments, the formulation contains less than 0.05% (w/w) of 5-oxo-capsaicin.

In certain other embodiments, upon storage at 25° C. for 12 weeks, the formulation contains less than 2% (w/w) of 5-oxo-capsaicin. In certain other embodiments, upon storage at 25° C. for 12 weeks, the formulation contains less than 1% (w/w) of 5-oxo-capsaicin. In certain other embodiments, upon storage at 25° C. for 24 weeks, the formulation contains less than 0.5% (w/w) of 5-oxo-capsaicin. In certain other embodiments, upon storage at 25° C. for 24 weeks, the formulation contains less than 0.1% (w/w) of 5-oxo-capsaicin.

Amount of Particulate Matter in an Aqueous Capsaicin Injectable Formulation

Formulations herein can be further characterized according to the amount of particulate matter present in the formulation. Accordingly, in certain embodiments, a 2 mL aliquot of the formulation contains less than 6000 particles having an average diameter of ≥10 μm. In certain embodiments, a 2 mL aliquot of the formulation contains less than 3000, 2000, 1000, 750, 500, 400, 300, 200, or 100 particles having an average diameter of ≥10 μm. In certain embodiments, a 2 mL aliquot of the formulation contains less than 1500 particles having an average diameter of ≥10 μm. In certain embodiments, a 2 mL aliquot of the formulation contains less than 1000 particles having an average diameter of ≥10 μm.

Further, in certain embodiments, a 2 mL aliquot of the formulation contains less than 1000 particles having an average diameter of ≥25 μm. In certain embodiments, a 2 mL aliquot of the formulation contains less than 750, 700, 600, 500, 400, 300, 200, 100, 75, 50, 40, 30, 25, 20, 15, or 10 particles having an average diameter of ≥25 μm. In certain embodiments, a 2 mL aliquot of the formulation contains less than 600 particles having an average diameter of ≥25 μm. In certain embodiments, a 2 mL aliquot of the formulation contains less than 15 particles having an average diameter of ≥25 μm.

Further, in certain embodiments, a 2 mL aliquot of the formulation that has been stored at 25° C. and 60% Relative Humidity for a duration of 3 months contains less than 6000 particles having an average diameter of ≥10 μm. In certain embodiments, a 2 mL aliquot of the formulation that has been stored at 25° C. and 60% Relative Humidity for a duration of 3 months contains less than 3000, 2000, 1000, 750, 500, 400, 300, 200, or 100 particles having an average diameter of ≥10 μm. In certain embodiments, a 2 mL aliquot of the formulation that has been stored at 25° C. and 60% Relative Humidity for a duration of 3 months contains less than 1500 particles having an average diameter of ≥10 μm. In certain embodiments, a 2 mL aliquot of the formulation that has been stored at 25° C. and 60% Relative Humidity for a duration of 3 months contains less than 1000 particles having an average diameter of ≥10 μm.

Further, in certain embodiments, a 2 mL aliquot of the formulation that has been stored at 25° C. and 60% Relative Humidity for a duration of 3 months contains less than 1000 particles having an average diameter of ≥25 μm. In certain embodiments, a 2 mL aliquot of the formulation that has been stored at 25° C. and 60% Relative Humidity for a duration of 3 months contains less than 750, 700, 600, 500, 400, 300, 200, 100, 75, 50, 40, 30, 25, 20, 15, or 10 particles having an average diameter of ≥25 μm. In certain embodiments, a 2 mL aliquot of the formulation that has been stored at 25° C. and 60% Relative Humidity for a duration of 3 months contains less than 600 particles having an average diameter of ≥25 μm. In certain embodiments, a 2 mL aliquot of the formulation that has been stored at 25° C. and 60% Relative Humidity for a duration of 3 months contains less than 15 particles having an average diameter of ≥25 μm.

Amount of Optional Other Components in the Injectable Formulations

Formulations herein can be further characterized according to the amount of optional other components. For example, in certain embodiments, the formulation contains less than 0.1% (w/w) of any polysorbate (e.g., polysorable 20 or polysorbate 80). In certain embodiments, the formulation does not contain any polysorbate. In certain embodiments, the formulation contains less than 0.1% (w/w) of any polysorbate, cyclodextrin, or alcohol. In certain embodiments, the formulation does not contain any polysorbate, cyclodextrin, or alcohol.

In yet other embodiments, other than said solubilizing agent, the formulation contains less than 0.1% (w/w) of any polymer, oligomer-containing agent, or agent that improves the solubility of capsaicin. In yet other embodiments, other than said solubilizing agent, the formulation does not contain any polymer, oligomer-containing agent, or agent that improves the solubility of capsaicin. In yet other embodiments, the formulation contains less than 0.1% (w/w) of any cyclodextrin, cellulose, alcohol (e.g., menthol), or hyaluronic acid. In yet other embodiments, the formulation does not contain any cyclodextrin, cellulose, alcohol (e.g., menthol), or hyaluronic acid.

In certain embodiments, the formulation contains less than 0.1% (w/w) of any phospholipid, polysaccharide, protein polymer, cellulose, sorbitan ester, or histidine. In certain embodiments, the formulation does not contain of any phospholipid, polysaccharide, protein polymer, cellulose, sorbitan ester, or histidine. In certain embodiments, the formulation contains less than 0.1% (w/w) of any polyvinylpyrrolidone polymer. In certain embodiments, the formulation does not contain any polyvinylpyrrolidone polymer.

In certain embodiments, the formulation contains less than 0.5% (w/w) of any polyalkylene glycol (e.g., polyethylene glycol) polymer. In certain embodiments, the formulation contains less than 0.3% (w/w), 0.25% (w/w), 0.2% (w/w), 0.15% (w/w), 0.1% (w/w), 0.05% (w/w) 0.01% (w/w) of any polyalkylene glycol (e.g., polyethylene glycol) polymer.

In certain embodiments, the formulation contains less than 0.5% (w/w) of any surfactant. In certain embodiments, the formulation contains less than 0.3% (w/w), 0.25% (w/w), 0.2% (w/w), 0.15% (w/w), 0.1% (w/w), 0.05% (w/w) 0.01% (w/w) of any surfactant. In certain embodiments, but for any component of the formulation named in the description of the formulation that would qualify as a surfactant, the formulation does not contain any other agent that is a surfactant.

III. Unit Dosage Forms

The invention provides a unit dosage form comprising a formulation described herein, such as in any one of Tables 1-5. The unit dosage form can be characterized by, for example, the volume of the unit dosage form, such as where the unit dosage form has a volume in the range of about 0.5 mL to about 3 mL. In certain embodiments, the unit dosage form has a volume in the range of about 1.8 mL to about 2.2 mL. In certain other embodiments, the unit dosage form has a volume of about 2 mL.

In certain embodiments, the unit dosage form is characterized by the feature that the formulation is sealed in a container containing an inert gas (such as nitrogen gas).

In certain embodiments, the unit dosage form is characterized by the identity of the container housing the unit dosage form, such as where the unit dosage form is in a syringe.

IV. Therapeutic Applications

The invention provides a method of treating pain in a patient. The method comprises administering to a patient in need thereof a therapeutically effective amount of a formulation described herein, such as a formulation in any one of Tables 1-5, to a site at or near the location of pain, in order to treat the pain.

The invention provides a method of treating pain in a patient, wherein the method comprises administering to a patient in need thereof a therapeutically effective amount of a formulation described herein, such as a formulation in any one of Tables 1-5, in order to treat the pain.

Another aspect of the invention provides for the use of a formulation described herein (such as a formulation in any one of Tables 1-5) in the manufacture of a medicament. The medicament may be for treating pain in a patient.

Types of Pain

Various types of pain are contemplated to be treated using formulations described herein. Exemplary types of pain for treatment include pain due to nerve injury (e.g., a neuroma or a neuroma in continuity), pain due to a tumor (e.g., a tumor in soft tissue), pain associated with a painful trigger point, pain due to inflammation, and pain due to injury to tissue. In certain embodiments, the pain is due to a neuropathy, tumor, or inflammation. In other embodiments, the pain is due to inflammation of soft tissue. In other embodiments, the pain is due to inflammation of a joint, tendon, nerve, or muscle. In other embodiments, the pain is associated with a painful trigger point or tissue injury. In other embodiments, the pain is visceral pain. In yet other embodiments, the pain is due to a metabolic disease (e.g., diabetes, hemochromatosis, or Wilson's Disease), a hematologic disease (e.g., sickle cell disease), a coagulopathy (e.g., hemophilia AB or factor VII deficiency), an abnormal deposition of substances into tissues (e.g., amyloid or lipodystrophy). In yet other embodiments, the pain is due to a change in local tissue structure, such as scarring, abnormal healing, lack of healing, or pressure in or on tissue.

More specific description of types of pain for treatment are provided below.

In certain embodiments, the pain is due to tendonitis, a myalgia (i.e., pain originating from disease and/or inflammation of muscle), bone or joint pain associated with inflammation, bone or joint pain due to an injury, or bone or joint pain due to arthritis associated with a degenerative disease, rheumatoid arthritis, osteoarthritis, or other arthritic condition. In yet other embodiments, the pain is due to bursitis, a sprain, a fracture, surgery, ligament inflammation, or ligament damage.

In certain embodiments, the pain is due to a tumor. The pain due to a tumor may be pain due to a metastatic tumor. In certain embodiments, the tumor may occur in the breast, kidney, brain, colon, colorectal tissue, prostate, cervix, uterus, lung, or bone. In certain other embodiments, the tumor may occur in the breast, kidney, brain, colon, colorectal tissue, prostate, cervix, uterus, or lung. In yet other embodiments, the tumor may occur in the skin, muscle, ovary, stomach, a blood vessel, cartilage, sinus, esophagus, eye, pancreas, liver, gall bladder, testes, lymph node, bladder, or a nerve. In yet other embodiments, the pain is due to a liquid tumor. The tumor may be further characterized by, for example, whether it is malignant or benign.

In certain embodiments, the pain to be treated is visceral pain. In certain other embodiments, the pain to be treated is nociceptive pain (i.e., pain transmitted across intact neuronal pathways), neuropathic pain (i.e., pain caused by damage to neural structures), pain from nerve injury (i.e., a neuroma or neuroma in continuity), pain from a neuralgia (i.e., pain originating from disease and/or inflammation of nerves), pain associated with a neurotransmitter-dysregulation syndrome (i.e., a disruption in quantity/quality of neurotransmitter molecules associated with signal transmission in normal nerves), or pain associated with an orthopedic disorder such as a condition of the foot, knee, hip, spine, shoulder, elbow, hand, head, or neck. In yet other embodiments, the pain to be treated is pain from a therapeutic intervention (e.g., chemotherapy, radiation, a toxin) or pain associated with tissue deposition of a material (e.g., an amyloid, a lipodystrophy, or crystal deposition disease).

Exemplary types of nociceptive pain include, for example, post-operative pain, a cluster headache, dental pain, surgical pain, pain resulting from a severe burn, post-partum pain, angina, genito-urinary tract pain, pain associated with a sports injury (e.g., tendonitis or bursitis), pain due to joint degeneration, and pain due to prostatitis or cystitis. In certain embodiments, the pain is bladder pain. Additional types of nociceptive pain include, for example, chronic headache (e.g., cluster headache), pain from scarring in any location, pain associated with a traumatic injury, pain due to prostatitis, gall bladder pain, and pain due to one or more of the following: a strain, sprain, fracture, dislocation, myalgia, or tissue damage.

Exemplary neuropathies include, for example, syndromes of acute ascending motor paralysis with variable disturbance of sensory function; syndromes of subacute sensorimotor paralysis; syndromes of acquired forms of chronic sensorimotor polyneuropathy; syndromes of determined forms of genetic chronic polyneuropathy; syndromes of recurrent or relapsing polyneuropathy; and syndromes of mononeuropathy or multiple neuropathies. Exemplary syndromes of acute ascending motor paralysis include acute idiopathic polyneuritis, Landry-Guillain-Barre Syndrome, acute immune-mediated polyneuritis, infectious mononucleosis polyneuritis, hepatitis polyneuritis, diptheric polyneuropathy, porphyric polyneuropathy, toxic polyneuropathy (e.g., thallium), acute axonal polyneuropathy, acute panautonomic neuropathy, vaccinogenic, serogenic, paraneoplastic, metabolic, toxic, chemotherapeutic, radiation, an infiltrative neuropathy, and polyaretetic and lupus polyneuropathy.

Exemplary syndromes of subacute sensorimotor paralysis include deficiency states (e.g., beriberi, pellagra, and vitamin B12); heavy metal/industrial solvent poisonings (e.g., arsenic or lead); drug use or overdose (e.g., isoniazid, disulfuram, platinum-based chemotherapy (e.g., cisplatin), vincristine, taxol, or chloramphenicol overdose); uremic polyneuropathy; metabolic (e.g., diabetes); infiltrative (e.g., amyloid, crystal, metal, or lipodystrophies); sarcoidosis; ischemic neuropathy and peripheral vascular disease; AIDS; and radiation (radiotherapy).

Exemplary syndromes of chronic sensorimotor include a carcinoma, myeloma and other malignancies; paraproteinemias; uremia; beriberi (usually subacute), diabetes, hypo/ hyperthyroidism; rheumatic and connective tissue disease; amyloidosis; leprosy; Lyme disease, and sepsis.

Exemplary genetic chronic polyneuropathies include dominant mutilating sensory neuropathy (adult); recessive mutilating sensory neuropathy (childhood); congenital insensitivity to pain; spinocerebellar degenerations; Riley Day Syndrome; Universal Anesthesia Syndrome; polyneuropathies with metabolic disorder; and mixed sensorimotor-autonomic type polyneuropathies.

Exemplary recurrent/relapsing polyneuropathies include idiopathic polyneuritis; porphyria; chronic inflammatory polyradiculoneuropathy; mononeuritis multiplex; beriberi/ drug overdose; refsum disease and tangier disease.

Exemplary mono/multiple neuropathies include pressure palsies; traumatic neuropathies (e.g., irradiation or electrical injury); serum; vaccinogenic (e.g., rabies, smallpox); herpes zoster; neoplastic infiltration; leprosy; diptheretic wound infections; migrant sensory neuropathy; shingles; and postherpetic neuralgia.

Neurotransmitter-dysregulation pain syndromes include, for example, generalized syndromes, localized syndromes, craniofascial pain, vascular disease, rectal pain, perineum pain, external genitalia pain, chronic regional pain syndrome, and local syndromes of the leg/foot.

Exemplary generalized syndromes include stump pain, causalgia, reflex sympathetic dystrophy, fibromyalgia or local and/or diffuse myofascial pain and burns. Exemplary localized syndromes include trigeminal neuralgia; acute herpes zoster; panautonomic neuralgia; *geniculate* neuralgia (Romsay Hunt Syndrome); glossopharyngeal neuralgia; vagus nerve neuralgia and occipital neuralgia. Craniofacial pain includes temporomandibular pain. Suboccipital and cervical musculoskeletal disorders include myofascial syndrome, which includes cervical, sprain cervical hyperextension (whiplash); sternocleidomastoid muscle; trapezius muscle; and stylohyoid process syndrome (Eagle's syndrome). Vascular disease includes Raynaud's disease; Raynaud's phenomenon; frostbite; erythema pernio (chilblains); acrocyanosis and livedo *reticularis*. Rectal, perineum and external genitalia pain include iliohypogastric neuralgia; iliolinguinal nerve; genotifemoral nerve and testicular pain. Local syndromes of the leg/foot include lateral cutaneous neuropathy (neuralgia paresthetica); obturator neuralgia; femoral neuralgia; sciatica neuralgia; interdigital neuralgia of the foot (Morton's metatarsalgia or neuroma); injection neuropathy and painful legs and moving toes.

In certain embodiments, the pain is due to chronic post-herniorrhaphy, Morton's neuroma, a mastectomy, a median sternotomy, an orthopedic disorder, bursitis, tendonitis, ligamentous injury, meniscal injury, back/neck pain, a heel spur, or open or laparoscopic cholecystectomy.

Exemplary orthopedic disorders that may cause pain contemplated for treatment using formulations described herein include, for example, disorders of the knee, shoulders, back, hip, spine, elbows, foot, hand and other disorders, which involve pain at a specific site or body space. Orthopedic disorders affecting these locations include, for example, bursitis, tendonitis, ligamentous pain, chostochondritis, osteoarthritis, and rheumatoid arthritis (or other inflammatory or autoimmune diseases). Bursitis often occurs in multiple different locations including, for example, the shoulder (subacromial or subdeltoid bursitis). Other sites include the olecranon (miners' elbow), prepatellar (housemaid's knee) or suprapatellar, retrocalcaneal (Achilles), iliopectineal (iliopsoas) of the hip, anserine (medial inferior, tibial plateau, ischial (tailor's or weaver's bottom)) of the pelvis, greater trochanteric of the femur, and first metatarsal head (bunion). Bursitis may be caused by trauma, chronic overuse, inflammatory arthritis (e.g., gout, pseudogout, and rheumatoid arthritis, other inflammatory diseases [immune/ genetic]), or acute or chronic infection (e.g., pyogenic organisms, particularly *Staphylococcus aureus*; tuberculosis organisms), as well as post-infectious rheumatic diseases (e.g., chronic Lyme Disease and post-infectious arthritis). Orthopedic disorders of the foot include, for example, heel spurs, corns, bunions, a neuroma (e.g., Morton's neuroma), arthritis of the foot (e.g., osteoarthritis), hammertoes, ankle sprain, fractures of the ankle or metatarsals or sesamoid bone or toes, plantar fasciitis and injuries to the Achilles tendon. In certain embodiments, the pain is due to a bunion.

Orthopedic disorders of the hand include, for example, arthritis, carpal tunnel syndrome, ganglion cysts, tendon problems such as lateral epicondylitis, medial epicondylitis, rotator cuff tendonitis, De Quervian's tenosynovitis, and trigger finger/trigger thumb. Other orthopedic disorders include, for example, Paget's disease, scoliosis, soft-tissue injuries such as contusions, sprains and strains, long bone fractures, short bone fractures, small bone fractures, and various other sports or traumatic injuries, some of which include patellar tendonitis, lumbar strain, and cervical strain.

In certain embodiments, the pain is chronic pain. In certain embodiments, the pain is acute pain.

In certain embodiments, the pain arises from the capsule of a joint, a degenerative disc, or a lesion (e.g., a cyst).

In yet other embodiments, the pain is one or more of the types of pain described in U.S. Pat. Nos. 5,962,532 and 8,420,600, which are hereby incorporated by reference.

Joint Pain

The pain for treatment may be pain emanating from a joint, such as a joint selected from the group consisting of knee, elbow, hip, sternoclavicular, temporomandibular, shoulder, spine, wrist, ankle, a joint in the hand, and a joint in the foot. Accordingly, in certain embodiments, the pain is joint pain. In certain embodiments, the pain is pain in a knee joint, hip joint, shoulder joint, a sterno-manubrial joint, an acromioclavicular joint, a tempo mandibular joint, elbow joint, a carpal joint, a tarsal joint, a facet joint, or a metatarsal joint. In certain embodiments, the pain is pain in a knee joint, hip joint, shoulder joint, elbow joint, carpal joint, tarsal joint, or metatarsal joint. In certain embodiments, the joint pain is pain in a knee joint. In certain other embodiments, the joint pain is pain in a carpal joint or a tarsal joint.

In certain embodiments, the patient suffers from an inflammatory, traumatic, post-traumatic, post-surgical, auto-immune, genetic or congenital defect of the joint. In certain embodiments, the patient suffers from an inflammatory, autoimmune, genetic or congenital defect of the joint. In certain embodiments, the patient suffers from osteoarthritis of the joint. In certain other embodiments, the patient suffers from rheumatoid arthritis of the joint.

In certain embodiments, the joint is an osteoarthritic joint selected from a knee, hip, carpal-metacarpal joint, metatarsal joint, ankle, acromioclavicular joint, wrist, elbow, finger joint, vertebral joint, or temporal mandibrial joint. In certain embodiments, the joint is an osteoarthritic knee joint.

In a preferred embodiment, the pain to be treated is joint pain in a knee joint affected by osteoarthritis.

In certain other embodiments, the joint is a degenerative disc joint. Exemplary disc joints include a lumbar joint, thoracic joint, or cervical joint.

Route of Administration

The formulations are optimal for administration by injection, though the formulations may be administered by any of the medically accepted routes of administration that a physician of ordinary skill deems safe and appropriate. Exemplary routes of administration include injection into a joint, injection into a nerve or into tissue in proximity to a nerve, and injection into the spinal canal. In certain embodiments, the administering comprises injecting the formulation at or near the site of pain in the patient. In certain embodiments, the administering is intra-articular injection or intrathecal injection. In certain embodiments, the administering is intra-articular injection. In certain embodiments, the administering is intrathecal injection. In certain embodiments, the administering is epidural injection. In certain embodiments, the administering is injection to the spine, such as into a spinal disc.

In yet other embodiments of the therapeutic methods, the administering comprises injecting the formulation into a joint to treat joint pain. In yet other embodiments, the administering comprises injecting the formulation into the intra-articular space of a joint. In yet other embodiments, the administering comprises injecting the formulation into the intra-articular space of a knee joint to treat knee joint pain. In yet other embodiments, the method comprises cooling said joint before, and optionally after, injecting said formulation.

In yet other embodiments, the administering comprises intrathecal injection of the formulation to the patient.

In certain preferred embodiments, the administering comprises injecting the formulation into a joint to treat joint pain. In other preferred embodiments, the formulation is administered to the joint by intra-articular injection. In still other preferred embodiments, the administering comprises injecting the formulation into the intra-articular space of a knee joint to treat knee joint pain, such as osteoarthritic knee joint pain in a human.

In yet other embodiments, the formulation is administered by subcutaneous delivery, intrathecal delivery, intramuscular delivery, pulmonary delivery, topical delivery (e.g., a gel, ointment, lotion, or transdermal), oral delivery (e.g., delayed release formulation), or intra-vesicular delivery (e.g., for delivery to a bladder).

Attenuation of Initial Hyperalgesic Effect of Capsaicin

An anesthetic agent can be administered to the patient in order to attenuate any initial hyperalgesic effect caused by administration of the capsaicin in the formulation. The anesthetic agent can be administered directly to the site in which the capsaicin will be administered, or at a remote site that causes anesthesia at the site where the capsaicin will be administered. For example, epidural regional anesthesia can be provided to patients to which the capsaicin will be administered at a site located from the waist down.

In certain embodiments, the anesthetic agent is a caine alkaloid. Exemplary caine alkaloids include lidocaine, dibucaine, bupivacaine, ropivacaine, etidocaine, tetracaine, procaine, chlorocaine, prilocaine, mepivacaine, xylocaine, 2-chloroprocaine, and pharmaceutically acceptable salts thereof.

The dose of local anesthetic will depend on the anesthetic being administered as well as the site where the local anesthetic is administered. For example, in embodiments where the local anesthetic is administered via a regional block (e.g., an ankle block), the dose of anesthetic may range from about 1 mL up to about 30 mL of a 0.5% solution of anesthetic agent (e.g., bupivacaine). In other embodiments, a dose of up to 5 mg/kg of a solution containing 0.25% to 5% of anesthetic agent (e.g., lidocaine) may be administered as a nerve block, such as by administration to the site of pain or an area proximal to the site of pain. In yet other embodiments, the dose of local anesthetic may range from about 0.5 mL to about 60 mL of a 0.25% to 5% solution of anesthetic agent.

In certain embodiments, the anesthetic agent is administered as a proximal, regional, somatic, or neuraxial block. Alternatively, a general anesthetic (or other agent that causes sedation) may be used to attenuate any initial hyperalgesic effect caused by administration of capsaicin.

In certain other embodiments, any initial pain due to the caspicin injection may be attenuated by use of an opioid administered orally, or by an alternative systemic route (e.g., intravenously or subcutaneously).

Accordingly, in one aspect, the therapeutic methods for treating pain further comprise administering an anesthetic, concurrently or prior to the aqueous capsaicin injectable formulation, in an amount and location effective to attenuate any initial hyperalgesic effect of the capsaicin. In certain embodiments, the anesthetic is a general anesthetic. In certain embodiments, the anesthetic is a local anesthetic. In certain embodiments, the local anesthetic is a caine alkaloid. In certain embodiments, the local anesthetic is lidocaine or a pharmaceutically acceptable salt thereof.

Additional description of procedures and agents that may be used to attenuate any initial hyperalgesic effect caused by administration of the capsaicin-containing formulation are described in U.S. Pat. No. 5,962,532, which is hereby incorporated by reference.

Patients for Treatment

The method may be further characterized according to the patient to be treated. Accordingly, in certain embodiments, the patient is an adult human. In other embodiments, the patient is a canine.

Duration of Pain Relief

The method may be further characterized according to the duration of pain relief provided. For example, in certain embodiments, the method provides relief from said pain for a duration of at least 3 months. In other embodiments, the method provides relief from said pain for a duration of at least 6 months. In other embodiments, the method provides relief from said pain for a duration of from about 1 month to about 9 months, from about 3 months to about 9 months, from about 3 months to about 7 months, or about 3 months to about 6 months.

Dose of Capsaicin Administered to the Patient

The dose of capsaicin administered to the patient may depend on, for example, the type of pain to be treated and may be selected according to dose-selection procedures known to those skilled in the art. In certain embodiments, the dose of capsaicin administered to a patient as a single administration is from about 1 µg to about 5000 µg, from about 250 µg to about 2000 µg, or 500 µg to about 1000 µg. In certain embodiments, the administering is injecting at or near the site of pain a single dose of the capsaicin in an amount of from about 1 µg to about 5000 µg. In certain embodiments, the administering is injecting at or near the site of pain a single dose of the capsaicin in an amount of from about 250 µg to about 2000 µg. In certain embodiments, the administering is injecting at or near the site of pain a single dose of the capsaicin in an amount of from about 500 µg to about 1000 µg. In certain embodiments, the administering is injecting at or near the site of pain a single dose of the capsaicin in an amount of about 1000 µg.

V. Kits for Use in Medical Applications

Another aspect of the invention provides a kit for treating a disorder. The kit comprises: i) instructions for treating pain, such as osteoarthritic knee joint pain; and ii) an aqueous capsaicin injectable formulation described herein, such as one of the formulations described in Tables 1-5.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and are not intended to limit the invention.

Example 1—Analysis of Capsaicin Solubility of Multiple Aqueous Formulations Containing a Solubilizing Agent Multiple aqueous formulations were prepared and analyzed to determine the amount of dissolved capsaicin. The formulations contained different solubilizing agents to increase the amount of capsaicin dissolved in the aqueous medium. The experimental procedures and results are described below.

Part I—Analysis of Capsaicin Solubility in Multiple Aqueous Formulations

Aqueous formulations were prepared containing capsaicin and a solubilizing agent selected from Tween 20, Tween 80, Kolliphor ELP, Kolliphor HS 15, Kollidon 12 PF, and Kollidon 17 PF as further defined below. Experimental procedures and results are described below.

Experimental Procedures

The equilibrium solubility of capsaicin was determined in a series of aqueous solutions. Six different types of vehicles were prepared at three different concentrations each. Tween 20 solutions were prepared at a range of 0.2% to 10% (w/v). Tween 80 solutions were prepared at a range of 0.2% to 1.0% (w/v). Kolliphor ELP and Kolliphor HS 15 solutions were both prepared at a range of 5% to 20% (w/v). Kollidon 12 PF solutions were prepared at a range of 2.5% to 10% (w/v). Kollidon 17 PF solutions were prepared at a range of 0.5% to 2.0% (w/v).

For each test solution, quantities of 20-30 mg of capsaicin were added to a micro centrifuge tubes. A volume of 1.5 mL of the appropriate test vehicle was added to each to create a suspension. The capped tubes were mixed on a laboratory rotator at ambient temperature. At approximately 48 hours after sample preparation, the tubes were removed from the rotator and centrifuged to separate the solid phase from the solution. An aliquot of the supernatant was withdrawn from each sample and diluted as necessary for HPLC analysis to determine the solution concentration of the capsaicin. The pH of the supernatant was measured 48 hours after preparation and the appearance of solid and supernatant were noted.

As reported in the literature, Tween 20 is also known as Polysorbate 20, which has the chemical name polyoxyethylene (20) sorbitan monolaurate. Tween 80 is also known as Polysorbate 80, which has the chemical name polyoxyethylene (20) sorbitan monooleate. Kolliphor ELP has CAS Registry No. 61791-12-6, and is a composition sold by BASF under the chemical name polyoxyl-35-castor oil and marketed by BASF as Kolliphor™ ELP; the composition is made by reacting castor oil with ethylene oxide in a molar ratio of 1:35. The Kolliphor HS 15 has CAS Registry No. 70142-34-6, and is a mixture containing (a) about 70% (w/w) of a mixture of

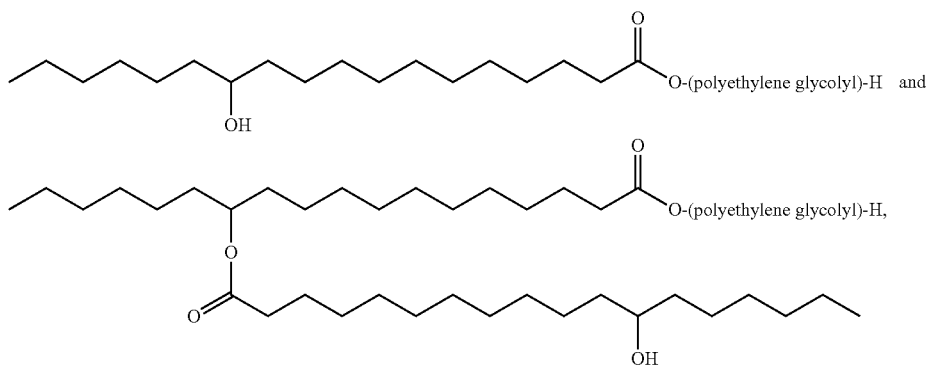

and (b) about 30% (w/w) polyethylene glycol; where the polyethylene glycolyl has a weight-average molecular weight of about 660 g/mol; which is sold and marketed by BASF as KOLLIPHOR® HS 15. Kollidon 12 PF is a polyvinylpyrrolidone having a weight-average molecular weight in the range of 2,000 to 3,000 g/mol, sold by BASF under the name KOLLIDON® 12 PF. Kollidon 17 PF is a polyvinylpyrrolidone having a weight-average molecular weight in the range of 7,000 to 11,000 g/mol, sold by BASF under the name KOLLIDON® 17 PF.

Results

Results from the above analysis are presented in Table 6. For all test solutions except those containing Kollidon 12 PF or Kollidon 17 PF, the observed concentration of capsaicin increased concordant with increasing surfactant concentration. With the exception of Kollidon 12 PF and Kollidon 17 PF, at least one test solution from each of different solubilizing agents reached the minimum target concentration of capsaicin of 1 mg/mL capsaicin. Both Kollidon 12 PF and Kollidon 17 PF solutions, at all strengths, failed to reach the minimum target concentration of 1 mg/mL capsaicin. The highest concentrations of capsaicin were observed in the 20% strength Kolliphor ELP {c(Capsaicin)=13.0 mg/mL} and 20% Kolliphor HS 15 {c(Capsaicin)=12.2 mg/mL} solutions.

The observed pH-values in the supernatants of the test solutions ranged from pH=3.88 to pH=7.27. Appearances of both the liquid supernatant and the remaining solid were observed to be clear and as at initial solution preparation. For all samples that had remaining solid, the solid appeared white and had no notable difference from its starting consistency.

After centrifugation of the sample containing 20% Kolliphor ELP no solid residue could be detected, which signifies that the equilibrium solubility for Capsaicin in this vehicle was not reached and is greater than the observed c(Capsaicin)=13.0 mg/mL. For the 20% Kolliphor HS vehicle, the amount of pelleted solid from centrifugation was at the limit of detection.

TABLE 6

| Sample (amount in weight percent) | Observed [Capsaicin] (mg/mL) | pH (at 48 hr) | appearance pellet | appearance supernatant |
| --- | --- | --- | --- | --- |
| Tween 20 (0.2%) | 0.146 | 6.78 | white | clear |
| Tween 20 (2%) | 1.11 | 6.16 | white | clear |
| Tween 20 (10%) | 5.39 | 6.03 | white | clear |
| Tween 80 (0.2%) | 0.233 | 6.45 | white | clear |
| Tween 80 (0.5%) | 0.245 | 7.27 | white | clear |
| Tween 80 (1.0%) | 1.00 | 7.03 | white | clear |
| Kolliphor ELP (5%) | 4.20 | 5.61 | white | clear |
| Kolliphor ELP (10%) | 8.14 | 5.21 | white | clear |

TABLE 6-continued

| Sample (amount in weight percent) | Observed [Capsaicin] (mg/mL) | pH (at 48 hr) | appearance pellet | appearance supernatant |
| --- | --- | --- | --- | --- |
| Kolliphor ELP (20%) | 13.0 | 4.70 | none | clear |
| Kolliphor HS 15 (5%) | 3.81 | 6.65 | white | clear |
| Kolliphor HS 15 (10%) | 7.18 | 6.97 | white | clear |
| Kolliphor HS 15 (20%) | 12.2 | 7.01 | white | clear |
| Kollidon 12 (2.5%) | 0.276 | 4.22 | white | clear |
| Kollidon 12 (5%) | 0.624 | 4.00 | white | clear |
| Kollidon 12 (10%) | 0.378 | 3.88 | white | clear |
| Kollidon 17 (0.5%) | 0.150 | 5.75 | white | clear |
| Kollidon 17 (1.0%) | 0.247 | 4.66 | white | clear |
| Kollidon 17 (2.0%) | 0.199 | 4.20 | white | clear |

Part II—Capsaicin Solubility in Cyclodextrin Solutions

Aqueous formulations were prepared containing capsaicin and a solubilizing agent selected from hydroxypropyl-β-cyclodextrin and captisol (i.e., sodium sulfobutyl ethers β-cyclodextrin). Experimental procedures and results are described below.

Experimental Procedures

For each cyclodextrin solution, quantities of about 20-30 mg of capsaicin were suspended in 1.5 mL of the respective cyclodextrin solution. The capped tubes were mixed on a laboratory rotator at ambient temperature. At approximately 48 hours after sample preparation, the tubes were removed from the rotator and centrifuged to separate the solid phase from the solution. An aliquot of the supernatant was withdrawn from each sample and diluted as necessary for HPLC analysis to determine the solution concentration of the capsaicin, which was quantitated relative to the reference standard. The pH of the supernatant was measured and the appearance of both the supernatant and the solid were noted at 48 hours.

Results

Results from the above analysis are presented in Table 7. For both cyclodextrins tested, at all solution strengths, at least 2 mg/mL capsaicin was observed. Hydroxypropyl-β-cyclodextrin had slightly higher concentrations of capsaicin than captisol for all solution strengths. The pH of the solutions ranged from 7.00 to 7.94. The liquid portion of each sample was clear and appeared unchanged from its original state. The solid portion of each sample was white, granular, and appeared as it did prior to the addition of the cyclodextrin solution. The 25% solutions of both cyclodextrins had very little remaining solid.

TABLE 7

| Sample | Peak area (mAU) | Observed [Capsaicin], mg/mL | appearance pellet | appearance supernatant | pH (at 48 hr) |
|---|---|---|---|---|---|
| 5% Hydroxypropyl-β-cyclodextrin | 4247905 | 2.39 | White | clear | 7.32 |
| 10% Hydroxypropyl-β-cyclodextrin | 7891725 | 4.45 | White | clear | 7.44 |
| 25% Hydroxypropyl-β-cyclodextrin | 20541037 | 11.6 | White | clear | 7.00 |
| 5% Captisol | 3734548 | 2.10 | White | clear | 7.94 |
| 10% Captisol | 6561988 | 3.70 | White | clear | 7.65 |
| 25% Captisol | 14660216 | 8.26 | White | clear | 7.23 |

Part III—Capsaicin Solubility in Additional Aqueous Solutions

Aqueous formulations were prepared containing capsaicin and an additive. The solubility of capsaicin was also analyzed in deionized water. Experimental procedures and results are described below.

Experimental Procedures

For each of the six solutions, quantities of about 20-30 mg of capsaicin were added to each of six micro centrifuge tubes. A volume of 1.5 mL of the appropriate solution was added to each to create a suspension. The capped tubes were mixed on a laboratory rotator at ambient temperature. At approximately 7 days after sample preparation, the tubes were removed from the rotator and centrifuged to separate the solid phase from the solution. An aliquot of the supernatant was withdrawn from each sample and diluted as necessary for HPLC analysis to determine the solution concentration of the capsaicin, which was quantitated relative to the reference standard. The pH-values of the supernatant were measured and the appearance of both the supernatant and the pelleted solid were noted.

Results

Results from the above analysis are presented in Table 8. The lowest concentration of the capsaicin was observed in deionized water with c(Capsaicin)=7.6 µg/mL while solubilization of capsaicin in aqueous 2.5% glycerol resulted in the highest observed concentration of capsaicin with c(Capsaicin)=38 µg/mL.

TABLE 8

| Sample | Peak area (mAU) | Observed [Capsaicin], mg/mL | appearance pellet | appearance supernatant | pH (at 7 days) |
|---|---|---|---|---|---|
| Water | 135565 | 0.008 | White | clear | 4.53 |
| 5% mannitol | 381253 | 0.021 | White | clear | 5.53 |
| 5% mannitol, 0.1M pH 5 Citrate | 513817 | 0.020 | White | clear | 4.73 |
| 5% mannitol, 0.1M pH 6 Citrate | 378148 | 0.021 | White | clear | 5.86 |
| 5% mannitol, 0.1M pH 5 Acetate | 484164 | 0.027 | White | clear | 5.25 |
| 2.5% glycerol in water | 682320 | 0.038 | White | clear | 6.47 |

Example 2—Stability Analysis of Exemplary Formulations

The aqueous formulations in Table 9 below were subjected to stability analysis by storage at 5° C., 25° C., 40° C., and/or 60° C., followed by analytical analysis to determine the amount of capsaicin and/or impurities in the formulation. Results are provided below. The abbreviation BHT refers to dibutylhydroxytoluene. The abbreviation "EDTA" refers to ethylenediaminetetraacetic acid. The Kolliphor HS-15 has CAS Registry No 70142-34-6, and is a mixture containing (a) about 70% (w/w) of a mixture of

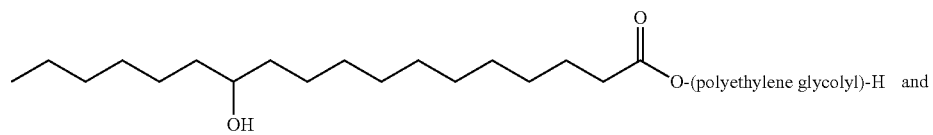

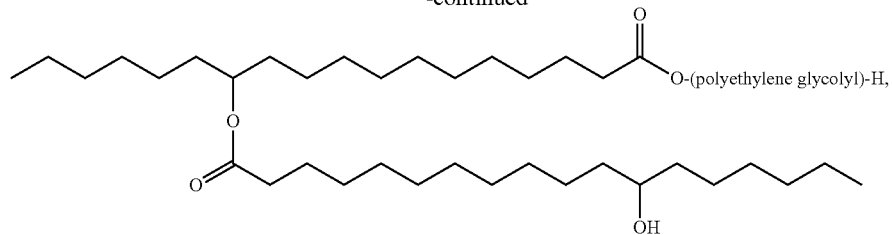

and (b) about 30% (w/w) polyethylene glycol; where the polyethylene glycolyl has a weight-average molecular weight of about 660 g/mol; which is sold and marketed by BASF as KOLLIPHOR® HS 15. The phrase "Average Particles Per Container" refers to the average number of particles observed in a container, where the container held approximately 1.5 mL of aqueous formulation to be analyzed.

TABLE 9

| Solution 1A: | Solution 1P: |
|---|---|
| 1 mg/ml Capsaicin<br>2% Kolliphor HS-15<br>20 mM citrate buffer<br>0.1% disodium EDTA<br>0.01% BHT<br>0.625% NaCl<br>q.s. water | 2% Kolliphor HS-15<br>20 mM citrate buffer<br>0.1% disodium EDTA<br>0.01% BHT<br>0.625% NaCl<br>q.s. water |

TABLE 9-continued

| Solution 2A: | Solution 3A: |
|---|---|
| 2 mg/ml Capsaicin<br>4% Kolliphor HS-15<br>20 mM citrate buffer<br>0.1% disodium EDTA<br>0.01% BHT<br>0.625% NaCl<br>q.s. water | 1 mg/ml Capsaicin<br>2% Kolliphor HS-15<br>0.1% disodium EDTA<br>0.01% BHT<br>3.15% Dextrose<br>q.s. water |
| Solution 3P: | Solution 4A: |
| 2% Kolliphor HS-15<br>20 mM citrate buffer<br>0.1% disodium EDTA<br>0.01% BHT<br>3.15% Dextrose<br>q.s. water | 2 mg/ml Capsaicin<br>4% Kolliphor HS-15<br>20 mM citrate buffer<br>0.1% disodium EDTA<br>0.01% BHT<br>3.15% Dextrose<br>q.s. water |

TABLE 1A (A) Summary of results for the Solution 1A formulation at 5° C.

| Testing time, 5° C. (months) | Solution 1A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 1.0 | 873 (0.003%) | 1856 (0.005%) | 1842 (0.005%) |
| 1[1] | | | | | | | | |
| 3[2] | | | | | | | | |
| 6[1] | Clear and colorless | 5.5 | | | 1.0 | N/A | N/A | 1864 (0.005%) |

| Testing time, 5° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 1031 (0.003%) | 1751 (0.005%) | 5490 (0.016%) | 30126 (0.087%) | 34429382 (99.794%) | 28100 (0.081%) |
| 1[1] | | | | | | |
| 3[2] | | | | | | |
| 6[1] | N/A | N/A | N/A | N/A | 33913917 (99.870%) | 8866 (0.026%) |

[1]Performed on HPLC10
[2]Performed on HPLC12

TABLE 2A

| (B) Summary of results for the Solution 1A formulation at 25° C. | | | | | | | | |
|---|---|---|---|---|---|---|---|---|
| Testing time, 25° C. (months) | Solution 1A Attribute Appearance | pH | Average Particles Per Container 10.000 μM | Average Particles Per Container 25.000 μM | Conc., HPLC (mg/ml) | HPLC Purity, Area % Peak 1, 4.4 min | Peak 2, 5.6 min | Peak 3, 8.4 min |
| 0[1] | Clear and colorless | 5.5 | 19.40 | 1.10 | 1.0 | N/A | 1858 (0.005%) | 1834 (0.005%) |
| 1[1] | Clear and colorless | 5.5 | | | 1.0 | 678 (0.002%) | 1881 (0.005%) | 1844 (0.006%) |
| 3[2] | Clear and colorless | 5.5 | | | 0.9 | N/A | 2151 (0.007%) | 4995 (0.016%) |
| 6[1] | Clear and colorless | 5.5 | 40.60 | 1.30 | 1.0 | N/A | 1759 (0.005%) | 1914 (0.006%) |

| Testing time, 25° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 886 (0.003%) | 2919 (0.008%) | 7432 (0.021%) | 32759 (0.095%) | 34570267 (99.795%) | 23242 (0.067%) |
| 1[1] | 1073 (0.003%) | 1538 (0.004%) | 5778 (0.017%) | 30665 (0.089%) | 34565985 (99.852%) | 7828 (0.023%) |
| 3[2] | 1642 (0.004%) | 2491 (0.008%) | 4649 (0.015%) | 35711 (0.113%) | 31442165 (99.631%) | 21338 (0.068%) |
| 6[1] | N/A | N/A | N/A | N/A | 33979632 (99.871%) | 6676 (0.020%) |

[1]Performed on HPLC10
[2]Performed on HPLC12

TABLE 2A-1

| (C) Additional peaks for Solution 1A formulation at 25° C. at t = 3 months. | | |
|---|---|---|
| HPLC Purity, Area % Peak @ 7.9 min | T = 3 m extra peaks Peak @ 15.3 min | Peak @ 34.4 min |
| 14113 (0.045%) | 6702 (0.021%) | 4917 (0.014%) |

TABLE 3A

| (D) Summary of results for the Solution 1A formulation at 40° C. | | | | | | | | |
|---|---|---|---|---|---|---|---|---|
| Testing time, 40° C. (months) | Solution 1A Attribute Appearance | pH | Average Particles Per Container 10.000 μM | Average Particles Per Container 25.000 μM | Conc., HPLC (mg/ml) | HPLC Purity, Area % Peak 1, 4.4 min | Peak 2, 5.6 min | Peak 3, 8.4 min |
| 0[1] | Clear and colorless | 5.5 | 45.80 | 2.00 | 1.0 | N/A | 1923 (0.006%) | 1856 (0.005%) |
| 1[1] | Clear and colorless | 5.5 | | | 1.0 | 677 (0.002%) | 2146 (0.006%) | 1898 (0.005%) |
| 3[2] | Clear and colorless | 5.5 | | | 0.9 | 1591 (0.005%) | 3347 (0.011%) | 4381 (0.016%) |
| 6[1] | Clear and colorless | 5.5 | 66.70 | 1.70 | 1.0 | N/A | 10294 (0.030%) | 1654 (0.005%) |

| Testing time, 40° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 985 (0.003%) | 2006 (0.006%) | 6269 (0.018%) | 30643 (0.088%) | 34576418 (99.852%) | 7561 (0.022%) |
| 1[1] | 928 (0.003%) | 1871 (0.005%) | 5730 (0.016%) | 30312 (0.087%) | 34727820 (99.843%) | 11056 (0.032%) |
| 3[2] | 1668 (0.005%) | 2218 (0.007%) | 4523 (0.015%) | 32761 (0.106%) | 30846401 (99.642%) | 17222 (0.056%) |

TABLE 3A-continued

(D) Summary of results for the Solution 1A formulation at 40° C.

| | | | | | | |
|---|---|---|---|---|---|---|
| 6[1] | N/A | N/A | N/A | 29082 (0.085%) | 33990190 (99.841%) | 5366 (0.016%) |

[1]Performed on HPLC10
[2]Performed on HPLC12

TABLE 3A-1

(E) Additional peaks for Solution 1A formulation at 40° C. at t = 3 months.

| HPLC Purity, Area % Peak @ 7.9 min | T = 3 m extra peaks Peak @ 15.3 min |
|---|---|
| 13886 (0.045%) | 5885 (0.019%) |

TABLE 3A-2

(F) Additional peaks for Solution 1A formulation at 40° C. at t = 6 months.

| HPLC Purity, Area % Peak @ 7.9 min | T = 6 m extra peaks |
|---|---|
| 3717 (0.011%) | — |

TABLE 4A

(G) Summary of results for the Solution 1A formulation at 60° C.

| Testing time, 60° C. (months) | Solution 1A Attribute Appearance | pH | Average Particles Per Container 10.000 μM | Average Particles Per Container 25.000 μM | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 1.0 | 656 (0.002%) | 2174 (0.006%) | 2035 (0.006%) |
| 1[1] | Cloudy, then clears up after 5 min | 5.5 | | | 1.0 | 892 (0.003%) | 3336 (0.01%) | 627 (0.002%) |
| 3 | | | | | | | | |
| 6 | | | | | | | | |

| Testing time, 60° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 1391 (0.004%) | 2705 (0.008%) | 6913 (0.020%) | 29898 (0.087%) | 34348643 (99.849%) | 6216 (0.018%) |
| 1[1] | 853 (0.002%) | 1705 (0.005%) | 4910 (0.014%) | 30368 (0.087%) | 34698973 (99.829%) | 11505 (0.033%) |
| 3 | | | | | | |
| 6 | | | | | | |

[1]Performed on HPLC10

TABLE 5A

(H) Summary of results for the Solution 1P formulation at 5° C.

| Testing time, 5° C. | Solution 1P Attribute | Average Particles Per Container | Average Particles Per Container | Conc., HPLC | HPLC Purity, Area % Peak 1, | Peak 2, | Peak 3, |

TABLE 5A-continued (H) Summary of results for the Solution 1P formulation at 5° C.

| (months) | Appearance | pH | 10.000 μM | 25.000 μM | (mg/ml) | 4.4 min | 5.6 min | 8.4 min |
|---|---|---|---|---|---|---|---|---|
| 0[1] | Clear and colorless | 5.2 | | | 0 | 527 (100%) | N/A | N/A |
| 1 | | | | | | | | |
| 3 | | | | | | | | |
| 6[1] | Clear and colorless | 5.2 | | | 0 | N/A | N/A | N/A |

| Testing time, 5° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | N/A | N/A | N/A | N/A | N/A | N/A |
| 1 | | | | | | |
| 3 | | | | | | |
| 6[1] | N/A | N/A | N/A | N/A | N/A | N/A |

[1]Performed on HPLC10

TABLE 5A-1

(I) Additional peaks for Solution 1P formulation at 5° C. at t = 1 month.

| HPLC Purity, Area % Peak @ 39.8 min | T = 1 m extra peaks |
|---|---|
| 7691 (91.462%) | — |

TABLE 6A (J) Summary of results for the Solution 1P formulation at 25° C.

| Testing time, 25° C. (months) | Solution 1P Attribute Appearance | pH | Average Particles Per Container 10.000 μM | Average Particles Per Container 25.000 μM | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.3 | 15.70 | 0.60 | 0 | 693 (100%) | N/A | N/A |
| 1[1] | Clear and colorless | 5.3 | | | 0 | 697 (100%) | N/A | N/A |
| 3[2] | Clear and colorless | 5.3 | | | 0 | N/A | N/A | N/A |
| 6[1] | Clear and colorless | 5.3 | 33.70 | 1.10 | 0 | N/A | N/A | N/A |

| Testing time, 25° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | N/A | N/A | N/A | N/A | N/A | N/A |
| 1[1] | N/A | N/A | N/A | N/A | N/A | N/A |
| 3[2] | N/A | N/A | N/A | 22037 (34.748%) | N/A | 21266 (33.532%) |
| 6[1] | N/A | N/A | N/A | N/A | N/A | N/A |

[1]Performed on HPLC10
[2]Performed on HPLC12

TABLE 6A-1

(K) Additional peaks for Solution 1P formulation at 25° C. at t = 3 months.

| HPLC Purity, Area % Peak @ 7.9 min | T = 3 m extra peaks Peak @ 15.3 min |
|---|---|
| 11261 17.756% | 8856 (13.964%) |

TABLE 7A (L) Summary of results for the Solution 1P formulation at 40° C.

| Testing time, 40° C. (months) | Solution 1P Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|---|---|---|---|---|---|---|---|
| 0[1] | Clear and colorless | 5.3 | 26.00 | 1.20 | 0 | N/A | N/A | N/A | N/A | N/A | N/A | N/A | N/A | N/A |
| 1[1] | Clear and colorless | 5.3 | | | 0 | 570 (100%) | N/A | N/A | N/A | N/A | N/A | N/A | N/A | N/A |
| 3[2] | Clear and colorless | 5.3 | | | 0 | N/A | N/A | N/A | N/A | N/A | N/A | 20712 (40.96%) | N/A | 18573 (36.729%) |
| 6[1] | Clear and colorless | 5.3 | 64.60 | 3.20 | 0 | N/A | N/A | N/A | N/A | N/A | N/A | N/A | N/A | N/A |

[1] Performed on HPLC10
[2] Performed on HPLC12

TABLE 7A-1

(M) Additional peaks for Solution 1P formulation at 40° C. at t = 3 months.

| HPLC Purity, Area % Peak @ 7.9 min | T = 3 m extra peaks Peak @ 34.4 min |
|---|---|
| 9574 (18.933%) | 1708 (0.061%) |

TABLE 8A (N) Summary of results for the Solution 1P formulation at 60° C.

| Testing time, 60° C. (months) | Solution 1P Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|---|---|---|---|---|---|---|---|
| 0[1] | Clear and colorless | 5.2 | | | 0 | N/A | N/A | N/A | N/A | N/A | N/A | N/A | N/A | N/A |
| 1[1] | Cloudy, then clears up after 5 min | 5.3 | | | 0 | N/A | N/A | N/A | N/A | N/A | N/A | N/A | N/A | N/A |
| 3 | | | | | | | | | | | | | | |
| 6 | | | | | | | | | | | | | | |

[1] Performed on HPLC10

TABLE 9A (O) Summary of results for the Solution 2A formulation at 5° C.

| Testing time, 5° C. | Solution 2A Attribute | Average Particles Per Container | Average Particles Per Container | Conc., HPLC | HPLC Purity, Area % Peak 1, | Peak 2, | Peak 3, |

TABLE 9A-continued (O) Summary of results for the Solution 2A formulation at 5° C.

| (months) | Appearance | pH | 10.000 μm | 25.000 μm | (mg/ml) | 4.4 min | 5.6 min | 8.4 min |
|---|---|---|---|---|---|---|---|---|
| 0[1] | Clear and colorless | 5.5 | | | 1.7 | 2079 (0.003%) | 4943 (0.008%) | 4018 (0.006%) |
| 1 | | | | | | | | |
| 3 | | | | | | | | |
| 6[1] | Clear and colorless | 5.5 | | | 1.7 | N/A | 5008 (0.009%) | 6050 (0.010%) |

| Testing time, 5° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2496 (0.004%) | 4587 (0.007%) | 13424 (0.022%) | 60045 (0.096%) | 62109784 (99.808%) | 26991 (0.043%) |
| 1 | | | | | | |
| 3 | | | | | | |
| 6[1] | 2337 (0.004%) | 4423 (0.007%) | N/A | 52022 (0.087%) | 59537951 (99.897%) | 11323 (0.019%) |

[1]Performed on HPLC10

TABLE 10A (P) Summary of results for the Solution 2A formulation at 25° C.

| Testing time, 25° C. (months) | Solution 2A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.6 | 16.60 | 0.40 | 1.7 | 1857 (0.003%) | 4780 (0.008%) | 4327 (0.007%) |
| 1[1] | Clear and colorless | 5.5 | | | 1.7 | 2868 (0.005%) | 6146 (0.010%) | 6318 (0.010%) |
| 3[2] | Clear and colorless | 5.5 | | | 1.6 | 2901 (0.005%) | 6621 (0.012%) | 12531 (0.023%) |
| 6[1] | Clear and colorless | 5.5 | 38.00 | 1.00 | 1.7 | N/A | 6247 (0.010%) | 6786 (0.011%) |

| Testing time, 25° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2490 (0.004%) | 5098 (0.008%) | 13402 (0.021%) | 60901 (0.098%) | 62158307 (99.819%) | 6972 (0.003%) |
| 1[1] | 2434 (0.004%) | 4829 (0.008%) | 12911 (0.021%) | 60510 (0.097%) | 62234585 (99.804%) | 6741 (0.011%) |
| 3[2] | 3404 (0.005%) | 5277 (0.010%) | 10081 (0.019%) | 56265 (0.104%) | 54007764 (99.608%) | 24506 (0.043%) |
| 6[1] | 1771 (0.003%) | N/A | N/A | N/A | 59784009 (99.828%) | 5665 (0.009%) |

[1]Performed on HPLC10
[2]Performed on HPLC12

TABLE 10A-1

(Q) Additional peaks for Solution 2A formulation at 25° C. at t = 1 month.

| HPLC Purity, Area % Peak @ 18.8 min | T = 1 m extra peaks Peak @ 36.6 min |
|---|---|
| 6874 (0.0117%) | 1581 (0.003%) |

TABLE 10A-2

(R) Additional peaks for Solution 2A formulation at 25° C. at t = 3 months.

| HPLC Purity, Area % Peak @ 7.2 min | T = 3 m extra peaks Peak @ 7.9 min | Peak @ 15.3 min |
|---|---|---|
| 3084 (0.005%) | 15264 (0.028%) | 13630 (0.025%) |

TABLE 11A (S) Summary of results for the Solution 2A formulation at 40° C.

| Testing time, 40° C. (months) | Solution 2A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.6 | 10.90 | 0.80 | 1.7 | 2010 (0.003%) | 5711 (0.009%) | 4450 (0.007%) |
| 1[1] | Clear and colorless | 5.6 | | | 1.7 | 2747 (0.004%) | 6962 (0.011%) | 5969 (0.010%) |
| 3[2] | Clear and colorless | 5.5 | | | 1.6 | 3635 (0.006%) | 8560 (0.016%) | 10898 (0.020%) |
| 6[1] | Clear and colorless | 5.5 | 46.00 | 1.80 | 1.7 | 2453 (0.004%) | 13974 (0.023%) | 6867 (0.011%) |

| Testing time, 40° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2426 (0.004%) | 5381 (0.009%) | 15241 (0.024%) | 60560 (0.097%) | 62197853 (99.834%) | 6605 (0.011%) |
| 1[1] | 2691 (0.004%) | 4826 (0.008%) | 12928 (0.021%) | 60894 (0.098%) | 62203800 (99.815%) | 12505 (0.02%) |
| 3[2] | 2844 (0.004%) | 4836 (0.009%) | 13765 (0.025%) | 60708 (0.112%) | 53818012 (99.639%) | 31825 (0.059%) |
| 6[1] | 1818 (0.003%) | N/A | N/A | 50941 (0.085%) | 59771249 (99.816%) | 4219 (0.007%) |

[1]Performed on HPLC10
[2]Performed on HPLC12

TABLE 11A-1

(T) Additional peaks for Solution 2A formulation at 40° C. at t = 1 month.

| HPLC Purity, Area % Peak @ 5.0 min | T = 1 m extra peaks Peak @ 5.9 min | Peak @ 36.6 min |
|---|---|---|
| 2084 (0.003%) | 1503 (0.002%) | 940 (0.002%) |

TABLE 11A-2

(U) Additional peaks for Solution 2A formulation at 40° C. at t = 3 months.

| HPLC Purity, Area % Peak @ 5.7 min | T = 3 m extra peaks Peak @ 7.2 min | Peak @ 7.9 min | Peak @ 16.7 min | Peak @ 38.3 min |
|---|---|---|---|---|
| 3988 (0.007%) | 3616 (0.004%) | 13288 (0.025%) | 9899 (0.018%) | 3566 (0.004%) |

TABLE 11A-3

(V) Additional peaks for Solution 2A formulation at 40° C. at t = 6 months.

| HPLC Purity, Area % Peak @ 5.7 min | T = 3 m extra peaks Peak @ 7.2 min | Peak @ 7.9 min | Peak @ 16.7 min | Peak @ 38.3 min |
|---|---|---|---|---|
| 6021 (0.010%) | N/A | N/A | N/A | 3566 (0.004%) |

TABLE 12A (W) Summary of results for the Solution 2A formulation at 60° C.

| Testing time, 60° C. (months) | Solution 2A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 1.7 | 1667 (0.003%) | 6124 (0.010%) | 4951 (0.008%) |
| 1[1] | Cloudy, then clears up after 5 min | 5.6 | | | 1.7 | 2898 (0.005%) | 3180 (0.005%) | 3313 (0.005%) |
| 3 | | | | | | | | |
| 6 | | | | | | | | |

| Testing time, 60° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2328 (0.004%) | 5116 (0.008%) | 13236 (0.021%) | 59443 (0.096%) | 61667456 (99.837%) | 7725 (0.013%) |
| 1[1] | 2788 (0.004%) | 4.565 (0.007%) | 12218 (0.020%) | 61038 (0.098%) | 62306234 (99.768%) | 8570 (0.014%) |
| 3 | | | | | | |
| 6 | | | | | | |

[1]Performed on HPLC10

TABLE 12A-1

(X) Additional peaks for Solution 2A formulation at 60° C. at t = 1 month.

| HPLC Purity, Area % Peak @ 5.0 min | T = 1 m extra peaks Peak @ 5.1 min | Peak @ 5.56 min | Peak @ 5.9 min | Peak @ 6.9 min | Peak @ 7.4 min | Peak @ 9.0 min |
|---|---|---|---|---|---|---|
| 3173 (0.005%) | 1574 (0.003%) | 9340 (0.015%) | 8799 (0.014%) | 2986 (0.005%) | 4115 (0.007%) | 732 (0.001%) |

TABLE 13A (Y) Summary of results for the Solution 3A formulation at 5° C.

| Testing time, 5° C. (months) | Solution 3A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 0.9 | N/A (N/A) | 2228 (0.007%) | 1921 (0.006%) |
| 1 | | | | | | | | |
| 3 | | | | | | | | |
| 6[1] | Clear and colorless | 5.5 | | | 0.9 | N/A | 2341 (0.007%) | 2163 (0.006%) |

TABLE 13A-continued (Y) Summary of results for the Solution 3A formulation at 5° C.

| Testing time, 5° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 879 (0.003%) | 2539 (0.007%) | 5549 (0.016%) | 27041 (0.080%) | 33868383 (99.800%) | 27763 (0.082%) |
| 1 | | | | | | |
| 3 | | | | | | |
| 6[1] | N/A | N/A | N/A | N/A | 33243404 (99.865%) | 8292 (0.025%) |

[1]Performed on HPLC10

TABLE 14A (Z) Summary of results for the Solution 3A formulation at 25° C.

| Testing time, 25° C. (months) | Solution 3A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | 24.10 | 0.60 | 1.0 | 978 (0.003%) | 2398 (0.007%) | 1865 (0.005%) |
| 1[1] | Clear and colorless | 5.5 | | | 0.9 | 987 (0.003%) | 2880 (0.008%) | 2776 (0.008%) |
| 3[2] | Clear and colorless | 5.5 | | | 0.9 | N/A | 3139 (0.010%) | 5626 (0.018%) |
| 6[1] | Clear and colorless | 5.5 | 36.50 | 1.00 | 0.9 | N/A | 2917 (0.009%) | 2113 (0.006%) |

| Testing time, 25° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 1091 (0.003%) | 1958 (0.006%) | 5624 (0.016%) | 28586 (0.094%) | 34141239 (99.837%) | 13128 (0.038%) |
| 1[1] | 1286 (0.004%) | 2786 (0.008%) | 7128 (0.021%) | 29003 (0.085%) | 33940156 (99.829%) | 7013 (0.021%) |
| 3[2] | N/A | 2484 (0.008%) | 4551 (0.015%) | 32787 (0.106%) | 30862935 (99.646%) | 21336 (0.069%) |
| 6[1] | N/A | N/A | N/A | N/A | 33384663 (99.881%) | 3199 (0.010%) |

[1]Performed on HPLC10
[2]Performed on HPLC12

TABLE 14A-1

(AA) Additional peaks for Solution 3A formulation at 25° C. at t = 1 month.

| HPLC Purity, Area % Peak @ 4.4 min | T = 1 m extra peaks Peak @ 5.0 min | Peak @ 39.8 min |
|---|---|---|
| 987 (0.003%) | 3934 (0.012%) | 244 (0.001%) |

TABLE 14A-2

(BB) Additional peaks for Solution 3A formulation at 40° C. at t = 3 months.

| HPLC Purity, Area % Peak @ 7.9 min | T = 3 m extra peaks Peak @ 15.3 min | Peak @ 36.8 min |
|---|---|---|
| 14151 (0.046%) | 6463 (0.021%) | 6734 (0.022%) |

TABLE 15A (CC) Summary of results for the Solution 3A formulation at 40° C.

| Testing time, 40° C. (months) | Solution 3A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | 22.00 | 1.00 | 0.9 | 855 (0.003%) | 2876 (0.008%) | 2098 (0.006%) |
| 1[1] | Clear and colorless | 5.5 | | | 0.9 | 730 (0.002%) | 2941 (0.009%) | 1604 (0.005%) |
| 3[2] | Clear and colorless | 5.5 | | | 0.9 | 6789 (0.023%) | 5125 (0.017%) | 13881 (0.045%) |
| 6[1] | Clear and colorless | 5.5 | 57.90 | 1.50 | 0.9 | N/A | 8800 (0.026%) | N/A |

| Testing time, 40° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 1006 (0.003%) | 2701 (0.008%) | 7437 (0.022%) | 29878 (0.088%) | 34007216 (99.841%) | 7294 (0.080%) |
| 1[1] | 931 (0.003%) | 1592 (0.005%) | 5306 (0.016%) | 29304 (0.086%) | 33926903 (99.839%) | 10987 (0.032%) |
| 3[2] | N/A | 2261 (0.007%) | 5441 (0.018%) | 31138 (0.101%) | 30598360 (99.561%) | 21509 (0.058%) |
| 6[1] | N/A | N/A | N/A | 26116 (0.078%) | 33379272 (99.791%) | 6201 (0.019%) |

[1]Performed on HPLC10
[2]Performed on HPLC12

TABLE 15A-1

(DD) Additional peaks for Solution 3A formulation at 40° C. at t = 1 month.

| HPLC Purity, Area % Peak @ 3.1 min | T = 1 m extra peaks |
|---|---|
| 1365 (0.004%) | — |

TABLE 15A-2

(EE) Additional peaks for Solution 3A formulation at 40° C. at t = 3 months.

| HPLC Purity, Area % Peak @ 4.8 min | T = 3 m extra peaks Peak @ 5.7 min | Peak @ 7.2 min | Peak @ 8.1 min | Peak @ 16.7 min | Peak @ 36.8 min |
|---|---|---|---|---|---|
| 7856 (0.023%) | 2711 (0.008%) | 2788 (0.008%) | 3786 (0.012%) | 4299 (0.014%) | 6734 (0.022%) |

TABLE 15A-3

(FF) Additional peaks for Solution 3A formulation at 40° C. at t = 6 months.

| HPLC Purity, Area % Peak @ 5.7 min | T = 6 m extra peaks |
|---|---|
| 4261 (0.013%) | — |

TABLE 16A (GG) Summary of results for the Solution 3A formulation at 60° C.

| Testing time, 60° C. (months) | Solution 3A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 0.9 | 960 (0.003%) | 3048 (0.009%) | 2309 (0.007%) |
| 1[1] | Cloudy, then clears up after 5 min | 5.6 | | | 0.9 | 2403 (0.007%) | 3683 (0.011%) | N/A |
| 3 | | | | | | | | |
| 6 | | | | | | | | |

| Testing time, 60° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 1379 (0.004%) | 1731 (0.005%) | 5375 (0.016%) | 29049 (0.087%) | 33529633 (99.846%) | 7715 (0.023%) |
| 1[1] | 1961 (0.006%) | 1447 (0.004%) | 3041 (0.009%) | 29174 (0.085%) | 33932823 (99.249%) | 10919 (0.032%) |
| 3 | | | | | | |
| 6 | | | | | | |

[1]Performed on HPLC10

TABLE 16A-1

(HH) Additional peaks for Solution 3A formulation at 60° C. at t = 1 month.

| HPLC Purity, Area % Peak @ 3.1 min | T = 1 m extra peaks Peak @ 3.9 min | Peak @ 5.1 min | Peak @ 5.56 min | Peak @ 5.9 min | Peak @ 6.9 min | Peak @ 7.4 min | Peak @ 9.0 min | Peak @ 25.7 min |
|---|---|---|---|---|---|---|---|---|
| 163418 (0.478%) | 2403 (0.007%) | 1015 (0.003%) | 7846 (0.023%) | 5022 (0.015%) | 2962 (0.009%) | 3107 (0.009%) | 3314 (0.010%) | 14985 (0.044%) |

TABLE 17A (II) Summary of results for the Solution 3P formulation at 5° C.

| Testing time, 5° C. (months) | Solution 3P Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 0 | 609 (100%) | N/A | N/A |
| 1 | | | | | | | | |
| 3 | | | | | | | | |
| 6[1] | Clear and colorless | 5.5 | | | 0 | N/A | N/A | N/A |

| Testing time, 5° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | N/A | N/A | N/A | N/A | N/A | N/A |
| 1 | | | | | | |
| 3 | | | | | | |
| 6[1] | N/A | N/A | N/A | N/A | N/A | N/A |

[1]Performed on HPLC10

TABLE 18A (JJ) Summary of results for the Solution 3P formulation at 25° C.

| Testing time, 25° C. (months) | Solution 3P Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | 18.90 | 1.20 | 0 | N/A | N/A | N/A |
| 1[1] | Clear and colorless | 5.5 | | | 0 | 636 (100%) | N/A | N/A |
| 3[2] | Clear and colorless | 5.5 | | | 0 | N/A | N/A | 11254 (22.927%) |
| 6[1] | Clear and colorless | 5.5 | 42.90 | 2.20 | 0 | N/A | N/A | N/A |

| Testing time, 25° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | N/A | N/A | N/A | N/A | N/A | N/A |
| 1[1] | N/A | N/A | N/A | N/A | N/A | N/A |
| 3[2] | N/A | N/A | N/A | 20892 (42.562%) | N/A | 16940 (34.511%) |
| 6[1] | N/A | N/A | N/A | N/A | N/A | N/A |

[1]Performed on HPLC10
[2]Performed on HPLC12

TABLE 19A (KK) Summary of results for the Solution 3P formulation at 40° C.

| Testing time, 40° C. (months) | Solution 3P Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | 17.10 | 0.80 | 0 | N/A | N/A | N/A |
| 1[1] | Clear and colorless | 5.5 | | | 0 | 1594 (51.041%) | N/A | N/A |
| 3[2] | Clear and colorless | 5.5 | | | 0 | N/A | N/A | 9421 (12.884%) |
| 6[1] | Clear and colorless | 5.5 | 49.50 | 1.70 | 0 | N/A | N/A | N/A |

| Testing time, 40° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | N/A | N/A | N/A | N/A | N/A | N/A |
| 1[1] | N/A | N/A | N/A | N/A | N/A | N/A |
| 3[2] | N/A | N/A | N/A | 22140 (30.279%) | N/A | 25435 (34.785%) |
| 6[1] | N/A | N/A | N/A | N/A | N/A | 4955 (11.855%) |

[1]Performed on HPLC10
[2]Performed on HPLC12

TABLE 19A-1

(LL) Additional peaks for Solution 3P formulation at 40° C. at t = 1 month.

| HPLC Purity, Area % Peak @ 3.1 min | T = 1 m extra peaks |
|---|---|
| 1529 (48.959%) | — |

TABLE 19A-2

(MM) Additional peaks for Solution 3P formulation at 40° C. at t = 3 months.

| HPLC Purity, Area % Peak @ 22.8 min | T = 3 m extra peaks |
|---|---|
| 14492 (19.819%) | — |

TABLE 19A-3

(NN) Additional peaks for Solution 3P formulation at 40° C. at t = 6 months.

| HPLC Purity, Area % Peak @ 33.8 min | T = 6 m extra peaks |
|---|---|
| 3722 (8.905%) | — |

TABLE 20A (OO) Summary of results for the Solution 3P formulation at 60° C.

| Testing time, 60° C. (months) | Solution 3P Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 0 | N/A | N/A | N/A |
| 1[1] | Cloudy, then clears up after 5 min | 5.5 | | | 0 | N/A | N/A | N/A |
| 3 | | | | | | | | |
| 6 | | | | | | | | |

| Testing time, 60° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | N/A | N/A | N/A | N/A | N/A | N/A |
| 1[1] | N/A | N/A | N/A | N/A | N/A | 10919 (0.032%) |
| 3 | | | | | | |
| 6 | | | | | | |

[1]Performed on HPLC10

TABLE 20A-1

(PP) Additional peaks for Solution 3P formulation at 60° C. at t = 1 month.

| HPLC Purity, Area % Peak @ 3.1 min | T = 6 m extra peaks |
|---|---|
| 190906 (93.021%) | — |

TABLE 21A (QQ) Summary of results for the Solution 4A formulation at 5° C.

| Testing time, | Solution 3A | | Average Particles Per | Average Particles Per | Conc., | HPLC Purity, Area % |
|---|---|---|---|---|---|---|

TABLE 21A-continued (QQ) Summary of results for the Solution 4A formulation at 5° C.

| 5° C. (months) | Attribute Appearance | pH | Container 10.000 μm | Container 25.000 μm | HPLC (mg/ml) | Peak 1, 4.4 min | Peak 2, 5.6 min | Peak 3, 8.4 min |
|---|---|---|---|---|---|---|---|---|
| 0[1] | Clear and colorless | 5.5 | | | 1.7 | 1436 (0.002%) | 4012 (0.006%) | 4102 (0.007%) |
| 1 | | | | | | | | |
| 3 | | | | | | | | |
| 6[1] | Clear and colorless | 5.5 | | | 1.7 | N/A | 4220 (0.007%) | 5189 (0.009%) |

| Testing time, 5° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2436 (0.004%) | 5104 (0.008%) | 13313 (0.021%) | 61130 (0.098%) | 61955043 (99.811%) | 25823 (0.042%) |
| 1 | | | | | | |
| 3 | | | | | | |
| 6[1] | 1915 (0.003%) | N/A | N/A | 59398 (0.100%) | 59297216 (99.829%) | 7233 (0.012%) |

[1] Performed on HPLC10

TABLE 22A (RR) Summary of results for the Solution 4A formulation at 25° C.

| Testing time, 25° C. (months) | Solution 3A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | 19.60 | 0.80 | 1.7 | 1609 (0.003%) | 4274 (0.007%) | 4316 (0.007%) |
| 1[1] | Clear and colorless | 5.5 | | | 1.7 | 2691 (0.004%) | 4756 (0.008%) | 5615 (0.009%) |
| 3[2] | Clear and colorless | 5.5 | | | 1.6 | 2867 (0.004%) | 5164 (0.010%) | 11833 (0.025%) |
| 6[1] | Clear and colorless | 5.5 | 31.80 | 2.90 | 1.7 | N/A | 4892 (0.008%) | 6113 (0.010%) |

| Testing time, 25° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2568 (0.004%) | 4916 (0.008%) | 13545 (0.022%) | 62372 (0.100%) | 62035143 (99.836%) | 8603 (0.014%) |
| 1[1] | 2490 (0.004%) | 4918 (0.008%) | 12873 (0.021%) | 61607 (0.099%) | 61851541 (99.813%) | 18960 (0.031%) |
| 3[2] | 3338 (0.005%) | 5333 (0.010%) | 9917 (0.019%) | 62318 (0.116%) | 5339537 (99.667%) | 24907 (0.046%) |
| 6[1] | 2011 (0.003%) | N/A | N/A | 54274 (0.091%) | 59415139 (99.836%) | 5796 (0.010%) |

[1] Performed on HPLC10
[2] Performed on HPLC12

TABLE 22A-1

(SS) Additional peaks for Solution 4A formulation at 25° C. at t = 1 month.

| HPLC Purity, Area % Peak @ 36.6 min | T = 1 m extra peaks |
|---|---|
| 880 (0.001%) | — |

TABLE 22A-2

(TT) Additional peaks for Solution 4A formulation at 25° C. at t = 3 months.

| HPLC Purity, Area % Peak @ 7.2 min | T = 3 m extra peaks Peak @ 7.9 min | Peak @ 8.8 min | Peak @ 15.3 min | Peak @ 36.8 min |
|---|---|---|---|---|
| 2566 (0.004%) | 13469 (0.025%) | 3338 (0.005%) | 13647 (0.025%) | 11556 (0.022%) |

TABLE 23A (UU) Summary of results for the Solution 4A formulation at 40° C.

| Testing time, 40° C. (months) | Solution 3A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.6 | 73.00 | 14.00 | 1.7 | 1396 (0.002%) | 4399 (0.007%) | 4249 (0.007%) |
| 1[1] | Clear and colorless | 5.5 | | | 1.7 | 1444 (0.002%) | 6005 (0.010%) | 5383 (0.009%) |
| 3[2] | Clear and colorless | 5.5 | | | 1.6 | 9735 (0.018%) | 8725 (0.016%) | 12070 (0.023%) |
| 6[1] | Clear and colorless | 5.5 | 64.10 | 3.40 | 1.7 | 2344 (0.004%) | 16305 (0.027%) | 3594 (0.006%) |

| Testing time, 40° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2491 (0.004%) | 5032 (0.008%) | 13525 (0.022%) | 60955 (0.098%) | 61808714 (99.843%) | 4932 (0.008%) |
| 1[1] | 2371 (0.004%) | 4766 (0.008%) | 14950 (0.024%) | 64181 (0.103%) | 61911629 (99.814%) | 12508 (0.020%) |
| 3[2] | 3279 (0.005%) | 5247 (0.010%) | 13313 (0.025%) | 60741 (0.113%) | 53343311 (99.557%) | 30494 (0.057%) |
| 6[1] | 3534 (0.006%) | N/A | N/A | 26386 (0.044%) | 59466240 (99.792%) | 5071 (0.009%) |

[1]Performed on HPLC10
[2]Performed on HPLC12

TABLE 23A-1

(VV) Additional peaks for Solution 4A formulation at 40° C. at t = 1 month.

| HPLC Purity, Area % Peak @ 5.9 min | T = 1 m extra peaks Peak @ 36.6 min |
|---|---|
| 1982 (0.003%) | 1001 (0.002%) |

TABLE 23A-2

(WW) Additional peaks for Solution 4A formulation at 40° C. at t = 3 months.

| HPLC Purity, Area % Peak @ 4.8 min | T = 3 m extra peaks Peak @ 4.9 min | Peak @ 5.5 min | Peak @ 5.7 min | Peak @ 6.7 min | Peak @ 7.2 min | Peak @ 7.9 min | Peak @ 16.7 min | Peak @ 38.3 min |
|---|---|---|---|---|---|---|---|---|
| 5243 (0.009%) | 2166 (0.004%) | 2835 (0.005%) | 5989 (0.011%) | 3727 (0.007%) | 10449 (0.019%) | 18748 (0.035%) | 9702 (0.018%) | 7206 (0.014%) |

TABLE 23A-3

(XX) Additional peaks for Solution 4A formulation at 40° C. at t = 6 months.

| HPLC Purity, Area % Peak @ 5.7 min | T = 6 m extra peaks Peak @ 33.9 min | Peak @ 39.8 min |
|---|---|---|
| 9446 (0.016%) | 2487 (0.004%) | 2507 (0.004%) |

TABLE 24A (YY) Summary of results for the Solution 4A formulation at 60° C.

| Testing time, 60° C. (months) | Solution 3A Attribute Appearance | pH | Average Particles Per Container 10.000 μm | Average Particles Per Container 25.000 μm | Conc., HPLC (mg/ml) | HPLC Purity, Area % Peak 1, 4.4 min | Peak 2, 5.6 min | Peak 3, 8.4 min |
|---|---|---|---|---|---|---|---|---|
| 0[1] | Clear and colorless | 5.5 | | | 1.7 | 1381 (0.002%) | 4731 (0.008%) | 4848 (0.008%) |
| 1[1] | Clear and colorless | 5.6 | | | 1.7 | 6290 (0.010%) | 9546 (0.015%) | 1982 (0.003%) |
| 3 | | | | | | | | |
| 6 | | | | | | | | |

| Testing time, 60° C. (months) | Peak 4, 9.1 min | Peak 5, 13.6 min | Peak 6, 16.8 min | Peak 7, 20.5 min | Capsaicin 20.9 min | Peak 8, 37.7 min |
|---|---|---|---|---|---|---|
| 0[1] | 2488 (0.004%) | 5365 (0.009%) | 12924 (0.021%) | 60663 (0.098%) | 61567424 (99.828%) | 8644 (0.014%) |
| 1[1] | 4376 (0.007%) | 4675 (0.008%) | 9876 (0.016%) | 61931 (0.100%) | 61706951 (99.391%) | 11857 (0.019%) |
| 3 | | | | | | |
| 6 | | | | | | |

[1]Performed on HPLC10

TABLE 24A-1

(ZZ) Additional peaks for Solution 4A formulation at 60° C. at t = 1 month.

| HPLC Purity, Area % Peak @ 3.1 min | T = 1 m extra peaks Peak @ 3.9 min | Peak @ 5.0 min | Peak @ 5.1 min | Peak @ 5.56 min | Peak @ 5.9 min | Peak @ 6.9 min |
|---|---|---|---|---|---|---|
| 158505 (0.255%) | 5348 (0.009%) | 6645 (0.011%) | 5154 (0.008%) | 15935 (0.026%) | 11537 (0.019%) | 7720 (0.012%) |

| Peak @ 7.4 min | Peak @ 9.0 min | Peak @ 18.8 min | Peak @ 25.7 min | Peak @ 34.3 min | Peak @ 36.6 min | Peak @ 39.8 min |
|---|---|---|---|---|---|---|
| 8282 (0.013%) | 6672 (0.011%) | 9415 (0.015%) | 21701 (0.035%) | 3589 (0.006%) | 808 (0.001%) | 5264 (0.008%) |

Example 3—Preparation of Additional Exemplary Capsaicin Aqueous Formulations Three additional exemplary stable aqueous capsaicin injectable formulations were prepared. Experimental procedures and results are provided below.

Part I—Preparation of First Exemplary Additional Formulation

The formulation listed in the table below was prepared by the following procedure:

(a) Place 900 mL of water in a vessel;
(b) Add 6.80 grams of sodium acetate to the vessel containing water;
(c) Adjust solution pH to 5.5 by adding 1N HCl;
(d) Add 10.0 grams of Kolliphor HS 15 to the solution [the Kolliphor HS 15 has CAS Registry No 70142-34-6, and is a mixture containing (a) about 70% (w/w) of a mixture of

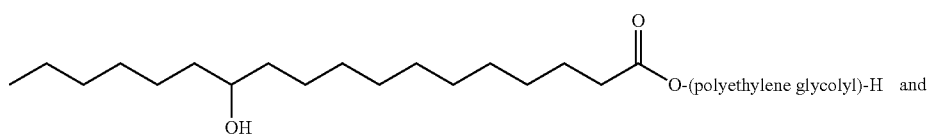

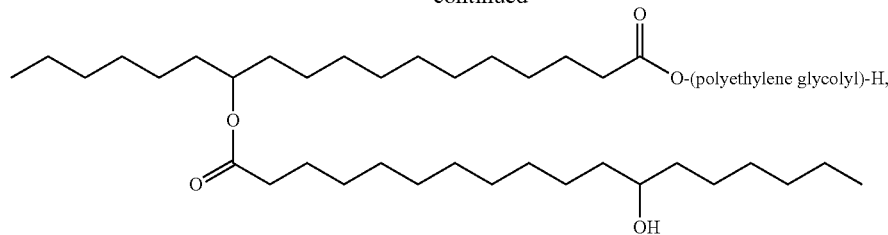

and (b) about 30% (w/w) polyethylene glycol; where the polyethylene glycolyl has a weight-average molecular weight of about 660 g/mol; which is sold and marketed by BASF as KOLLIPHOR® HS 15];
(e) Add 0.10 grams of dibutylhydroxytoluene to the solution, and let the solution age for at least 2 hours;
(f) Add 0.25 grams of ethylenediaminetetraacetic acid tetrasodium salt to the solution;
(g) Add 0.50 grams of trans-capsaicin to the solution, and age the solution until the trans-capsaicin dissolves;
(h) Add 6.0 grams of NaCl to the solution;
(i) Adjust pH of the solution to pH=5.5 by adding 1N HCl or 1N NaOH as needed;
(j) q.s. with water so the volume of the solution reaches 1 liter; and
(k) Sterile filter the solution.

| Formulation |
|---|
| An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>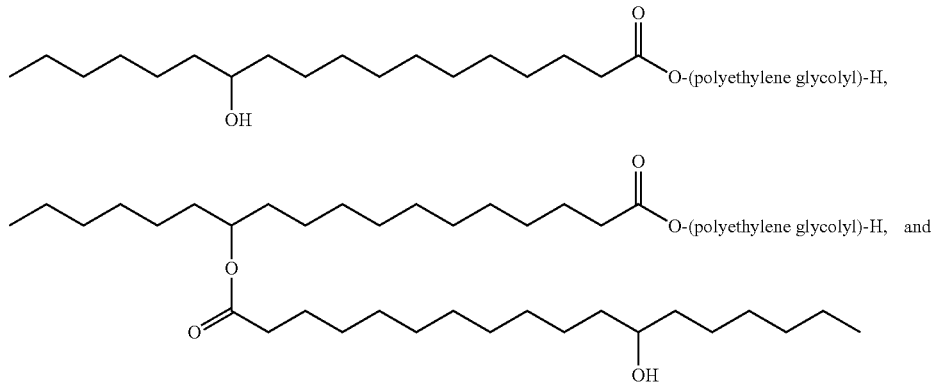<br>polyethylene glycol; wherein the polyethylene glycolyl has a weight average molecular weight of about 660 g/mol;<br>c. 0.01% (w/w) dibutylhydroxytoluene;<br>d. 0.68% (w/w) of sodium acetate or a mixture of sodium acetate and acetic acid;<br>e. 0.025% (w/w) of ethylenediaminetetraacetic acid or a salt thereof;<br>f. 0.6% (w/w) of sodium chloride;<br>g. q.s. with water (i.e., least 97.6% (w/w)); and<br>having a pH of 5.5. |

Part II—Preparation of Second Exemplary Additional Formulation

The formulation listed in the table below was prepared by the following procedure:
(a) Place 900 mL of water in a vessel;
(b) Add 3.40 grams of sodium acetate to the vessel containing water;
(c) Adjust solution pH to 5.5 by adding 1N HCl;
(d) Add 10.0 grams of Kolliphor HS 15 to the solution [the Kolliphor HS 15 has CAS Registry No 70142-34-6, and is a mixture containing (a) about 70% (w/w) of a mixture of

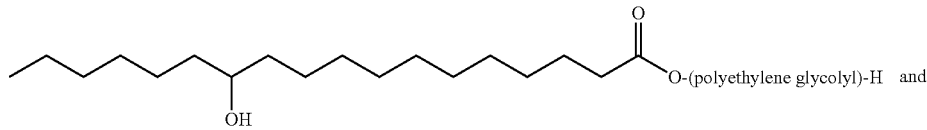

-continued

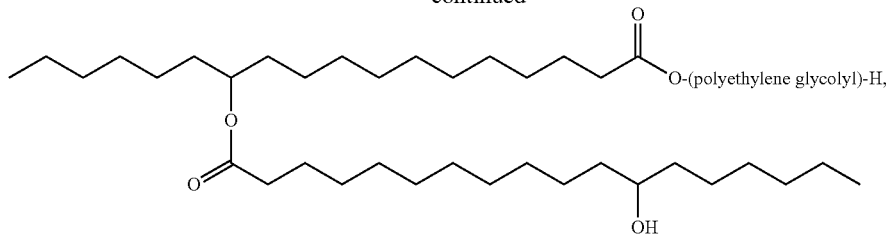

and (b) about 30% (w/w) polyethylene glycol; where the polyethylene glycolyl has a weight-average molecular weight of about 660 g/mol; which is sold and marketed by BASF as KOLLIPHOR® HS 15];
(e) Add 0.10 grams of dibutylhydroxytoluene to the solution, and let the solution age for at least 2 hours;
(f) Add 0.25 grams of ethylenediaminetetraacetic acid tetrasodium salt to the solution;
(g) Add 0.50 grams of trans-capsaicin to the solution, and age the solution until the trans-capsaicin dissolves;
(h) Add 7.5 grams of NaCl to the solution;
(i) Adjust pH of the solution to pH=5.5 by adding 1N HCl or 1N NaOH as needed;
(j) q.s. with water so the volume of the solution reaches 1 liter; and
(k) Sterile filter the solution.

| Formulation |
|---|
| An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>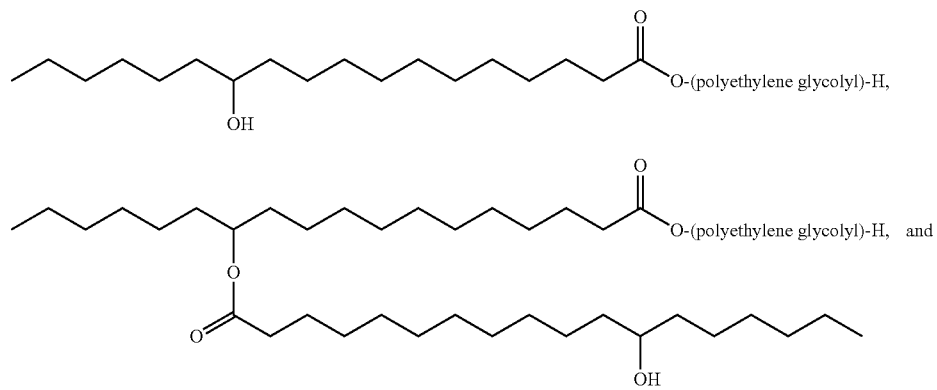<br>polyethylene glycol; wherein the polyethylene glycolyl has a weight average molecular weight of about 660 g/mol;<br>c. 0.01% (w/w) dibutylhydroxytoluene;<br>d. 0.34% (w/w) of sodium acetate or a mixture of sodium acetate and acetic acid;<br>e. 0.025% (w/w) of ethylenediaminetetraacetic acid or a salt thereof;<br>f. 0.75% (w/w) of sodium chloride;<br>g. q.s. with water (i.e., least 97.8% (w/w)); and<br>having a pH of 5.5. |

Part III—Preparation of Third Exemplary Additional Formulation

The formulation listed in the table below was prepared by the following procedure:
(a) Place 900 mL of water in a vessel;
(b) Add 2.2 grams of trisodium citrate dihydrate to the vessel containing water;
(c) Adjust solution pH to 5.5 by adding 1N HCl;
(d) Add 10.0 grams of Kolliphor HS 15 to the solution [the Kolliphor HS 15 has CAS Registry No 70142-34-6, and is a mixture containing (a) about 70% (w/w) of a mixture of

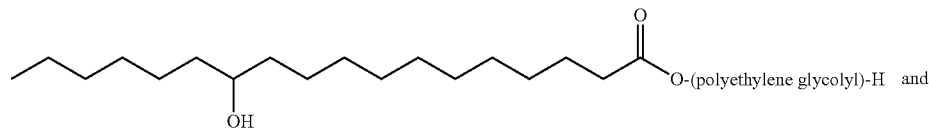

-continued

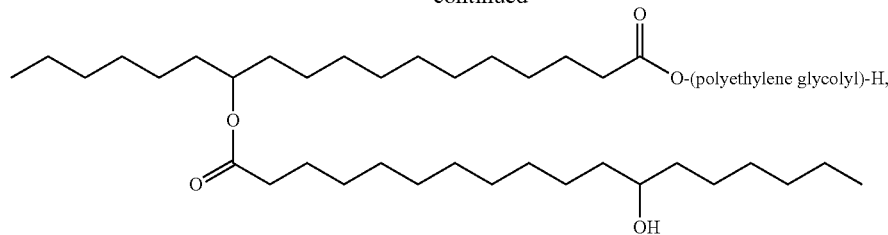

and (b) about 30% (w/w) polyethylene glycol; where the polyethylene glycolyl has a weight-average molecular weight of about 660 g/mol; which is sold and marketed by BASF as KOLLIPHOR® HS 15];
(e) Add 0.10 grams of dibutylhydroxytoluene to the solution, and let the solution age for at least 2 hours;
(f) Add 0.25 grams of ethylenediaminetetraacetic acid tetrasodium salt to the solution;
(g) Add 0.50 grams of trans-capsaicin to the solution, and age the solution until the trans-capsaicin dissolves;
(h) Add 8.0 grams of NaCl to the solution;
(i) Adjust pH of the solution to pH=5.5 by adding 1N HCl or 1N NaOH as needed;
(j) q.s. with water so the volume of the solution reaches 1 liter; and
(k) Sterile filter the solution.

| Formulation |
|---|
| An aqueous, capsaicin injectable formulation, comprising:<br>a. 0.05% (w/w) of trans-capsaicin;<br>b. 1% (w/w) of a solubilizing agent, wherein the solubilizing agent is a mixture of<br>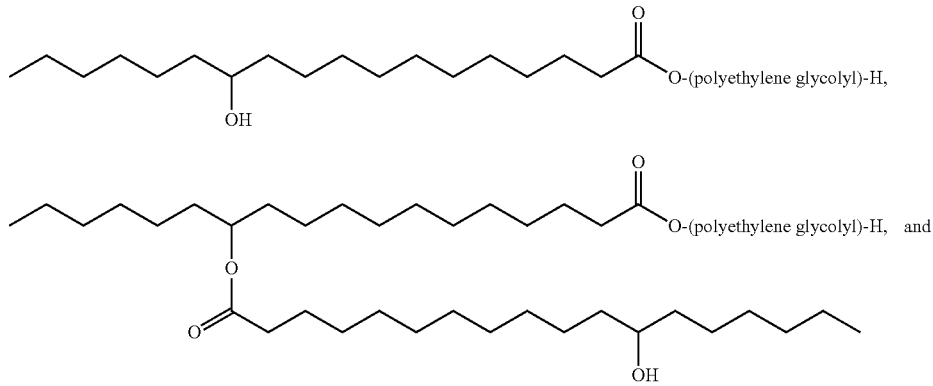<br>polyethylene glycol; wherein the polyethylene glycolyl has a weight average molecular weight of about 660 g/mol;<br>c. 0.01% (w/w) dibutylhydroxytoluene;<br>d. 0.22% (w/w) of sodium citrate or a mixture of sodium citrate and citric acid;<br>e. 0.025% (w/w) of ethylenediaminetetraacetic acid or a salt thereof;<br>f. 0.8% (w/w) of sodium chloride;<br>g. q.s. with water (i.e., 97.9% (w/w) water); and<br>having a pH of 5.5. |

Example 4—Analysis of Capsaicin Solubility in Multiple Aqueous Formulations Containing a Solubilizing Agent Multiple aqueous formulations were prepared and analyzed to determine the amount of dissolved capsaicin. The formulations contained differing amounts of the solubilizing agent Kolliphor HS 15 to increase the amount of capsaicin dissolved in the aqueous medium. The experimental procedures and results are described below.

Experimental Procedures

The equilibrium solubility of capsaicin was determined in a series of aqueous solutions. Eight different solutions were prepared, as described in Table 10 below, and the amount of dissolved capsaicin was determined. All eight solutions had a pH of 5.5. Kolliphor HS 15 has CAS Registry No. 70142-34-6, and is a mixture containing (a) about 70% (w/w) of a mixture of

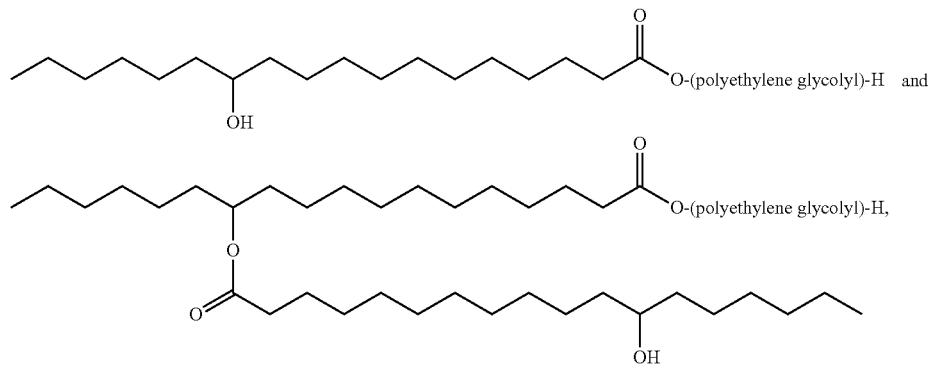

and (b) about 30% (w/w) polyethylene glycol; where the polyethylene glycolyl has a weight-average molecular weight of about 660 g/mol; which is sold and marketed by BASF as KOLLIPHOR® HS 15.

TABLE 10

| No. | Amount of Kolliphor HS 15 (w/v) | Observed Dissolved Capsaicin (mg/mL) | Other Components (w/v) |
|---|---|---|---|
| 1 | 1% | 0.958 | 0.9% NaCl, 0.1% EDTA, 0.01% butylated hydroxytoluene, and 20 mM Citrate Buffer. |
| 2 | 2% | 1.68 | 0.9% NaCl, 0.1% EDTA, 0.01% butylated hydroxytoluene, and 20 mM Citrate Buffer. |
| 3 | 4% | 2.47 | 0.9% NaCl, 0.1% EDTA, 0.01% butylated hydroxytoluene, and 20 mM Citrate Buffer. |
| 4 | 5% | 3.76 | 0.9% NaCl, 0.1% EDTA, 0.01% butylated hydroxytoluene, and 20 mM Citrate Buffer. |
| 5 | 1% | 1.05 | 5% Dextrose, 0.1% EDTA, 0.01% butylated hydroxytoluene, and 20 mM Citrate Buffer. |
| 6 | 2% | 1.70 | 5% Dextrose, 0.1% EDTA, 0.01% butylated hydroxytoluene, and 20 mM Citrate Buffer. |
| 7 | 4% | 2.67 | 5% Dextrose, 0.1% EDTA, 0.01% butylated hydroxytoluene, and 20 mM Citrate Buffer. |
| 8 | 5% | 3.78 | 5% Dextrose, 0.1% EDTA, 0.01% butylated hydroxytoluene, and 20 mM Citrate Buffer. |

Example 5—Twenty-Six Month Stability Analysis for Exemplary Formulations

The formulations in Table 11 below were subjected to stability analysis by storage for twenty-six (26) months at the conditions specified below (i.e., 25° C. at 60% relative humidity, or 40° C. at 75% relative humidity), followed by analytical analysis to determine the amount of trans-capsaicin and any detectable impurities in the formulation. Results are presented in Tables 12-15 below.

The abbreviation BHT refers to dibutylhydroxytoluene. The abbreviation "EDTA" refers to ethylenediaminetetraacetic acid. The abbreviation "ND" refers to not detected. The Kolliphor HS-15 has CAS Registry No 70142-34-6, and is a mixture containing (a) about 70% (w/w) of a mixture of

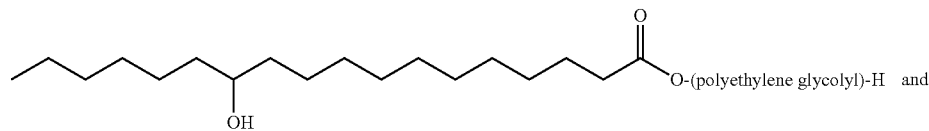

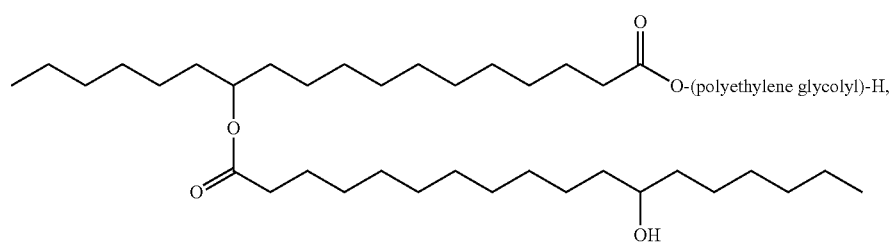

and (b) about 30% (w/w) polyethylene glycol; where the polyethylene glycolyl has a weight-average molecular weight of about 660 g/mol; which is sold and marketed by BASF as KOLLIPHOR® HS 15. The phrase "Average Particles Per Container" refers to the average number of particles observed in a container, where the container held approximately 1.5 mL of aqueous formulation to be analyzed. Dimer 1 Impurity has the following chemical structure:

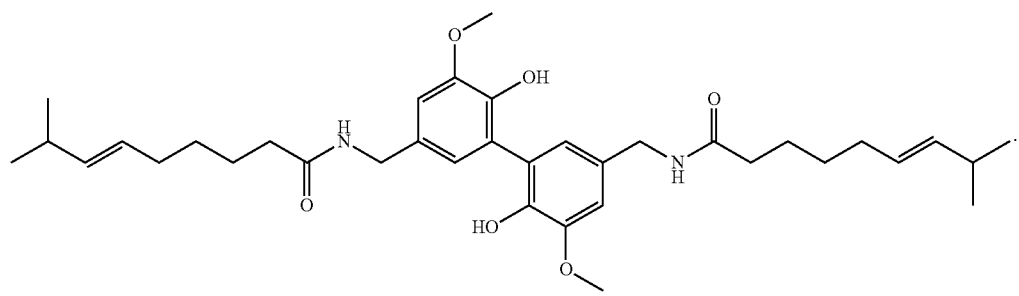 [SMILES: COc1cc(CNC(=O)CCCC/C=C/C(C)C)cc(-c2cc(CNC(=O)CCCC/C=C/C(C)C)cc(OC)c2O)c1O]

Dimer 2 Impurity is believed to have one of the following chemical structures:

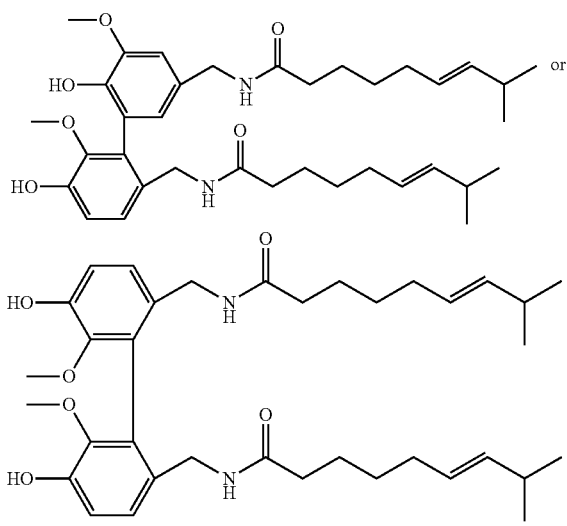

5-Oxo-capsaicin has the following chemical structure:

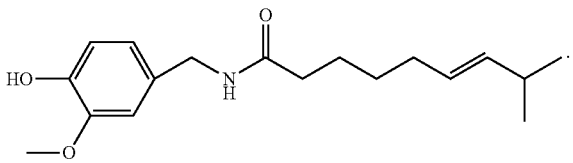 [SMILES: COc1cc(CNC(=O)CCCC/C=C/C(C)C)ccc1O]

TABLE 11

| Formulation 1A | Formulation 2A |
|---|---|
| 1 mg/mL trans-capsaicin | 2 mg/mL trans-capsaicin |
| 2% (wt/wt) Kolliphor HS-15 | 4% (wt/wt) Kolliphor HS-15 |
| 20 mM citrate buffer | 20 mM citrate buffer |

TABLE 11-continued

| Formulation 1A | Formulation 2A |
|---|---|
| 0.1% (wt/wt) disodium EDTA | 0.1% (wt/wt) disodium EDTA |
| 0.01% (wt/wt) BHT | 0.01% (wt/wt) BHT |
| 0.625% (wt/wt) NaCl | 0.625% (wt/wt) NaCl |
| q.s. water | q.s. water |

TABLE 12

Summary of Results from Storage of Formulation 1A for 26 Months at 25° C./60% Relative Humidity

| Analytical Feature | Observed Result at Time = 0 Months | Observed Result at Time = 26 Months |
|---|---|---|
| Appearance | clear and colorless | clear and colorless |
| pH of the solution | 5.5 | 5.35 |
| Average Number of Particles Having Size ≥10 μM Per Container | 19.4 | 583 |
| Average Number of Particles Having Size ≥25 μM Per Container | 1.1 | 235 |
| Concentration of trans-capsaicin (mg/mL) as determined by HPLC analysis | 1.0 | 0.99 |
| Concentration of BHT (mg/mL) | Not tested | 0.0108 |

| Purity Analysis by HPLC | | |
|---|---|---|
| Analyte | \multicolumn{2}{c}{Detected Amount According to Percent Area of HPLC Plot (area %)} |
| Impurity at RRT 0.27 in HPLC Plot | 0.01 | ND |
| 5-oxo-capsaicin | 0.01 | 0.06 |
| Impurity at RRT 0.80 in HPLC Plot | 0.02 | 0.06 |
| cis-capsaicin | 0.01 | 0.08 |
| trans-capsaicin | 99.80 | 99.8 |
| Dimer 1 Impurity | 0.02 | ND |
| Dimer 2 Impurity | ND | ND |

TABLE 13

Summary of Results from Storage of Formulation 1A for 26 Months at 40° C./75% Relative Humidity

| Analytical Feature | Observed Result at Time = 0 Months | Observed Result at Time = 26 Months |
|---|---|---|
| Appearance | clear and colorless | slightly opaque, no visible particles |
| pH of the solution | 5.5 | 5.40 |
| Average Number of Particles | 45.8 | 583 |

TABLE 13-continued

Summary of Results from Storage of Formulation 1A for 26 Months at 40° C./75% Relative Humidity

| | | |
|---|---|---|
| Having Size ≥10 μM Per Container | | |
| Average Number of Particles | 2.0 | 235 |
| Having Size ≥25 μM Per Container | | |
| Concentration of trans-capsaicin (mg/mL) as determined by HPLC analysis | 1.0 | 1.0 |
| Concentration of BHT (mg/mL) | Not tested | 0.0108 |

Purity Analysis by HPLC

| Analyte | Detected Amount According to Percent Area of HPLC Plot (area %) | |
|---|---|---|
| Impurity at RRT 0.27 in HPLC Plot | 0.01 | ND |
| 5-oxo-capsaicin | 0.01 | 0.06 |
| Impurity at RRT 0.80 in HPLC Plot | 0.02 | 0.06 |
| cis-capsaicin | 0.01 | 0.09 |
| trans-capsaicin | 99.80 | 99.75 |
| Dimer 1 Impurity | 0.02 | 0.02 |
| Dimer 2 Impurity | ND | 0.01 |

TABLE 14

Summary of Results from Storage of Formulation 2A for 26 Months at 25° C./60% Relative Humidity

| Analytical Feature | Observed Result at Time = 0 Months | Observed Result at Time = 26 Months |
|---|---|---|
| Appearance | clear and colorless | clear and colorless |
| pH of the solution | 5.6 | 5.41 |
| Average Number of Particles Having Size ≥10 μM Per Container | 16.6 | 759 |
| Average Number of Particles Having Size ≥25 μM Per Container | 0.4 | 611 |
| Concentration of trans-capsaicin (mg/mL) as determined by HPLC analysis | 1.7 | 1.7 |
| Concentration of BHT (mg/mL) | Not tested | 0.010 |

Purity Analysis by HPLC

| Analyte | Detected Amount According to Percent Area of HPLC Plot (area %) | |
|---|---|---|
| Impurity at RRT 0.27 in HPLC Plot | 0.01 | ND |
| 5-oxo-capsaicin | 0.01 | 0.04 |
| Impurity at RRT 0.80 in HPLC Plot | 0.02 | 0.07 |
| cis-capsaicin | 0.10 | 0.09 |
| trans-capsaicin | 99.82 | 99.79 |
| Dimer 1 Impurity | 0.003 | 0.01 |
| Dimer 2 Impurity | ND | ND |

TABLE 15

Summary of Results from Storage of Formulation 2A for 26 Months at 40° C./75% Relative Humidity

| Analytical Feature | Observed Result at Time = 0 Months | Observed Result at Time = 26 Months |
|---|---|---|
| Appearance | clear and colorless | Slightly opaque, no visible particles |
| pH of the solution | 5.6 | 5.40 |
| Average Number of Particles Having Size ≥10 μM Per Container | 10.9 | 3471 |
| Average Number of Particles Having Size ≥25 μM Per Container | 0.8 | 458 |
| Concentration of trans-capsaicin (mg/mL) as determined by HPLC analysis | 1.7 | 1.7 |
| Concentration of BHT (mg/mL) | Not tested | 0.010 |

Purity Analysis by HPLC

| Analyte | Detected Amount According to Percent Area of HPLC Plot (area %) | |
|---|---|---|
| Impurity at RRT 0.27 in HPLC Plot | 0.006 | ND |
| 5-oxo-capsaicin | 0.005 | 0.03 |
| Impurity at RRT 0.80 in HPLC Plot | 0.018 | 0.07 |
| cis-capsaicin | 0.088 | 0.09 |
| trans-capsaicin | 99.83 | 99.71 |
| Dimer 1 Impurity | 0.01 | 0.08 |
| Dimer 2 Impurity | ND | 0.02 |

Example 6—Preparation of Additional Exemplary Capsaicin Aqueous Formulation

The aqueous capsaicin injectable formulation labeled as Capsaicin Formulation 1 in the following table was prepared. Experimental procedures are provided below.

| Capsaicin Formulation 1 |
|---|
| An aqueous, capsaicin injectable formulation containing:<br>a. 0.05% (w/w) of trans-capsaicin;<br>b. 1% (w/w) of macrogol 15 hydroxystearate;<br>c. 0.01% (w/w) dibutylated hydroxytoluene;<br>d. 50 mM of buffer that is a mixture of sodium acetate and acetic acid;<br>e. 0.025% (w/w) of ethylenediaminetetraacetic acid or a salt thereof;<br>f. 0.6% (w/w) of sodium chloride;<br>g. q.s. with water (i.e., about 97.6% (w/w)); and<br>having a pH of 5.5. |

Experimental Procedures

Butylated hydroxytoluene (BHT) and macrogol 15 hydroxystearate are added and slightly warmed (to facilitate melting) and then mixed until dissolved to provide a BHT/Macrogol solution.

In a separate container, ethylenediaminetetraacetic acid (EDTA) is dissolved in water for injection (WFI). The resulting EDTA/WFI solution is added to the BHT/Macrogol solution while mixing. To the resulting solution is added trans-capsaicin and the resulting mixture is mixed for a minimum of 4 hours until a uniform solution is achieved (hereinafter "Capsaicin Solution").

In a separate container, sodium acetate trihydrate and sodium chloride are dissolved in WFI and the pH of the solution is adjusted to a pH of about 5.5. To this solution is added the necessary amount of Capsaicin Solution and the resulting solution is adjusted to weight with WFI. The pH is measured and adjusted with hydrochloric acid as necessary to achieve a pH of 5.5±0.05. The resulting solution is mixed to assure homogeneity. Then, the solution is aseptically filtered through two 0.2 micron sterilizing filters that are tested both before use and after use for integrity, to thereby provide Capsaicin Formulation 1.

Macrogol 15 hydroxystearate has CAS Registry No 70142-34-6, and is a mixture containing (a) about 70% (w/w) of a mixture of

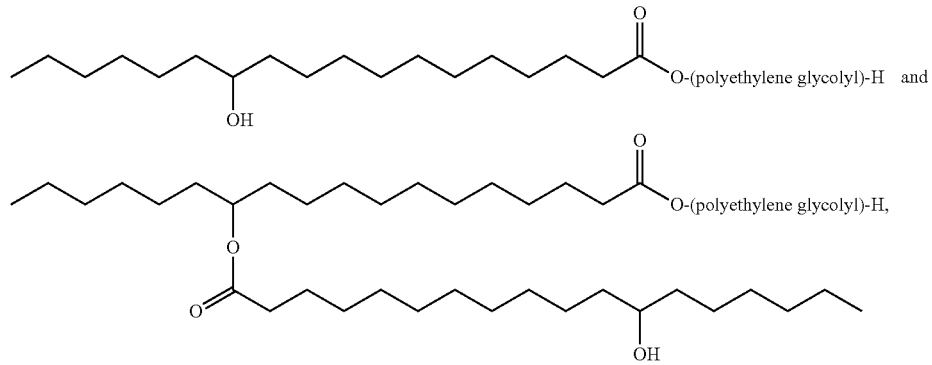

and (b) about 30% (w/w) polyethylene glycol; where the polyethylene glycolyl has a weight-average molecular weight of about 660 g/mol; which is sold and marketed by BASF as KOLLIPHOR® HS 15.

Example 7—Assessment of Toxicity for Exemplary Capsaicin Formulation Upon Administration to Rabbits An aliquot of Capsaicin Formulation A was subjected to toxicity evaluation in rabbits. Experimental Procedures and results are provided below.
Part I—Experimental Procedures for Toxicity Analysis in Rabbits An aliquot of Capsaicin Formulation A was administered as a single dose via intraarticular injection to rabbits, and analysis was performed to check for evidence of toxicity. Capsaicin Formulation A was prepared based on procedures described above for Capsaicin Formulation 1, and a description of Capsaicin Formulation A is provided in the following table.

| Capsaicin Formulation A |
|---|
| An aqueous, capsaicin injectable formulation containing:<br>a. 0.05% (w/w) of trans-capsaicin;<br>b. 1% (w/w) of macrogol 15 hydroxystearate;<br>c. 0.01% (w/w) dibutylated hydroxytoluene;<br>d. 50 mM of buffer that is a mixture sodium acetate and acetic acid;<br>e. 0.025% (w/w) of ethylenediaminetetraacetic acid or a salt thereof;<br>f. 0.6% (w/w) of sodium chloride;<br>g. q.s. with water (i.e., about 97.6% (w/w)); and<br>having a pH of 5.5. |

Procedurally, thirteen male and fourteen female New Zealand White rabbits were received from Covance Research Products, Inc. (Denver, Pa.). Animals were acclimated to the test facility for 14 days prior to initiation. At initiation of dosing, animals were 6 to 7 months old, and body weights ranged from 3060 g to 3587 g for males and 2923 to 3527 g for females. Animals not used in the study were removed from the study room. Males were individually housed in stainless steel cages without plastic bottoms. When possible, females were pair-housed in stainless steel cages, with plastic bottoms. Animals were individually housed during the pre-dose phase (females pair-housed upon arrival), and for behavior reasons. Water was provided ad libitum. Upon receipt, animals were presented with increasing amounts of Certified Rabbit Diet #5325 (PMI NUTRITION INTERNATIONAL CERTIFIED LABDIET®) once daily during the first week following arrival until acclimated to approximately 150 g/day. Animals were maintained on approximately 150 g/day of Certified Rabbit Diet #5325 until study termination.

The male and female New Zealand White rabbits were assigned to three groups, and doses of Capsaicin Formulation A were administered as indicated in the following table.

| Group | No. of Animals | | Dose of trans-Capsaicin (mg) | Dose Volume (mL) | Concentration of Capsaicin in the Dose (mg/mL) |
|---|---|---|---|---|---|
| | Male | Female | | | |
| 1 (control) | 4 | 4 | 0 | 0.6 | 0 |
| 2 | 4 | 4 | 0.1 | 0.2 | 0.5 |
| 3 | 4 | 4 | 0.3 | 0.6 | 0.5 |

Animals were administered a single dose of test article (i.e., Capsaicin Formulation A, or placebo) on Day 1 via intra-articular injection into the right stifle joint. Dosing was followed by an observation period of 4 weeks. The vehicle control article (i.e., placebo) was the same as Capsaicin Formulation A except that it did not contain capsaicin. Prior to injection of test article, animals were sedated via gas anesthesia with sevoflurane. The gas was administered by designated technicians using a nose cone. Following anesthesia but prior to intra-articular injection, the injection site was prepared aseptically with three or more chlorhexidine scrubs, wiping with sterile water between each scrub. Animals were administered 1 mg/kg of midazolam and 0.6 mg/kg of meloxicam SR subcutaneously prior to gas anesthesia. A bland ophthalmic ointment was applied to both eyes, and the right stifle joint area was clipped free of hair. Animals were positioned in dorsal recumbency, with the leg held up to allow for surgical scrub. The arthrocentesis site was prepared aseptically with three chlorhexidine scrubs, wiping with sterile water between each scrub. The right stifle joint was flexed prior to positioning the joint at an approximate 90° angle with one hand. The patella was located, and the appropriate site for arthrocentesis was palpated with a sterile, gloved hand. A 25 G×⅝ inch needle (25 G to 23 G depending on the test article) was used to enter the joint midway between the proximal aspect of the patella and the tibial tuberosity on the lateral side of the stifle joint. The needle was directed toward the intercondylar space to a depth of approximately 7 to 10 mm and the appropriate volume (up to 0.6 mL) of test article were delivered. The stifle joint was then flexed several times. Then, the animal was placed on a warm water circulating blanket, and a bland ophthalmic ointment was applied during recovery. Buprenorphine SR (0.2 mg/kg) was administered via subcutaneous (SQ) injection between the shoulder blades during recovery. The animal was monitored for pain and discomfort during recovery and was returned to its home cage after complete recovery. An Elizabethan collar was positioned on animals chewing at dose sites, when needed. Additional pain management of animals was monitored by veterinary staff.

Assessment of toxicity was based on mortality, clinical observations (including qualitative food consumption), body weights, physical examinations, and clinical and anatomic pathology. Blood samples were collected for toxicokinetic evaluation. In particular, blood samples (approximately 0.5 mL) were collected via a jugular vein or medial auricular ear artery of the animals on Day 1 of the dosing phase. Samples were generally collected pre-dose and approximately 15 and 30 minutes and 1, 2, 4, 8, and 24 hours post-dose. Animals were not fasted for sample collections. Blood was collected into tubes containing potassium (K2) EDTA as the anticoagulant. Samples were maintained on chilled cryoracks prior to and after centrifugation. Samples were generally centrifuged within 1 hour of collection. Plasma was harvested and placed on dry ice until stored in a freezer, set to maintain at temperature in the range of −60° C. to −80° C. Samples remained stored until shipped on dry ice to a laboratory for analysis. Plasma samples were analyzed for capsaicin content. Toxicokinetic analysis was performed, which included analysis of Cmax, dose normalized maximum concentration (DN Cmax), Tmax, area under the curve from time 0 to the time of the last measurable concentration (calculated using the linear trapezoidal rule), area under the curve from time 0 to 24 hours (calculated using the linear trapezoidal rule), and elimination half-life. On the day of dosing, cageside observations were conducted for each animal at approximately 1, 4, and 8 hours post-dose. Post-dose observation start times were based on the dosing completion time for each animal. Abnormal findings or an indication of normal were recorded. Body weights were recorded twice during the pre-dose phase and on Days 1, 8, 15, and 22 of the dosing phase. Qualitative food consumption was recorded once daily (except on day of animal arrival) during the pre-dose and dosing phases; abnormal findings were recorded. Physical examinations were conducted once during the pre-dose phase and once Week 1 of the dosing phase; animals were examined by a Veterinarian/technical staff.

On Day 29 of the dosing phase, all animals were anesthetized with sodium pentobarbital, exsanguinated, and necropsied. Animals were not fasted prior to terminal procedures. Terminal body weights were recorded. A macroscopic examination of the external features of the carcass; external body orifices; abdominal, thoracic, and cranial cavities; organs; and tissues was performed. Organ weights were recorded at the scheduled sacrifice. Bone marrow smears (two slides) were prepared from the femur of each animal at scheduled sacrifices. All animals survived to the scheduled necropsy Synovial fluid from the knee of each animal was collected at scheduled sacrifices for cytological examination. A study-specific procedure was followed during collection of synovial fluid and was as follows. The animal was anesthetized with sodium pentobarbital and placed in dorsal recumbency. Hair was clipped if needed. The knee was wiped with isopropyl alcohol, and skin was cut away to expose the joint. The knee was positioned by a second restrainer at an approximate 90° angle, keeping the femur and tibia aligned and the knee straight. A 23 G×¾ inch×7 inch (0.6×19 mm×178 mm) needle was attached to a syringe. The synovial fluid was collected from the right femorotibial joint. The patella was located and palpated as the joint was entered midway between the proximal aspect of the patella and the tibial tuberosity on the lateral side. The needle was advanced with a slight angle in toward the intercondylar space. The syringe was pulled to approximately 2 mL when entering the capsule joint. The needle was advanced until entering into the membrane containing synovial fluid, which allowed the synovial fluid to enter the tubing. The pressure was released from the syringe to prevent pulling the sample into the syringe prior to the removal of the needle. The sample was then placed in a vial, and the tubing was cleared of the sample by using a pistol of a 50 µL pipette tip and pushing through the tubing. Samples were placed on wet ice until two synovial fluid smears were made, and the weight was then recorded. The remaining fluid was stored in a freezer, set to maintain at a temperature in the range of −60° C. to −80° C. Samples were subjected to cytological examination.

Part II—Results of Toxicity Analysis in Rabbits

No significant local or systemic adverse effects were observed attributable to administration of up to a 0.3 mg dose of trans-capsaicin by administration of Capsaicin Formulation A once on Day 1 of the dosing phase via intra-articular injection to the stifle joint of rabbits. The observed effects of administering Capsaicin Formulation A were limited to (i) mildly increased numbers of neutrophils (heterophils) and mononuclear cells in the synovial fluid of most animals administered trans-capsaicin at a dose of 0.1 mg or 0.3 mg, and (ii) minimally decreased total protein concentration, due to minimally decreased albumin concentration, in males administered trans-capsaicin at a dose of 0.3 mg, and (iii) minimally increased myxoid material in the synovium of the stifle joint, though this finding was considered nonadverse. No effects on hematology or coagulation were identified due to administration of Capsaicin Formulation A. No difference in macroscopic findings or organ weights was observed due to administration of Capsaicin Formulation A. No alteration in body weight or body weight gain was observed due to administration of Capsaicin Formulation A. No abnormalities were observed during physical examination due to administration of Capsaicin Formulation A.

Based on results from this experiment, the high-dose level of 0.3 mg trans-capsaicin is the no observed adverse effect level (NOAEL). At a trans-capsaicin dose level of 0.3 mg administered in the form of Capsaicin Formulation A, the Day 1 combined (males and females) mean Cmax and $AUC_{0-24}$ values for trans-capsaicin were 37.9 ng/mL and 27.8 ng·h/mL, respectively.

Example 8—Assessment of Toxicity for Exemplary Capsaicin Formulation Upon Administration to Dogs An aliquot of Capsaicin Formulation A was subjected to toxicity evaluation in purebred beagle dogs. Experimental Procedures and results are provided below.

Part I—Experimental Procedures for Toxicity Analysis in Purebred Beagle Dogs

An aliquot of test article (i.e., placebo (control) or Capsaicin Formulation A) was administered as a single dose via intraarticular injection to dogs, and analysis was performed to check for evidence of toxicity. Capsaicin Formulation A was prepared based on procedures described above for Capsaicin Formulation 1, and a description of Capsaicin Formulation A is provided in the following table.

| Capsaicin Formulation A |
| --- |
| An aqueous, capsaicin injectable formulation containing: |
|   a.  0.05% (w/w) of trans-capsaicin; |
|   b.  1% (w/w) of macrogol 15 hydroxystearate; |
|   c.  0.01% (w/w) dibutylated hydroxytoluene; |
|   d.  50 mM of buffer that is a mixture of sodium acetate and acetic acid; |
|   e.  0.025% (w/w) of ethylenediaminetetraacetic acid or a salt thereof; |
|   f.  0.6% (w/w) of sodium chloride; |
|   g.  q.s. with water (i.e., about 97.6% (w/w)); and |
| having a pH of 5.5. |

Procedurally, male and female purebred beagle dogs were received from Covance Research Products, Inc. in Cumberland, Va. Animals were acclimated to the test facility for 20 days (males) and 24 days (females) prior to initiation. At initiation of dosing, animals were 7 to 8 months old, and body weights ranged from 7.4 to 11.8 kg for males and 6.5 to 9.2 kg for females. Animals not used on study were placed in the stock colony. Animals were housed in stainless steel cages with Tenderfoot® flooring. Animals were socially housed by sex, unless individually housed during parts of the pre-dose phase, for study-related procedures, or for individual assessment of food consumption. Water was provided ad libitum. Animals were offered Certified Canine Diet #5007 (PMI NUTRITION INTERNATIONAL CERTIFIED LABDIET®); it was provided for 4 to 5 hours each day, unless otherwise specified. Feed was offered following the completion of dosing for each room on the day of dosing or at approximately the same time as the expected start of dosing (±2 hours) on days without dosing. For acclimation purposes, animals had access to feed for longer than 4 to 5 hours on the day of and the day after arrival. Beginning on Day 16 of the dosing phase for females, one animal (Group 3 female) was given canned food once daily.

The male and female dogs were assigned to groups and doses of test articled (i.e., placebo (control) or Capsaicin Formulation A) were administered as indicated in the following table.

| Group | No. of Animals Male | Female | Dose of Capsaicin (mg) | Dose Volume (mL) | Concentration of Capsaicin in the Dose (mg/mL) |
| --- | --- | --- | --- | --- | --- |
| 1 (control) | 4 | 4 | 0 | 2 | 0 |
| 2 | 4 | 4 | 0.1 | 0.2 | 0.5 |
| 3 | 4 | 4 | 0.3 | 0.6 | 0.5 |
| 4 | 4 | 4 | 1 | 2 | 0.5 |

Animals were administered a single dose of test article (i.e., placebo (control) or Capsaicin Formulation A) on Day 1 via intra-articular injection into the stifle joint. Dosing was followed by an observation period of 4 weeks. The vehicle control article (i.e., placebo) was the same as Capsaicin Formulation A except that it did not contain capsaicin. Prior to injection of test article, animals were fasted for the overnight period prior to dosing. Additionally, animals were pre-treated with an intra-articular injection of lidocaine into the right stifle joint on Day 1 of the dosing phase, prior to dose initiation. Animals were anesthetized for administration of lidocaine, which was administered as follows for each group:

| Group | Lidocaine Volume (mL) | Lidocaine Concentration |
| --- | --- | --- |
| 1 (control) | 0.5 | 4% |
| 2 | 2.0 | 1% |
| 3 | 1.5 | 1% |
| 4 | 0.5 | 4% |

Feed was returned following the completion of dosing.

Assessment of toxicity was based on mortality, clinical observations, body weights, food consumption, electrocardiography (ECG), synovial fluid collection, and clinical and anatomic pathology. Blood samples (approximately 2.0 mL) were collected via the jugular or cephalic vein on Day 1 of the dosing phase (see Protocol Deviations). Samples were collected pre-dose and approximately 15 and 30 minutes and 1, 2, 4, 8, and 24 hours post-dose. Animals were not fasted for sample collections, unless fasted for other study procedures. Blood was collected into tubes containing potassium (K2) EDTA as the anticoagulant. Samples were maintained on chilled cryoracks prior and were centrifuged within 1 hour of collection. Plasma was harvested and divided into two approximately aliquots and placed on dry ice, then stored in a freezer set to maintain at a temperature in the range of −60° C. to −80° C., until shipped. Aliquot 1 was shipped on dry ice to the testing laboratory for analysis and Aliquot 2 was retained as backup at the testing facility. Plasma samples were analyzed for capsaicin. Toxicokinetic analysis was performed, which included analysis of Cmax, dose normalized maximum concentration (DN Cmax), Tmax, area under the curve from time 0 to the time of the last measurable concentration (calculated using the linear trapezoidal rule), area under the curve from time 0 to 24 hours (calculated using the linear trapezoidal rule), and elimination half-life. Cageside observations were conducted for each animal once daily during the pre-dose and dosing phases, except on days when detailed observations were conducted. Abnormal findings were recorded. Detailed observations were conducted for each animal three times for males and four times for females during the pre-dose phase and on Days 1, 8, 15, 22, and 28 of the dosing phase. Detailed observations were also collected for each animal on the day of scheduled sacrifice (all surviving animals). Abnormal findings or an indication of normal was recorded. Unscheduled observations were recorded. On the day of dosing, cage-side observations were conducted for each animal at approximately 1, 4, and 8 hours post-dose. Post-dose observation start times for each animal were based on the dosing completion time for each animal. Abnormal findings or an indication of normal was recorded. Body weights were recorded three times for males and four times for females during the pre-dose phase and on Days 1, 8, 15, 22, 28 (females only), and 29 (males only) of the dosing phase. Quantitative food consumption was recorded weekly (unless fasted for other study procedures) to Week 4 and from Days 22 to 28 of the dosing phase. Electrocardiograms (ECGs) were recorded once during the pre-dose phase and once during Week 4 of the dosing phase. Electrocardiograms were recorded using eight leads. Blood samples for hematology, coagulation, and clinical chemistry were collected from fasted animals via a jugular or cephalic vein. Blood samples were collected twice during the pre-dose phase, on Day 2 of the dosing phase, and on the day of scheduled sacrifice. Urine samples for urinalysis were collected chilled during the overnight period before blood collection from animals fasted overnight. Urine samples were collected once during the pre-dose phase, on Day 2 of the dosing phase, and on the day of scheduled sacrifice. Synovial fluid was collected from the knee of all animals on the day of scheduled sacrifice.

On Day 29 of the dosing phase, all animals, having been fasted overnight, were anesthetized with sodium pentobarbital, exsanguinated, and necropsied. Terminal body weights were recorded for sacrificed animals. A macroscopic examination of the external features of the carcass; external body orifices; abdominal, thoracic, and cranial cavities; organs; and tissues was performed. Organ weights were recorded at the scheduled sacrifice. Paired organs were weighed together. Bone marrow smears (two slides) were prepared from the sternum of each animal at scheduled sacrifices.

Part II—Results of Toxicity Analysis in Dogs

No significant local or systemic adverse effects were observed attributable to administration of up to 1 mg dose of trans-capsaicin using Capsaicin Formulation A once on Day 1 of the dosing phase via intra-articular injection to the stifle joint of dogs. The observed effects of administering Capsaicin Formulation A were limited to (i) a minimally to mildly increased number of reactive mononuclear cells in the synovial fluid of the injected stifle, (ii) minimal to slight hypertrophy/hyperplasia and erosion/ulceration and minimal hemorrhage and degeneration of the synovium, and (iii) minimal pigment in the synovium of one female administered a 1 mg dose of trans-capsaicin using Capsaicin Formulation A. No alteration in body weight or body weight gain was observed attributable to administration of Capsaicin Formulation A. No effect on food consumption was observed attributable to administration of Capsaicin Formulation A. No test article-related change in PR interval, QRS duration, QT interval, corrected QT (QTc) interval, or heart rate was observed on Day 23 (males) or 25 (females) of the dosing phase in animals administered 0.1, 0.3, or 1 mg of trans-capsaicin via Capsaicin Formulation A. No abnormal ECG waveforms or arrhythmias attributed to Capsaicin Formulation A were observed during qualitative assessment of the ECGs. No effects on hematology, clinical chemistry, coagulation, or urinalysis tests were identified attributable to administration of Capsaicin Formulation A. Minimally to mildly increased total white blood cell count, due to increased absolute neutrophil and/or monocyte counts, and minimally increased fibrinogen concentration were noted on Day 2 in most animals of all groups, including controls, and were considered secondary to study procedures. No effect on organ weight parameters attributable to Capsaicin Formulation A was observed.

Based on these results, the high-dose level of 1 mg of trans-capsaicin administered via Capsaicin Formulation A is the no observed adverse effect level (NOAEL). At a dose level of 1 mg trans-capsaicin administered in the form of Capsaicin Formulation A, the Day 1 combined (males and females) mean $C_{max}$ and $AUC_{0-24}$ values for trans-capsaicin were 9.21 ng/mL and 21.7 ng·h/mL, respectively.

Example 9—Autoclave Steam Sterilization of an Exemplary Capsaicin Formulation

An aliquot of Capsaicin Formulation A was placed into a container and subjected to autoclave steam sterilization. Capsaicin Formulation A was prepared based on procedures described above for Capsaicin Formulation 1, and a description of Capsaicin Formulation A is provided in the following table.

| Capsaicin Formulation A |
|---|
| An aqueous, capsaicin injectable formulation containing:<br>a. 0.05% (w/w) of trans-capsaicin;<br>b. 1% (w/w) of macrogol 15 hydroxystearate;<br>c. 0.01% (w/w) dibutylated hydroxytoluene;<br>d. 50 mM of buffer that is a mixture of sodium acetate and acetic acid;<br>e. 0.025% (w/w) of ethylenediaminetetraacetic acid or a salt thereof;<br>f. 0.6% (w/w) of sodium chloride;<br>g. q.s. with water (i.e., about 97.6% (w/w)); and<br>having a pH of 5.5. |

Experimental Procedures and results are provided below.

Part I—Experimental Procedure for Sterilization Process Providing a $F_0$-Value in the Range of 8.8 to 8.9

An aliquot of Capsaicin Formulation A was placed into a sealed container. The sealed container containing Capsaicin Formulation A was then placed into an autoclave and subjected to sterilization conditions to achieve an $F_0$-value in the range of 8.8 to 8.9. The sterilization conditions involving heating the sterilization chamber of the autoclave to a temperature in the range of 121.7° C. to 122.0° C. and a pressure of about 3.4 barr, holding at the aforementioned conditions for a duration of about 7 minutes, and then returning the autoclave chamber to ambient temperature and pressure. Thereafter, an aliquot of the sterilized Capsaicin Formulation A was analyzed by HPLC, and the HPLC chromatogram compared to the HPLC chromatogram of an aliquot of Capsaicin Formulation A that had not undergone the sterilization procedure.

Part II—Results

HPLC analysis of the aliquot of Capsaicin Formulation A subjected to the above sterilization revealed that there was no significant loss of capsaicin due to the sterilization procedure. The Capsaicin Formulation A was found to be stable to the sterilization conditions.

Part III—Experimental Procedure for Sterilization Process Providing a $F_0$-Value in the Range of 25.7 to 26.1

An aliquot of Capsaicin Formulation A was placed into a sealed container. The sealed container containing Capsaicin Formulation A was then placed into an autoclave and subjected to sterilization conditions to achieve an $F_0$-value in the range of 25.7 to 26.1. The sterilization conditions involving heating the sterilization chamber of the autoclave to a temperature in the range of 121.0° C. to 123.0° C. and pressure of about 3.4 barr, holding at the aforementioned conditions for a duration of about 22 minutes, and then returning the autoclave chamber to ambient temperature and pressure. Thereafter, an aliquot of the sterilized Capsaicin Formulation A was analyzed by HPLC.

Part IV—Results

HPLC analysis of the aliquot of Capsaicin Formulation A subjected to the above sterilization revealed that there was no significant loss of capsaicin due to the sterilization procedure. The Capsaicin Formulation A was found to be stable to the sterilization conditions.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. An aqueous, capsaicin injectable formulation, comprising
   a. about 0.04% (w/w) to about 0.06% (w/w) of capsaicin;
   b. about 0.5% (w/w) to about 1.5% (w/w) of a solubilizing agent, wherein the solubilizing agent comprises

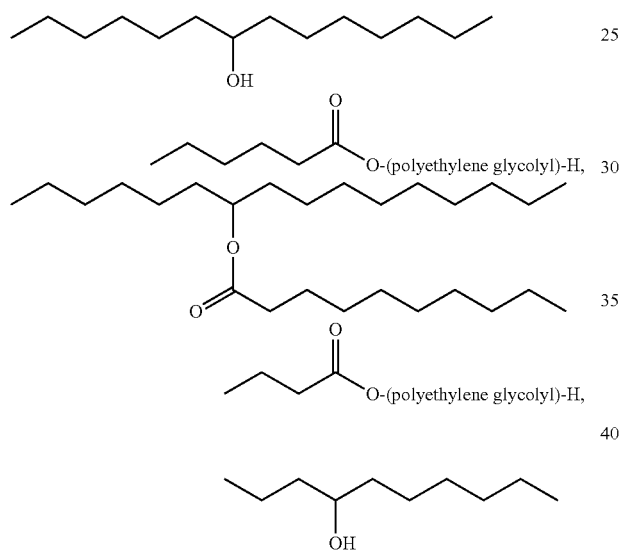

and polyethylene glycol;
   c. about 0.005% (w/w) to about 0.015% (w/w) of an antioxidant;
   d. about 0.2% (w/w) to about 1% (w/w) of an alkali metal acetate;
   e. about 0.01% (w/w) to about 0.05% (w/w) of a chelating agent;
   f. about 0.3% (w/w) to about 0.9% (w/w) of a tonicity modifier;
   g. at least 96% (w/w) water; and
      having a pH in the range of about 5 to about 6; wherein the formulation contains less than 1% (w/w) of capsaicin-dimer having the following structure:

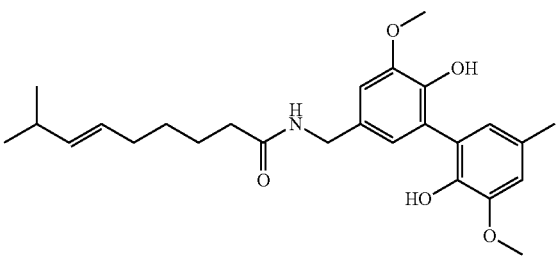

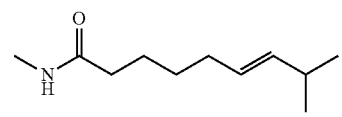

2. The formulation of claim 1, wherein the solubilizing agent comprises (a) from 68% (w/w) to 72% (w/w) of a mixture of

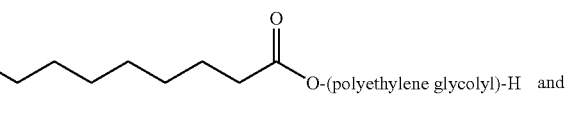

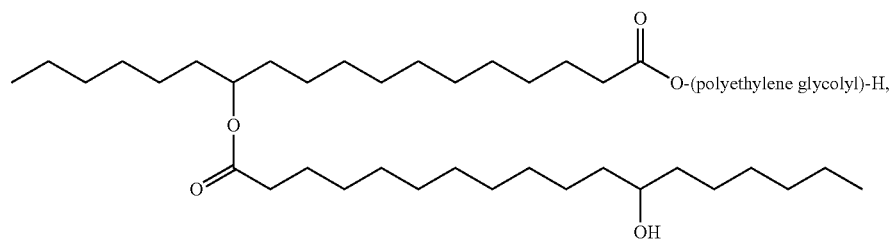

and (b) from 28% (w/w) to 32% (w/w) polyethylene glycol.

3. The formulation of claim 1, wherein any polyethylene glycol or polyethylene glycolyl each independently have a weight-average molecular weight in the range of about 600 g/mol to about 750 g/mol.

4. The formulation of claim 1, wherein any polyethylene glycol or polyethylene glycolyl each independently have a weight-average molecular weight of about 660 g/mol.

5. The formulation of claim 2, wherein any polyethylene glycol or polyethylene glycolyl each independently have a weight-average molecular weight in the range of about 600 g/mol to about 750 g/mol.

6. The formulation of claim 2, wherein any polyethylene glycol or polyethylene glycolyl each independently have a weight-average molecular weight of about 660 g/mol.

7. The formulation of claim 1, wherein upon storage at 25° C. for 24 weeks, the formulation contains less than 0.6% (w/w) of the capsaicin-dimer.

8. The formulation of claim 2, wherein upon storage at 25° C. for 24 weeks, the formulation contains less than 0.6% (w/w) of the capsaicin-dimer.

9. The formulation of claim 5, wherein upon storage at 25° C. for 24 weeks, the formulation contains less than 0.6% (w/w) of the capsaicin-dimer.

15. The formulation of claim 2, wherein upon storage at 25° C. for 24 weeks, the formulation contains less than 0.1% (w/w) of 5-oxo-capsaicin.

16. The formulation of claim 4, wherein upon storage at 25° C. for 24 weeks, the formulation contains less than 0.1% (w/w) of 5-oxo-capsaicin.

17. The formulation of claim 6, wherein upon storage at 25° C. for 24 weeks, the formulation contains less than 0.1% (w/w) of 5-oxo-capsaicin.

18. The formulation of claim 8, wherein upon storage at 25° C. for 24 weeks, the formulation contains less than 0.1% (w/w) of 5-oxo-capsaicin.

19. The formulation of claim 10, wherein upon storage at 25° C. for 24 weeks, the formulation contains less than 0.1% (w/w) of 5-oxo-capsaicin.

20. An aqueous, capsaicin injectable formulation, comprising
   a. about 0.04% (w/w) to about 0.06% (w/w) of capsaicin;
   b. about 0.8% (w/w) to about 1.2% (w/w) of a solubilizing agent, wherein the solubilizing agent comprises (a) about 70% (w/w) of a mixture of
   and (b) about 30% (w/w) polyethylene glycol;

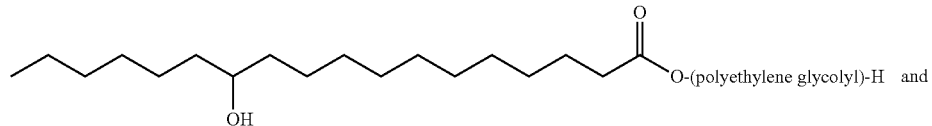

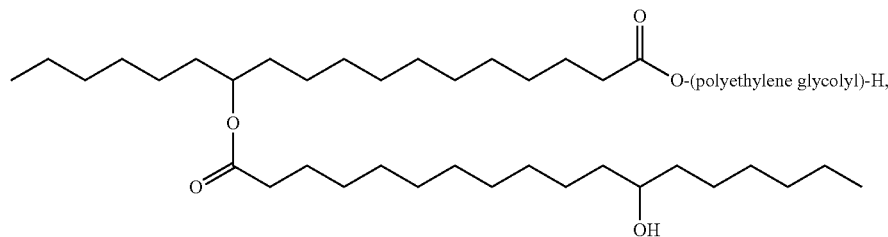

10. The formulation of claim 6, wherein upon storage at 25° C. for 24 weeks, the formulation contains less than 0.6% (w/w) of the capsaicin-dimer.

11. The formulation of claim 1, wherein the formulation contains less than 0.1% (w/w) of 5-oxo-capsaicin.

12. The formulation of claim 2, wherein the formulation contains less than 0.1% (w/w) of 5-oxo-capsaicin.

13. The formulation of claim 6, wherein the formulation contains less than 0.1% (w/w) of 5-oxo-capsaicin.

14. The formulation of claim 1, wherein upon storage at 25° C. for 24 weeks, the formulation contains less than 0.1% (w/w) of 5-oxo-capsaicin.

c. about 0.005% (w/w) to about 0.015% (w/w) of dibutylhydroxytoluene;
   d. about 0.2% (w/w) to about 1% (w/w) of sodium acetate;
   e. about 0.01% (w/w) to about 0.05% (w/w) of ethylenediaminetetraacetic acid or a salt thereof;
   f. about 0.3% (w/w) to about 0.9% (w/w) of sodium chloride;
   g. at least 96% (w/w) water; and
   having a pH in the range of about 5 to about 6; wherein the formulation contains less than 1% (w/w) of capsaicin-dimer having the following structure:

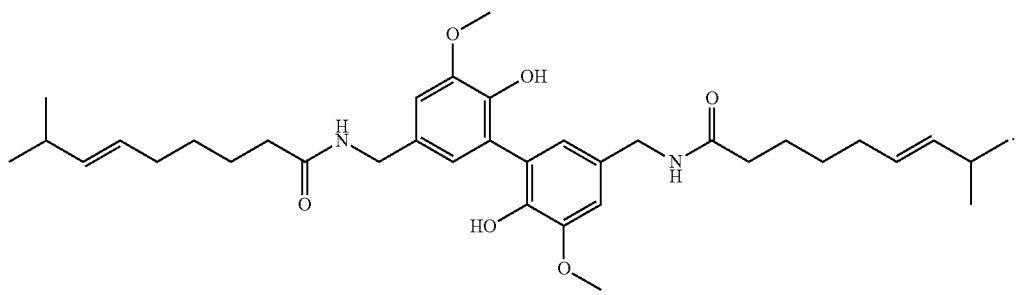 [SMILES: COc1cc(CNC(=O)CCCC/C=C/C(C)C)cc(-c2cc(CNC(=O)CCCC/C=C/C(C)C)cc(OC)c2O)c1O]

21. The formulation of claim 20, wherein any polyethylene glycol or polyethylene glycolyl each independently have a weight-average molecular weight in the range of about 600 g/mol to about 750 g/mol.

22. The formulation of claim 20, wherein any polyethylene glycol or polyethylene glycolyl each independently have a weight-average molecular weight of about 660 g/mol.

23. The formulation of claim 20, wherein upon storage at 25° C. for 24 weeks, the formulation contains less than 0.6% (w/w) of the capsaicin-dimer.

24. The formulation of claim 21, wherein upon storage at 25° C. for 24 weeks, the formulation contains less than 0.6% (w/w) of the capsaicin-dimer.

25. The formulation of claim 22, wherein upon storage at 25° C. for 24 weeks, the formulation contains less than 0.6% (w/w) of the capsaicin-dimer.

26. The formulation of claim 20, wherein the formulation contains less than 0.1% (w/w) of 5-oxo-capsaicin.

27. The formulation of claim 22, wherein the formulation contains less than 0.1% (w/w) of 5-oxo-capsaicin.

28. The formulation of claim 20, wherein upon storage at 25° C. for 24 weeks, the formulation contains less than 0.1% (w/w) of 5-oxo-capsaicin.

29. The formulation of claim 22, wherein upon storage at 25° C. for 24 weeks, the formulation contains less than 0.1% (w/w) of 5-oxo-capsaicin.

30. The formulation of claim 25, wherein upon storage at 25° C. for 24 weeks, the formulation contains less than 0.1% (w/w) of 5-oxo-capsaicin.

* * * * *